US011696959B2

(12) United States Patent
Cao et al.

(10) Patent No.: US 11,696,959 B2
(45) Date of Patent: Jul. 11, 2023

(54) NANOPARTICLE-CELL CONSTRUCT WITH PLATINUM ANTI-CANCER AGENT

(71) Applicant: City of Hope, Duarte, CA (US)

(72) Inventors: Pengpeng Cao, Duarte, CA (US); Jacob Berlin, Monrovia, CA (US); Karen Aboody, Arcadia, CA (US); Rachael Mooney, Hacienda Heighs, CA (US); Wafa Abidi, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 58 days.

(21) Appl. No.: 16/066,628

(22) PCT Filed: Dec. 28, 2016

(86) PCT No.: PCT/US2016/068978
§ 371 (c)(1),
(2) Date: Jun. 27, 2018

(87) PCT Pub. No.: WO2017/117275
PCT Pub. Date: Jul. 6, 2017

(65) Prior Publication Data
US 2019/0022246 A1    Jan. 24, 2019

Related U.S. Application Data

(60) Provisional application No. 62/274,034, filed on Dec. 31, 2015.

(51) Int. Cl.
| | |
|---|---|
| *A61K 47/34* | (2017.01) |
| *A61K 47/69* | (2017.01) |
| *A61K 33/243* | (2019.01) |
| *A61P 35/00* | (2006.01) |
| *A61K 9/00* | (2006.01) |
| A61K 51/00 | (2006.01) |
| A61K 33/242 | (2019.01) |
| A61K 33/244 | (2019.01) |
| B82Y 5/00 | (2011.01) |

(52) U.S. Cl.
CPC ........ *A61K 47/6923* (2017.08); *A61K 9/0019* (2013.01); *A61K 33/243* (2019.01); *A61K 47/6901* (2017.08); *A61K 47/6929* (2017.08); *A61P 35/00* (2018.01); *A61K 33/242* (2019.01); *A61K 33/244* (2019.01); *A61K 51/00* (2013.01); *A61K 2300/00* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 2005/0037075 A1* | 2/2005 | Farokhzad | A61K 47/593 424/468 |
| 2006/0240009 A1* | 10/2006 | Zalipsky | A61K 47/6913 424/144.1 |
| 2009/0181398 A1* | 7/2009 | Bauer | A61K 49/0058 435/6.11 |
| 2010/0233085 A1 | 9/2010 | Kwon et al. | |
| 2012/0252140 A1* | 10/2012 | Aimiya | C01B 33/12 436/501 |
| 2013/0039848 A1* | 2/2013 | Bradbury | A61K 51/1244 424/1.37 |
| 2013/0337066 A1 | 12/2013 | Zhang et al. | |
| 2014/0079774 A1 | 3/2014 | Brinker et al. | |

OTHER PUBLICATIONS

Chen, F., et al. J. Nucl. Med. (2014), 55; Suppl. 1; 547.*
Colilla, M., et al. Biomater. Sci. (2013), 1; 114-134.*
Ahn, B., et al. J. Mater. Chem. B (2013), 1; 2829-2836.*
He, Q., et al. Biomaterials (2010), 31; 1085-1092.*
Stephan, M. T., et al. Nano Today (2011), 6; 309-325.*
Banditelli, G., et al. Inorganica Chimica Acta (2002), 330; 72-81.*
Jokerst, J., et al. Nanomedicine (2011), 6(4); 715-728.*
Cao, P. et al. (May 2016). "Stem Cell Nanoparticle Constructs for Targeted Ovarian Cancer Therapy," *Molecular Therapy* 24(Supplement 1):Abstract 209; S81.
Della Rocca, J. et al. (Oct. 24, 2011, e-published Sep. 14, 2011). "Polysilsesquioxane nanoparticles for targeted platin-based cancer chemotherapy by triggered release," *Angew Chem Int Ed Engl* 50(44):10330-10334.
Gilchrist, M. et al. (2013). "Harnessing neural stem cell tumor tropism for targeted nanoparticle delivery: Potential for ovarian cancer therapy," AACR Poster Presentation, 1 page.
International Search Report dated Mar. 14, 2017, for PCT Application No. PCT/US2016/068978, filed Dec. 28, 2016, 3 pages.
Mooney, R. et al. (Feb. 2014). "Neural stem cells improve intracranial nanoparticle retention and tumor-selective distribution," *Future Oncol* 10(3):401-415.
Mooney, R. et al. (Oct. 10, 2014, e-published Jun. 18, 2014). "Conjugation of pH-responsive nanoparticles to neural stem cells improves intratumoral therapy," *Journal of Controlled Release* 191:82-89.
Mooney, R. et al. (Dec. 23, 2014, e-published Nov. 17, 2014). "Neural stem cell-mediated intratumoral delivery of gold nanorods improves photothermal therapy," *ACS Nano* 8(12):12450-12460.
Written Opinion dated Mar. 14, 2017, for PCT Application No. PCT/US2016/068978, filed Dec. 28, 2016, 7 pages.

* cited by examiner

*Primary Examiner* — Kevin S Orwig
(74) *Attorney, Agent, or Firm* — Irina E. Britva; Mintz, Levin, Cohn, Ferris, Glovsky and Popeo, P.C.

(57) ABSTRACT

The disclosure provides, inter alia, compositions including cell-nanoparticle constructs and drug loaded nanoparticles, and methods for their use in the treatment of cancer. Also provided are unmodified cisplatin molecules encapsulated by silica nanoparticles, and their use in the treatment of cancer.

12 Claims, 25 Drawing Sheets

NANOPARTICLE-CELL CONSTRUCT WITH PLATINUM ANTI-CANCER AGENT

CROSS-REFERENCES TO RELATED APPLICATIONS

This application is the national stage filing under USC 371 of international application PCT/US2016/068978, filed Dec. 28, 2016, which claims the benefit of U.S. Provisional Application No. 62/274,034, filed Dec. 31, 2015, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant number R01 CA197359 awarded by the National Institutes of Health. The government has certain rights in the invention.

BACKGROUND

One goal of nanomedicine is to design and synthesize drug delivery vehicles that can carry sufficient drug loads, efficiently cross physiological barriers to reach target sites, and safely and sustainably treat diseases. Organic nanomedicines, including liposomes, drug-polymer conjugates, dendrimers, polymeric micelles and nanoparticles (NPs), have been studied as potential drug delivery systems. Each delivery platform has its advantages. For example, high drug loadings have been achieved in liposomes, but the intrinsic structural stability of liposomes is undesirably low, especially under fluid shear stress during circulation.

Silica NPs used for biomedical applications can be categorized as mesoporous or nonporous (solid) NPs, both of which bearing amorphous silica structure. Mesoporous silica NPs characterized by mesopores (2-50 nm pore size) are widely used for delivery of active payloads based on physical or chemical adsorption. In contrast, nonporous silica NPs often deliver cargo through encapsulation or conjugation.

Neural Stem Cells (NSCs) have demonstrated inherent tumor tropic properties (e.g. to ovarian cancer cells) in vitro and in vivo following intraperitoneal administration. However, NSCs generally do not intrinsically have anti-tumor efficacy. As NSC-based therapy moves into the clinic, there is a need to develop complementary techniques to enable targeted delivery of chemotherapeutics by NSCs. Disclosed herein, inter alia, are solutions to these and other problems in the art.

BRIEF SUMMARY OF THE INVENTION

In an aspect is provided a silica nanoparticle including a platinum anti-cancer agent, wherein the platinum anti-cancer agent is conjugated to silica directly, though an oxygen linker, or through a nitrogen linker.

In an aspect is provided a cell including a nanoparticle described herein. In embodiments, the cell is a tumor tropic cell, macrophage, stem cell (e.g., neural or mesenchymal), or T-cell.

In another aspect is provided a nanoparticle-cell construct including an inorganic nanoparticle covalently attached to a protein through a covalent linker, the covalent linker having the formula: (Ia) -$L^2$-$X^1$-$L^1$-$X^2$-$L^3$- or (Ib) -$L^2$-$X^2$-$L^3$-; wherein $X^1$ and $X^2$ are independently a bioconjugate linker or a bond, wherein at least one of $X^1$ or $X^2$ is a bioconjugate linker; $L^1$ is independently a polymeric linker; $L^2$ is independently a bond, —$NR^{1a}$—, —O—, —S—, —C(O)—, —C(O)O—, —S(O)—, —S(O)$_2$—, —$NR^{1a}$C(O)—, —C(O)$NR^{1b}$—, —C(O)(CH$_2$)$_{z1}$—, —$NR^{1a}$C(O)O—, —$NR^{1a}$C(O)$NR^{1b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^3$ is independently a bond, —$NR^{2a}$—, —O—, —S—, —C(O)—, —C(O)O—, —S(O)—, —S(O)$_2$—, —$NR^{2a}$C(O)—, —C(O)$NR^{2b}$—, —C(O)(CH$_2$)$_{z2}$—, —$NR^{2a}$C(O)O—, —$NR^{2a}$C(O)$NR^{2b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{1a}$, $R^{2a}$, $R^{1b}$, and $R^{2b}$ are independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and the symbols z1 and z2 are independently an integer from 1 to 10.

In another aspect, is provided a pharmaceutical composition including a pharmaceutically acceptable excipient and a nanoparticle, cell, or nanoparticle-cell construct, each as described herein or a pharmaceutically acceptable salt thereof.

In an aspect is provided a method of treating cancer in a subject in need of such treatment, the method including administering to the subject in need thereof a therapeutically effective amount of the nanoparticle, the cell, or the nanoparticle-cell construct, each as described herein.

BRIEF DESCRIPTION OF THE DRAWINGS

FIG. 14 shows 80:20 non-functional PEG:functionalized PEG. NSCs were labeled with PEGylated SiNPs at both 4° C. and 37° C. for 30 min in FIG. 14. At the composition of 80%:20%, the amount of Mal-PEG on the NP surface was too low and NSCs were not sufficiently labeled with SiNPs.

FIG. 15 shows 50:50 non-functional PEG:functionalized PEG. NSCs were labeled with PEGylated SiNPs at 37° C. for 30 min in FIG. 15. At the composition of 50%:50%, NSCs were labeled with much more NP-PEG11-3400. It appears that the shorter functional Mal-PEG3400 works better than the Mal-PEG5000. To ensure the reactivity between maleimide-thiol covalent bond formation, all future cell labeling steps were done at 37° C.

DETAILED DESCRIPTION

Figure 1:
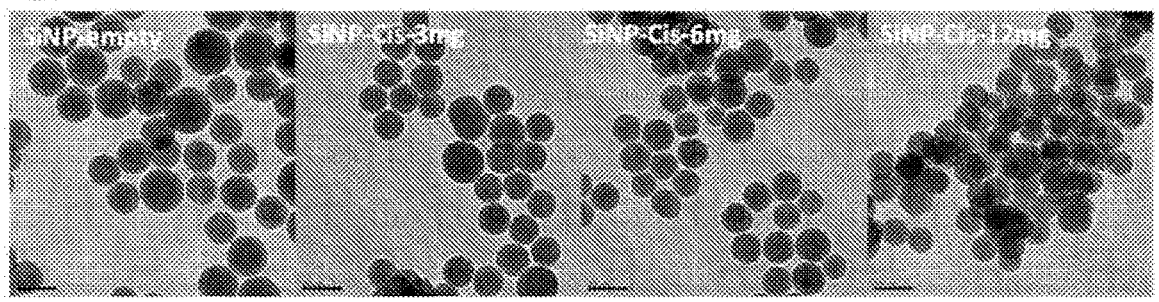
FIG. 1. A TEM image of cisplatin loaded nanoparticles at different loading levels. Comparing to the control nanoparticles SiNP-empty (i.e. without a drug added), SiNP-Cis particles loaded with 3 mg, 6 mg, and 12 mg cisplatin also maintained their morphology. They appear to be roughly the same size and shape as the control NPs. The nanoparticles are monodisperse and colloidally stable in water.

Described herein, inter alia, are stem cell-nanoparticle constructs and drug loaded nanoparticles for targeted and selective tumor killing in patients suffering cancer. Also disclosed herein is the use of nanoparticles (NPs), which can be loaded with a broad spectrum of chemotherapeutic agents (e.g., platinum anti-cancer agents) for delivery and dissemination at tumor sites. In embodiments, delayed-drug release NP/NSC constructs are provided to realize a modular and general drug targeting system for ovarian cancer.

In embodiments, unmodified cisplatin molecules are encapsulated by silica NPs via a one-pot reaction, and these cisplatin-NPs demonstrated delayed drug release over 3 days via in vitro efficacy MTT assay. NSCs may be labeled with cisplatin-NPs and the resulting NSC-NP constructs injected in mice bearing ovarian cancer tumors. The amount of Pt accumulation may be quantified at tumors and in organs by ICP-MS. Our data demonstrated that NSC-NP constructs have much superior accumulation and retention of Pt in tumors than both free cisplatin and free cisplatin-NPs.

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR" ", —NR—C(NR'R")=NR'", —S(O)R', —S(O)$_2$R', —S(O)$_2$NR'R", —NRSO$_2$R', —NR'NR"R'", —ONR'R", —NR'C=(O)NR'"R'''', —CN, —NO$_2$, in a number ranging from zero to (2m'+1), where m' is the total number of carbon atoms in such radical. R, R', R", R'", and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR' R'')=NR''', —S(O)R', —S(O)$_2$R', —S(O)$_2$NR'R'', —NRSO$_2$R', —NR'NR''R''', —ONR'R'', —NR'C=(O)NR''NR'''R'''', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C''R''R''')$_d$—, where s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat hyperproliferative disorders, such as cancer (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer). For example certain methods herein treat cancer by decreasing or reducing or preventing the occurrence, growth, metastasis, or progression of cancer or by decreasing or reducing or preventing a symptom of cancer. Symptoms of cancer (e.g., ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer) would be known or may be determined by a person of ordinary skill in the art. The term "treating" and conjugations thereof, include prevention of an injury, pathology, condition, or disease (e.g. preventing the development of one or more symptoms of cancer (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include ovarian cancer, lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma, cisplatin resistant lung cancer, carboplatin resistant lung cancer, platinum-based compound resistant lung cancer), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. In embodiments "cancer" refers to a cancer resistant to an anti-cancer therapy (e.g. treatment with an anti-cancer agent).

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer, ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example cancer may be treated with a composition (e.g. compound, composition, nanoparticle, or conjugate, all as described herein) effective for inhibiting DNA replication.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In embodiments, inhibition refers to a decrease in DNA replication or transcription. In some embodiments inhibition refers to reduction of a disease or symptoms of disease (e.g. cancer, ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer). Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In embodiments, the disease is cancer. In embodiments, the disease is ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) may be contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents (e.g. anti-cancer agents) known to be useful in treating a disease described herein (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent (e.g. anti-cancer agent). Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine;

toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature. Sulfur-containing amino acids refers to naturally occurring and synthetic amino acids comprising sulfur, e.g., methionine, cysteine, homocysteine, and taurine.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g. —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine). The term "haloacetyl," as used herein, refers to a functional group having the formula:

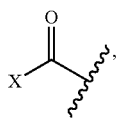

wherein X is a halogen.

Useful bioconjugate reactive groups used for bioconjugate chemistries herein include, for example:
  (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
  (b) hydroxyl groups which can be converted to esters, ethers, aldehydes, etc.
  (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
  (d) dienophile groups which are capable of participating in Diels-Alder reactions such as, for example, maleimido or maleimide groups;
  (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
  (f) sulfonyl halide groups for subsequent reaction with amines, for example, to form sulfonamides;
  (g) thiol groups, which can be converted to disulfides, reacted with acyl halides, or bonded to metals such as gold, or react with maleimides;
  (h) amine or sulfhydryl groups (e.g., present in cysteine), which can be, for example, acylated, alkylated or oxidized;
  (i) alkenes, which can undergo, for example, cycloadditions, acylation, Michael addition, etc;
  (j) epoxides, which can react with, for example, amines and hydroxyl compounds;
  (k) phosphoramidites and other standard functional groups useful in nucleic acid synthesis;
  (l) metal silicon oxide bonding; and
  (m) metal bonding to reactive phosphorus groups (e.g. phosphines) to form, for example, phosphate diester bonds.
  (n) azides coupled to alkynes using copper catalyzed cycloaddition click chemistry.
  (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

A "neural stem cell" as used herein, refers to a self-renewing multipotent cell capable of generating cells of the nervous system (e.g., neurons, astrocytes, and oligodendrocytes). In embodiments, a neural stem cell is a tropic stem cell that can self-renew and give rise to differentiated progenitor cells, such as HB1.F3 neural stem cells.

A "nanoparticle," as used herein, is a particle wherein the longest diameter is less than or equal to 1000 nanometers. Nanoparticles may be composed of any appropriate material. For example, nanoparticle cores may include appropriate metals and metal oxides thereof (e.g., a metal nanoparticle core), carbon (e.g., an organic nanoparticle core) silicon and oxides thereof (e.g., a silicon nanoparticle core) or boron and oxides thereof (e.g., a boron nanoparticle core), or mixtures thereof. Nanoparticles may be composed of at least two distinct materials, one material (e.g., iron oxide) forms the core and the other material forms the shell (e.g., silica) surrounding the core.

An "inorganic nanoparticle" refers to a nanoparticle without carbon. For example, an inorganic nanoparticle may refer to a metal or metal oxide thereof (e.g., gold nanoparticle, iron nanoparticle) silicon and oxides thereof (e.g., a silica nanoparticle), or titanium and oxides thereof (e.g., titanium dioxide nanoparticle). In embodiments, the inorganic nanoparticle is a silica nanoparticle. The inorganic nanoparticle may be a metal nanoparticle. When the nanoparticle is a metal, the metal may be titanium, zirconium, gold, silver, platinum, cerium, arsenic, iron, aluminum or silicon. The metal nanoparticle may be titanium, zirconium, gold, silver, or platinum and appropriate metal oxides thereof. In embodiments, the nanoparticle is titanium oxide, zirconium oxide, cerium oxide, arsenic oxide, iron oxide, aluminum oxide, or silicon oxide. The metal oxide nanoparticle may be titanium oxide or zirconium oxide. The nanoparticle may be titanium. The nanoparticle may be gold. In embodiments, the metal nanoparticle is a gold nanoparticle. In embodiments, the inorganic nanoparticle may further include a moiety which contains carbon (e.g., carboplatin).

The term "silica nanoparticle" is used according to its plain and ordinary meaning and refers to a nanoparticle containing Si atoms (e.g., in a tetrahedral coordination) with 4 oxygen atoms surrounding a central Si atom. A person of ordinary skill in the art would recognize that the silica nanoparticle typically includes terminal oxygen atoms (e.g., the oxygens on the surface of the nanoparticle) that are hydroxyl moieties. A silica nanoparticle is a particle wherein the longest diameter is typically less than or equal to 1000 nanometers comprising a matrix of silicon-oxygen bonds. Where the silica nanoparticle includes a platinum anti-cancer agent, one or more of the silicon oxygen bonds within the silica nanoparticle may be replaced, with the Si atom bonded to platinum either directly (i.e., a Pt—Si bond), though an oxygen linker (i.e., an oxygen bound to Si, thereby forming a —Si—O—Pt— bond), or through a nitrogen linker (i.e., a nitrogen bound to Si, thereby forming an —Si—NH—Pt— bond) as described herein. In embodiments, a nanoparticle has a shortest diameter greater than or equal to 1 nanometer (e.g., diameter from 1 to 1000 nanometers). In embodiments, the silica nanoparticle is mesoporous. In embodiments, the silica nanoparticle is nonporous.

A functionalized silica nanoparticle, as used herein, may refer to the post hoc conjugation (i.e. conjugation after the formation of the silica nanoparticle) of a moiety to the hydroxyl surface of a nanoparticle. For example, a silica nanoparticle may be further functionalized to include additional atoms (e.g., nitrogen) or chemical entities (e.g., polymeric moieties or bioconjugate group). For example, when the silica nanoparticle is further functionalized with a nitrogen containing compound, one of the surface oxygen atoms surrounding the Si atom may be replaced with a nitrogen containing moiety.

In contrast to a functionalized silica nanoparticle, an unmodified silica nanoparticle refers to a silica nanoparticle which has not been further functionalized. Thus, for example, an unmodified silica nanoparticle does not include a nitrogen containing moiety (e.g., terminal amine moieties). For example, an unmodified silica nanoparticle refers to a silica nanoparticle as synthesized without post hoc functionalization. Thus, in embodiments, the unmodified silica nanoparticles includes the following example:

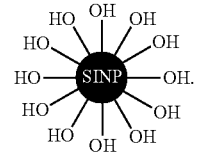

As used herein, the terms "bare silica nanoparticle" and "unmodified silica nanoparticle" are synonymous and interchangeable.

The term "platinum anti-cancer agent" is used in accordance with its common meaning and refers to an anti-cancer agent including coordinated platinum. For example, a platinum anti-cancer agent may be cisplatin, carboplatin, oxaliplatin, satraplatin, lobaplatin, picoplatin, heptaplatin, nedaplatin, triplatin, or a platinum containing compound described herein. In embodiments, a platinum anti-cancer agent includes a platinum salt (e.g, $K_2[PtCl_4]$). In embodiments, the platinum anti-cancer agent is a platinum anti-cancer agent described in U.S. Pat. No. 8,455,543, which is incorporated herein in its entirety for all purposes.

A "detectable agent" or "detectable compound" is a composition detectable by spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$ $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}I$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition (e.g., a nanoparticle or silica nanoparticle).

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. Enzymes that may be used as imaging agents in accordance with the embodiments of the disclosure include, but are not limited to, horseradish peroxidase, alkaline phosphatase, acid phoshatase, glucose oxidase, β-galactosidase, β-glucoronidase or β-lactamase. Such enzymes may be used in combination with a chromogen, a fluorogenic compound or a luminogenic compound to generate a detectable signal.

The term "polymeric" refers to a molecule including repeating subunits (e.g., polymerized monomers). For example, polymeric molecules may be based upon polyethylene glycol (PEG), poly[amino(1-oxo-1,6-hexanediyl)], or poly(oxy-1,2-ethanediyloxycarbonyl-1,4-phenylenecarbonyl). See, for example, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA, which are incorporated by reference in their entirety for all purposes.

The term "polymerizable monomer" is used in accordance with its meaning in the art of polymer chemistry and refers to a compound that may covalently bind chemically to other monomer molecules (such as other polymerizable monomers that are the same or different) to form a polymer.

The term "branched polymer" is used in accordance with its meaning in the art of polymer chemistry and refers to a molecule including repeating subunits, wherein at least one repeating subunit (e.g., polymerizable monomer) is covalently bound to a different subunit (e.g., polymerizable monomer). For example a branched polymer has the formula:

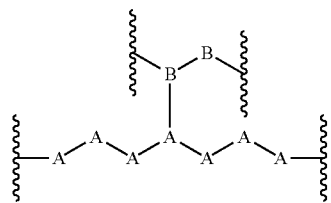

wherein 'A' is the first repeating subunit and 'B' is the second repeating subunit. In embodiments, the first repeating subunit (e.g., polyethylene glycol) is optionally different than the second repeating subunit (e.g., polymethylene glycol).

The term "unmodified platinum anti-cancer agent" as used herein refers to a platinum anti-cancer agent which is not modified prior to incorporation into the silica nanoparticle, wherein the platinum anti-cancer agent is conjugated to silica directly, though an oxygen linker, or through a nitrogen linker. Where an unmodified platinum anti-cancer agent is incorporated into the silica nanoparticle herein, the resulting nanoparticle may be referred to as including an "unmodified platinum anti-cancer agent" even though the platinum anti-cancer agent may have reacted with a portion of the silica nanoparticle during or subsequent to the incorporation process.

II. COMPOUNDS

In an aspect is provided a silica nanoparticle including a platinum anti-cancer agent, wherein the platinum anti-cancer agent is conjugated to silica directly (i.e., a Pt—Si bond), the platinum anti-cancer agent is conjugated to silica though an oxygen linker (i.e., an oxygen bound to Si, thereby forming a —Si—O—Pt— bond), or the platinum anti-cancer agent is conjugated to silica through a nitrogen linker (i.e., a nitrogen bound to Si, thereby forming an —Si—NH—Pt— bond). In embodiments, the platinum is conjugated directly to the Si atom thereby forming a —Si—Pt— bond. In embodiments, the platinum is conjugated directly to one or more Si atoms. In embodiments, the platinum is conjugated to the Si atom via an oxygen linker thereby forming a —Si—O—Pt— bond. In embodiments, the platinum is conjugated to the Si atom via one or more oxygen linkers. In embodiments, the platinum is conjugated to the Si atom via a nitrogen linker thereby forming a —Si—NH—Pt— bond. In embodiments, the platinum is conjugated to the Si atom via one or more a nitrogen linkers. In embodiments, the platinum anti-cancer agent is conjugated to an oxygen donor within the silica nanoparticle. In embodiments, the platinum anti-cancer agent is conjugated to one or more oxygen donors within the silica nanoparticle. In embodiments, the platinum anti-cancer agent is not conjugated to the silica nanoparticle via an aminosilane moiety (e.g., (3-aminopropyl) triethoxysilane). In embodiments, the platinum anti-cancer agent is not conjugated to the silica nanoparticle via an ester, aminoalkyl, urea, thiourea, or thioether group.

In embodiments, the platinum atom of the platinum anti-cancer agent (e.g., platinum salt or cisplatin) within the silica nanoparticle is directly bonded to one or more oxygen donors within the silica nanoparticle (e.g. an oxygen of a silicon-oxygen moiety within the silica nanoparticle), having the formula:

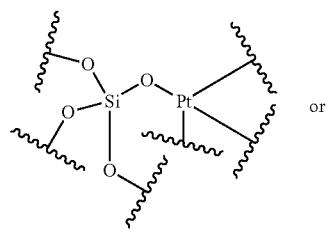 or

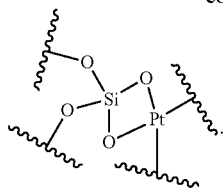

In embodiments, the silica nanoparticle is an unmodified silica nanoparticle. In embodiments, the silica nanoparticle is a non-polymeric functionalized silica nanoparticle (i.e. a silica nanoparticle that does not include polymers conjugated to the surface of the silica nanoparticle). In embodiments, the silica nanoparticle is a non-pegylated functionalized silica nanoparticle (i.e. a silica nanoparticle that does not include PEG polymers conjugated to the surface of the silica nanoparticle). In embodiments, the silica nanoparticle is a non-functionalized silica nanoparticle (i.e. a silica nanoparticle that does not include reactive chemical functional groups, such as a bioconjugate reactive group, conjugated to the surface of the silica nanoparticle (other than the terminal hydroxyl groups).

In embodiments, the unmodified silica nanoparticle includes terminal oxygen atoms (e.g., the oxygens on the surface of the nanoparticle) that are hydroxyl moieties. In embodiments, the terminal oxygen atoms of the unmodified silica nanoparticle are —OH or salts thereof (e.g. —O⁻ moieties). In embodiments, the terminal oxygen atoms of the unmodified silica nanoparticle may include an —OR" moiety, wherein R" is a substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl or substituted (e.g., substituted with a substituent group, a size-limited substituent group, or lower substituent group) or unsubstituted heteroaryl. In embodiments, about 70%, 80%, 90%, 95%, 99%, or about 100% of the terminal oxygen atoms of the unmodified silica nanoparticle are hydroxyl moieties (or salts thereof). In embodiments, about 90%, 91%, 92%, 93%, 94%, 95%, 96%, 97%, 98%, 99%, 99.9%, or about 100% of the terminal oxygen atoms of the unmodified silica nanoparticle are hydroxyl moieties (or salts thereof). In embodiments, the unmodified silica nanoparticle does not include a covalent bond to an additional chemical moiety (e.g., platinum anti-cancer agent). In embodiments, the unmodified silica nanoparticle includes a covalent bond to an additional chemical moiety (e.g., platinum anti-cancer agent). In embodiments, once the unmodified silica nanoparticle has formed, no further chemistry is performed to attach an additional chemical moiety (e.g., platinum anti-cancer agent) to the surface of the nanoparticle.

In embodiments, the platinum anti-cancer agent is incorporated (e.g., covalently or non-covalently) within the silica nanoparticle. In embodiments, the platinum anti-cancer agent is incorporated (e.g., covalently or non-covalently) throughout the silica nanoparticle (e.g., evenly distributed throughout the silica nanoparticle, distributed throughout the silica nanoparticle (e.g. in varying local concentrations), distributed within +/−10, 20, 30, 40, 50, 60, 70, 80, 90, or 100% of the average local concentration). In embodiments, the platinum anti-cancer agent is distributed within about 10, 20, 30, 40, 50, 60, 70, 80, 90, or 100% of the average local concentration. In embodiments, the platinum anti-cancer agent is conjugated to the surface and within the silica nanoparticle. In embodiments, the platinum anti-cancer agent is at the surface of the silica nanoparticle (e.g., bonded covalently or non-covalently). In embodiments, the cisplatin is encapsulated within the silica nanoparticle (e.g., a particle of cisplatin within the nanoparticle (e.g., a particle of greater than 60, 70, 80, 90, 91, 92, 93, 94, 95, 96, 97, 98, or 99% cisplatin or a particle of about 100% cisplatin)). In embodiments, the cisplatin is encapsulated within the silica nanoparticle and at the surface.

In embodiments, the platinum anti-cancer agent is not modified prior to incorporation into the silica nanoparticle (an "unmodified platinum anti-cancer agent"). For example, cisplatin may be incorporated into the silica nanoparticle in an unmodified form as (SP-4-2)-diamminedicholoroplatinum(II) (e.g,

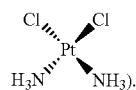

During or subsequent to the incorporation process, the cisplatin may react with a portion of the silica nanoparticle. For example, one or more Pt ligands (e.g., —Cl) of cisplatin may be replaced with a bond directly to an oxygen of silica (e.g.,

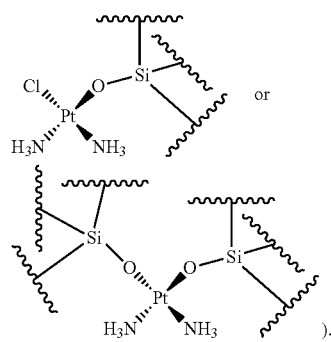

).

Where an unmodified cisplatin is incorporated into the silica nanoparticle herein, the resulting nanoparticle may be referred to as including "unmodified cisplatin" even though the cisplatin may have reacted with a portion of the silica nanoparticle during or subsequent to the incorporation process. Thus, in embodiments, the silica nanoparticle includes a platinum anti-cancer agent (e.g., unmodified platinum anti-cancer agent) such as an unmodified cisplatin.

In embodiments, the platinum anti-cancer agent is cisplatin, carboplatin, oxaliplatin, satraplatin, lobaplatin, picoplatin, heptaplatin, nedaplatin, or triplatin. In embodiments, the platinum anti-cancer agent is cisplatin. In embodiments, the cisplatin is directly conjugated to the silica nanoparticle. In embodiments, the platinum anti-cancer agent is carboplatin. In embodiments, the platinum anti-cancer agent is oxaliplatin. In embodiments, the platinum anti-cancer agent is satraplatin. In embodiments, the platinum anti-cancer agent is lobaplatin. In embodiments, the platinum anti-cancer agent is picoplatin. In embodiments, the platinum anti-cancer agent is heptaplatin. In embodiments, the platinum anti-cancer agent is nedaplatin. In embodiments, the platinum anti-cancer agent is triplatin. In embodiments, the ligands of the platinum anti-cancer agent optionally replaced with water. In embodiments, the ligands of the platinum anti-cancer agent optionally replaced with an oxygen (e.g., an oxygen bound to silica) in the nanoparticle.

In embodiments, the platinum anti-cancer agent is a platinum salt. In embodiments, the platinum anti-cancer agent is $PtX_4$, wherein X is a halogen. In embodiments, the platinum anti-cancer agent is $PtCl_4$. In embodiments, the platinum anti-cancer agent is $[A_2]PtX_2$, wherein X is a halogen and A is a cation (e.g., potassium or sodium). In embodiments, the platinum anti-cancer agent is $PtX_2$, wherein X is a halogen. In embodiments, the platinum anti-cancer agent is $Pt(Cl)_2$. In embodiments, the platinum anti-cancer agent is $Pt(CN)_2$. In embodiments, the platinum anti-cancer agent is ammonium hexachloroplatinate, ammonium tetrachloroplatinate, potassium trichloro(ethylene)platinate(II) hydrate, Zeise's salt, or hexachloroplatinic acid. In embodiments, the platinum anti-cancer agent is [Pt(NH$_3$)$_4$]Cl$_2$, K$_2$[Pt(NO$_2$)$_4$], or platinum nitrate.

In embodiments, the silica:platinum mass ratio is about 10:1 to 100:1. In embodiments, the silica:platinum mass ratio is about 10:1 to 90:1. In embodiments, the silica:platinum mass ratio is about 10:1 to 80:1. In embodiments, the silica:platinum mass ratio is about 10:1 to 70:1. In embodiments, the silica:platinum mass ratio is about 10:1 to 60:1. In embodiments, the silica:platinum mass ratio is about 10:1 to 50:1.

In embodiments, the silica:platinum mass ratio is about 10:1 to 40:1. In embodiments, the silica:platinum mass ratio is about 11:1. In embodiments, the silica:platinum mass ratio is about 12:1. In embodiments, the silica:platinum mass ratio is about 13:1. In embodiments, the silica:platinum mass ratio is about 14:1. In embodiments, the silica:platinum mass ratio is about 15:1. In embodiments, the silica:platinum mass ratio is about 16:1. In embodiments, the silica:platinum mass ratio is about 17:1. In embodiments, the silica:platinum mass ratio is about 18:1. In embodiments, the silica:platinum mass ratio is about 19:1. In embodiments, the silica:platinum mass ratio is about 20:1. In embodiments, the silica:platinum mass ratio is about 21:1. In embodiments, the silica:platinum mass ratio is about 22:1. In embodiments, the silica:platinum mass ratio is about 23:1. In embodiments, the silica:platinum mass ratio is about 24:1. In embodiments, the silica:platinum mass ratio is about 25:1. In embodiments, the silica:platinum mass ratio is about 26:1. In embodiments, the silica:platinum mass ratio is about 27:1. In embodiments, the silica:platinum mass ratio is about 28:1. In embodiments, the silica:platinum mass ratio is about 29:1. In embodiments, the silica:platinum mass ratio is about 30:1. In embodiments, the silica:platinum mass ratio is about 31:1. In embodiments, the silica:platinum mass ratio is about 32:1. In embodiments, the silica:platinum mass ratio is about 33:1. In embodiments, the silica:platinum mass ratio is about 34:1. In embodiments, the silica:platinum mass ratio is about 35:1. In embodiments, the silica:platinum mass ratio is about 36:1. In embodiments, the silica:platinum mass ratio is about 37:1. In embodiments, the silica:platinum mass ratio is about 38:1. In embodiments, the silica:platinum mass ratio is about 39:1. In embodiments, the silica:platinum mass ratio is about 40:1.

In embodiments, the average longest dimension of the nanoparticle is from about 10 nm to about 1000 nm. In embodiments, the average longest dimension of the nanoparticle is from about 10 nm to about 900 nm. In embodiments, the average longest dimension of the nanoparticle is from about 10 nm to about 800 nm. In embodiments, the average longest dimension of the nanoparticle is from about 10 nm to about 700 nm. In embodiments, the average longest dimension of the nanoparticle is from about 100 nm to about 400 nm. In embodiments, the average longest dimension of the nanoparticle is from about 200 nm to about 500 nm. In embodiments, the average longest dimension of the nanoparticle is from about 300 nm to about 500 nm. In embodiments, the average longest dimension of the nanoparticle is from about 500 nm to about 1000 nm. In embodiments, the average longest dimension of the nanoparticle is from about 400 nm to about 800 nm.

In embodiments, the average longest dimension of the nanoparticle is from about 10 nm to about 600 nm. In embodiments, the average longest dimension of the nanoparticle is from about 10 nm to about 300 nm. In embodiments, the average longest dimension of the nanoparticle is from about 10 nm to about 100 nm. In embodiments, the average longest dimension of the nanoparticle is from about 10 nm to about 90 nm. In embodiments, the average longest dimension of the nanoparticle is from about 10 nm to about 80 nm. In embodiments, the average longest dimension of the nanoparticle is from about 10 nm to about 70 nm. In embodiments, the average longest dimension of the nanoparticle is from about 10 nm to about 60 nm. In embodiments, the average longest dimension of the nanoparticle is from about 10 nm to about 50 nm. In embodiments, the average longest dimension of the nanoparticle is from about 25 nm to about 75 nm. In embodiments, the average longest dimension of the nanoparticle is from about 40 nm to about 60 nm. In embodiments, the average longest dimension of the nanoparticle is from about 45 nm to about 55 nm. In embodiments, the average longest dimension of the nanoparticle is about 51 nm.

In embodiments, the average longest dimension of the nanoparticle is from about 200 nm to about 250 nm. In embodiments, the average longest dimension of the nanoparticle is from about 400 nm to about 600 nm. In embodiments, the average longest dimension of the nanoparticle is from about 430 nm to about 530 nm.

In embodiments, the average longest dimension of the nanoparticle is from about 100 nm to about 400 nm. In embodiments, the average longest dimension of the nanoparticle is about 170 nm to 270 nm. In embodiments, the average longest dimension of the nanoparticle is about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the average longest dimension of the nanoparticle is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the average longest dimension of the nanoparticle is less than about 1000 nm. In embodiments, the average longest dimension of the nanoparticle is less than about 900 nm. In embodiments, the average longest dimension of the nanoparticle is less than about 800 nm. In embodiments, the average longest dimension of the nanoparticle is less than about 700 nm. In embodiments, the average longest dimension of the nanoparticle is less than about 600 nm. In embodiments, the average longest dimension of the nanoparticle is less than about 500 nm. In embodiments, the average longest dimension of the nanoparticle is less than about 400 nm. In embodiments, the average longest dimension of the nanoparticle is less than about 300 nm. In embodiments, the average longest dimension of the nanoparticle is less than about 200 nm. In embodiments, the average longest dimension of the nanoparticle is less than about 100 nm. In embodiments, the average longest dimension of the nanoparticle is less than about 90 nm. In embodiments, the average longest dimension of the nanoparticle is less than about 80 nm. In embodiments, the average longest dimension of the nanoparticle is less than about 70 nm. In embodiments, the average longest dimension of the nanoparticle is less than about 60 nm. In embodiments, the average longest dimension of the nanoparticle is less than about 50 nm. In embodiments, the average longest dimension of the nanoparticle is less than about 40 nm. In embodiments, the average longest dimension of the nanoparticle is less than about 30 nm. In embodiments, the average longest dimension of the nanoparticle is less than about 20 nm. In embodiments, the average longest dimension of the nanoparticle is less than about 10 nm.

In embodiments, the average longest dimension of the nanoparticle is less than about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the average longest dimension of the nanoparticle is less than about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the average longest dimension of the nanoparticle is less than 1000 nm. In embodiments, the average longest dimension of the nanoparticle is less than 900 nm. In embodiments, the average longest dimension of the nanoparticle is less than 800 nm. In embodiments, the average longest dimension of the nanoparticle is less than 700 nm. In embodiments, the average longest dimension of the nanoparticle is less than 600 nm. In embodiments, the average longest dimension of the nanoparticle is less than 500 nm. In embodiments, the average longest dimension of the nanoparticle is less than 400 nm. In embodiments, the average longest dimension of the nanoparticle is less than 300 nm. In embodiments, the average longest dimension of the nanoparticle is less than 200 nm. In embodiments, the average longest dimension of the nanoparticle is less than 100 nm. In embodiments, the average longest dimension of the nanoparticle is less than 90 nm. In embodiments, the average longest dimension of the nanoparticle is less than 80 nm. In embodiments, the average longest dimension of the nanoparticle is less than 70 nm. In embodiments, the average longest dimension of the nanoparticle is less than 60 nm. In embodiments, the average longest dimension of the nanoparticle is less than 50 nm. In embodiments, the average longest dimension of the nanoparticle is less than 40 nm. In embodiments, the average longest dimension of the nanoparticle is less than 30 nm. In embodiments, the average longest dimension of the nanoparticle is less than 20 nm. In embodiments, the average longest dimension of the nanoparticle is less than 10 nm.

In embodiments, the average longest dimension of the nanoparticle is less than 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average shortest dimension of the nanoparticle is about 10 nm.

In embodiments, the average longest dimension of the nanoparticle is less than 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the nanoparticle further includes a detectable compound. In embodiments, the unmodified silica nanoparticle includes a detectable compound. In embodiments, the detectable compound is a radioisotope, fluorophore, electron-dense reagent, enzyme, biotin, paramagnetic agent, or magnetic agent. In embodiments, the detectable compound is a radioisotope. In embodiments, the detectable compound is a fluorophore. In embodiments, the detectable compound includes cyanine, heptamethine, xanthene, rhodamine, fluorescein, boron-dipyrromethene, boron dipyridyl, naphthalene, coumarin, acridine, acridinium, tetrapyrrole, tetraphenylethene, oxazine, pyrene, oxadiazole, subphthalocyanine, carbopyrinin, benzopyrinium, or phthalocyanine. In embodiments, the fluorophore is indocyanine green or a coumarin dye. In embodiments, the detectable agent is indocyanine green. In embodiments, the fluorophore is an FDA approved dye for clinical use. In embodiments, the fluorophore has a low toxicity profile. One skilled in the art would recognize that common fluorescent proteins or non-protein organic fluorophores may be examples of a detectable compound.

In an aspect is provided a cell including a nanoparticle (e.g., a silica nanoparticle) described herein. In embodiments, the cell is a tumor tropic cell, macrophage, stem cell (e.g., neural, mesenchymal), or T-cell. In embodiments, the cell is neural stem cell, a mesenchymal stem cell, a mesenchymal stromal cell, a hematopoetic stem cell, T-lymphocyte, a macrophage, or a liver stem cell. In embodiments, the cell is a neural stem cell. In embodiments, the cell is genetically modified. In embodiments, the cell is a genetically modified stem cell. In embodiments, the cell is a genetically modified neural stem cell. In embodiments, the neural stem cell is a human HB1.F3 stem cell. In embodiments, the nanoparticle is within the cell. In embodiments, the nanoparticle is incorporated within the cell via the enhanced permeability and retention (EPR) effect.

In an aspect is provided a nanoparticle-cell construct including a nanoparticle covalently attached to a protein (e.g., a cell-surface protein) through a covalent linker. In embodiments, the protein is attached to cell and is a cell surface protein. In embodiments, the protein includes a sulfur-containing amino acid. In embodiments, the protein includes methionine, cysteine, homocysteine, or taurine. In embodiments, the protein includes a sulfhydryl moiety. In embodiments of the nanoparticle-cell construct, the nanoparticle is a silica nanoparticle. In embodiments of the nanoparticle-cell construct, the nanoparticle is a silica nanoparticle which further comprises a platinum anti-cancer agent.

In embodiments of the nanoparticle-cell construct, the nanoparticle is an inorganic nanoparticle. In embodiments of the nanoparticle-cell construct, the nanoparticle is a silica nanoparticle. The inorganic nanoparticle may be a metal nanoparticle. The metal of the metal nanoparticle may be in the form of a metal oxide and the metal nanoparticle a metal oxide nanoparticle. The metal oxide nanoparticle may be titanium oxide or zirconium oxide. In embodiments, the nanoparticle is a gold nanoparticle. In embodiments, the nanoparticle is an iron nanoparticle. In embodiments, the nanoparticle is an iron oxide nanoparticle.

In embodiments, the protein is a cell surface protein. A cell surface protein refers to a protein at the surface of a protein. In embodiments, the cell surface protein is a transmembrane protein. In embodiments the protein is in contact with the extracellular matrix (e.g., extracellular matrix associated with a cancer cell or in contact with a cancer cell). In embodiments, the protein is in contact with a tumor. In embodiments, the tumor includes stromal cells, immune cells, proteins, and extracellular matrix generated by those cells. In embodiments, immune cells, stromal cells, proteins associate with the immune cells, proteins associated with the stromal cells, and the extracellular matrix generated from immune cells and stromal cells forms part of a tumor.

In embodiments, the covalent linker has the formula: -$L^2$-$X^1$-$L^1$-$X^2$-$L^3$- (Ia) or -$L^2$-$X^2$-$L^3$- (Ib). $X^1$ and $X^2$ are independently a bioconjugate linker or a bond, wherein one of $X^1$ or $X^2$ is a bioconjugate linker. L is independently a polymeric linker. $L^2$ is independently a bond, —$NR^{1a}$—, —O—, —S—, —C(O)—, —C(O)O—, —S(O)—, —S(O)_2$—, —$NR^{1a}$C(O)—, —C(O)$NR^{1b}$—, —C(O)(CH$_2$)$_{z1}$—, —$NR^{1a}$C(O)O—, —$NR^{1a}$C(O)$NR^{1b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^3$ is independently a bond, —$NR^{2a}$—, —O—, —S—, —C(O)—, —C(O)O—, —S(O)—, —S(O)_2$—, —$NR^{2a}$C(O)—, —C(O)$NR^{2b}$—, —C(O)(CH$_2$)$_{z2}$—, —$NR^{2a}$C(O)O—, —$NR^{2a}$C(O)$NR^{2b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{1a}$, $R^{2a}$, $R^{1b}$, and $R^{2b}$ are independently hydrogen, halogen, —$CF_3$, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC=(O)$NHNH_2$, —NHC=(O)$NH_2$, —$NHSO_2$H, —NHC=(O)H, —NHC(O)OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; the symbols z1 and z2 are independently an integer from 1 to 10. In embodiments, $R^{1a}$, $R^{2a}$, $R^{1b}$, and $R^{2b}$ are independently hydrogen, halogen, —$CF_3$, —CN, —OH, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; the symbols z1 and z2 are independently an integer from 1 to 10. In formula (Ib), $X^2$ is a bioconjugate linker. In embodiments of the nanoparticle-cell construct, the polymeric linker does not include poly(lactate)-poly(ethylene glycol) copolymer, poly (β-amino ester), poly(lactate), poly(ethylene glycol)-dimethacrylate, or methyl ether poly(ethylene glycol)-poly(3-amino ester) copolymer. In embodiments, $X^1$ or $X^2$ independently do not include biotin. In embodiments, -$L^2$-$X^1$-$L^1$-$X^2$-$L^3$- or -$L^2$-$X^2$-$L^3$- does not include biotin. In embodiments, -$L^2$-$X^1$-$L^1$-$X^2$-$L^3$- and -$L^2$-$X^2$-$L^3$- does not include biotin. In embodiments, the silica nanoparticle does not include biotin.

In embodiments, $L^2$ has the formula -$L^{2A}$-$L^{2B}$-. $L^{2A}$ and $L^{2B}$ are independently a bond, —$NR^{1a}$—, —O—, —S—, —C(O)—, —C(O)O—, —S(O)—, —S(O)$_2$—, —NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L$^{2A}$ is a substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, L$^{2B}$ is a substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, L$^{2A}$ and L$^{2B}$ are independently an unsubstituted alkylene, unsubstituted heteroalkylene, unsubstituted cycloalkylene, unsubstituted heterocycloalkylene, unsubstituted arylene, or unsubstituted heteroarylene.

In embodiments, the nanoparticle is further covalently attached to one or more nanoparticle substituents. In embodiments, the nanoparticle substituent includes a polymeric moiety. In embodiments, the polymeric moiety is a polyethylene glycol moiety.

In embodiments, the nanoparticle substituent is: -L$^2$-X$^1$—R$^3$ (i); -L$^2$-X$^1$-L$^1$-X$^3$ (ii); or -L$^2$-X$^3$ (iii). L$^1$, L$^2$, X$^1$, L$^1$ and X$^3$ are as defined below and are optionally different. R$^3$ is independently a polymeric moiety. X$^3$ is independently a bioconjugate reactive group. In embodiments, one or more of L$^1$, L$^2$, X$^1$, L$^1$ and X$^3$ are the same.

In embodiments, L$^1$ is a linear polymeric linker. In embodiments, L$^1$ is a branched polymeric linker. In embodiments, a nanoparticle includes multiple, optionally different, L$^1$ linkers and each L$^1$ linker is independently a linear or branched polymeric linker. In embodiments, L$^1$ is branched with 3 to 10 branches. In embodiments, when L$^1$ is branched, there is one bioconjugate reactive group. In embodiments, when L$^1$ is branched there is a plurality of bioconjugate reactive groups.

In embodiments, L$^1$ is polyethylene glycol. In embodiments, L$^1$ is divalent -PEG$_{400}$-SH. In embodiments, L$^1$ is divalent -PEG$_{1000}$-SH. In embodiments, L$^1$ is divalent -PEG$_{2000}$-SH. In embodiments, L$^1$ is divalent -PEG$_{5000}$-SH.

It will be understood that the immediately preceding divalent PEG-SH groups may be bonded to a separate moiety through the terminal thiol group where the bond between sulfur and hydrogen is replaced with a bond between sulfur and another moiety. In embodiments, L$^1$ is divalent -TFP-(PEG$_{11}$)$_3$. It will be understood that the immediately preceding divalent TFP-PEG groups may be bonded to a separate moiety through the tetrafluorophenyl (TFP) ester group wherein the bond is between the tetrafluorophenyl ester and another moiety. In embodiments, L$^1$ is divalent NHS-(PEG$_{24}$)$_3$. It will be understood that the immediately preceding divalent NSH-PEG groups may be bonded to a separate moiety through the N-hydroxysuccinimide group where the bond is between N-hydroxysuccinimide and another moiety. In embodiments, L$^1$ is polyethylene glycol with an average molecular weight of about 400 g/mol, 484 g/mol, 1000 g/mol, 1450 g/mol, 1500 g/mol, 2000 g/mol, or 5000 g/mol. In embodiments, L$^1$ is polyethylene glycol with an average molecular weight of about 400 g/mol, 484 g/mol, 1000 g/mol, 1450 g/mol, 1500 g/mol, 2000 g/mol, or 5000 g/mol within +/−10, 20, 30, 40, or 50 of the average molecular weight.

In embodiments, L$^1$ is polyethylene glycol with an average molecular weight of about 400 g/mol. In embodiments, L$^1$ is polyethylene glycol with an average molecular weight of about 484 g/mol. In embodiments, L$^1$ is polyethylene glycol with an average molecular weight of about 484 g/mol per arm. In embodiments, L$^1$ is polyethylene glycol with an average molecular weight of about 1000 g/mol. In embodiments, L$^1$ is polyethylene glycol with an average molecular weight of about 1450 g/mol. In embodiments, L$^1$ is polyethylene glycol with an average molecular weight of about 1500 g/mol. In embodiments, L$^1$ is polyethylene glycol with an average molecular weight of about 2000 g/mol. In embodiments, L$^1$ is polyethylene glycol with an average molecular weight of about 5000 g/mol.

In embodiments, L$^1$ is a polymeric linker further including substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L$^1$ is a polymeric linker further comprising unsubstituted alkylene, unsubstituted heteroalkylene, unsubstituted cycloalkylene, unsubstituted heterocycloalkylene, unsubstituted arylene, or unsubstituted heteroarylene. In embodiments, L$^1$ is a polymeric linker further including unsubstituted alkylene, unsubstituted heteroalkylene, unsubstituted cycloalkylene, unsubstituted heterocycloalkylene, unsubstituted arylene, or unsubstituted heteroarylene.

In embodiments, L$^2$ is independently a bond, —NR$^{1a}$—, —O—, —S—, —C(O)—, —C(O)O—, —S(O)—, —S(O)$_2$—, —NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$—, substituted or unsubstituted alkylene (e.g. C$_1$-C$_8$ alkylene, C$_1$-C$_6$ alkylene, or C$_1$-C$_4$ alkylene), substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), substituted or unsubstituted cycloalkylene (e.g. C$_3$-C$_8$ cycloalkylene, C$_4$-C$_8$ cycloalkylene, or C$_5$-C$_6$ cycloalkylene), substituted or unsubstituted heterocycloalkylene (e.g. 3 to 8 membered heterocycloalkylene, 4 to 8 membered heterocycloalkylene, or 5 to 6 membered heterocycloalkylene), substituted or unsubstituted arylene (e.g. C$_6$-C$_{10}$ arylene or C$_6$ arylene), or substituted or unsubstituted heteroarylene (e.g. 5 to 10 membered heteroarylene, 5 to 9 membered heteroarylene, or 5 to 6 membered heteroarylene).
In embodiments, $L^2$ has the formula:
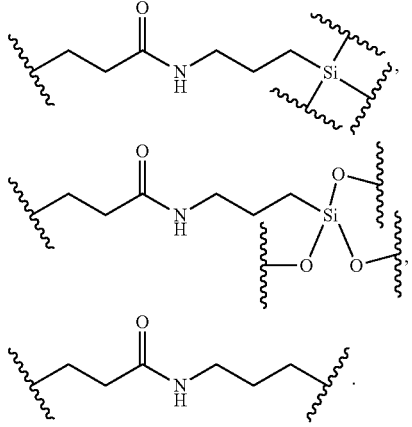
In embodiments, $L^2$ has the formula:
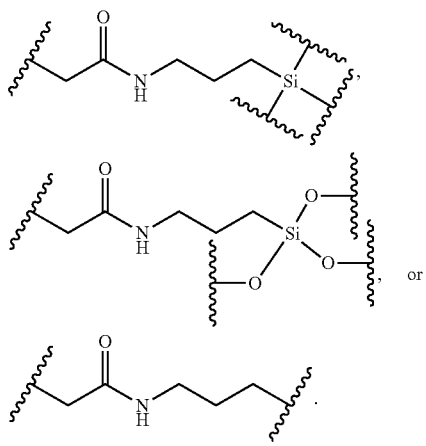
In embodiments, $L^2$ has the formula:
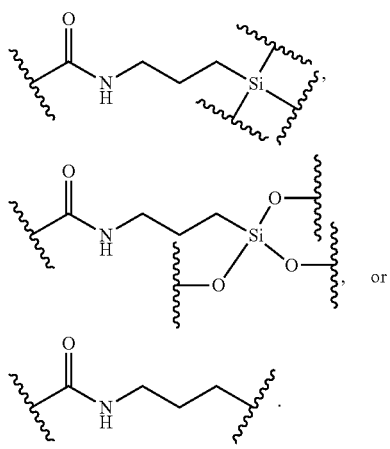
In embodiments, $L^2$ has the formula:
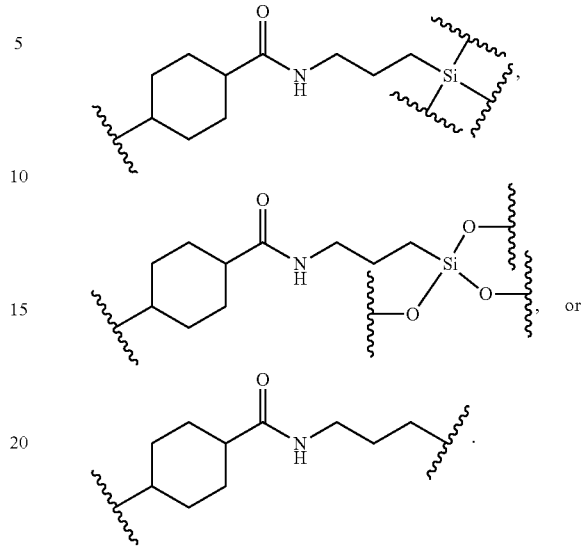
In embodiments, $L^2$ has the formula:
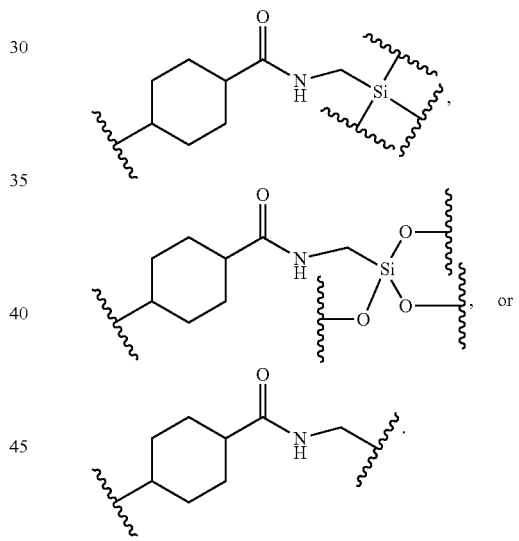
In embodiments, $L^2$ has the formula:
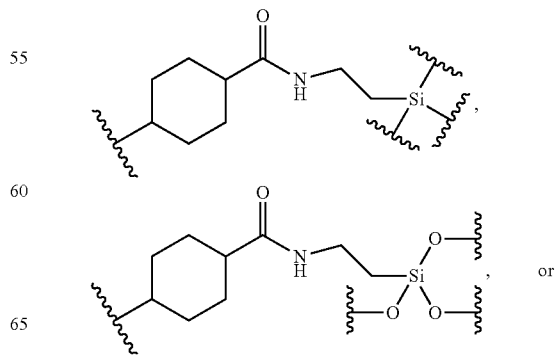

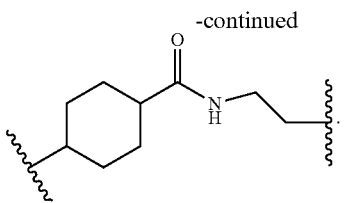

In embodiments, L² has the formula:

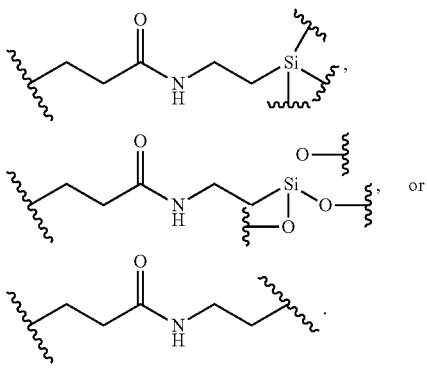

In embodiments, L² is independently a bond, —NR¹ᵃ—, —O—, —S—, —C(O)—, —C(O)O—, —S(O)—, —S(O)₂—, —NR¹ᵃC(O)—, —C(O)NR¹ᵇ—, —C(O)(CH₂)$_{z1}$—, —NR¹ᵃC(O)O—, —NR¹ᵃC(O)NR¹ᵇ—, R⁴-substituted or unsubstituted alkylene (e.g. C₁-C₈ alkylene, C₁-C₆ alkylene, or C₁-C₄ alkylene), R⁴-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), R⁴-substituted or unsubstituted cycloalkylene (e.g. C₃-C₈ cycloalkylene, C₄-C₈ cycloalkylene, or C₅-C₆ cycloalkylene), R⁴-substituted or unsubstituted heterocycloalkylene (e.g. 3 to 8 membered heterocycloalkylene, 4 to 8 membered heterocycloalkylene, or 5 to 6 membered heterocycloalkylene), R⁴-substituted or unsubstituted arylene (e.g. C₆-C₁₀ arylene or C₆ arylene), or R⁴-substituted or unsubstituted heteroarylene (e.g. 5 to 10 membered heteroarylene, 5 to 9 membered heteroarylene, or 5 to 6 membered heteroarylene). In embodiments, L² is independently a bond, —NR¹ᵃ—, —O—, —S—, —C(O)—, —C(O)O—, —S(O)—, —S(O)₂—, —NR¹ᵃC(O)—, —C(O)NR¹ᵇ—, —C(O)(CH₂)$_{z1}$—, —NR¹ᵃC(O)O—, —NR¹ᵃC(O)NR¹ᵇ—, Unsubstituted alkylene (e.g. C₁-C₈ alkylene, C₁-C₆ alkylene, or C₁-C₄ alkylene), unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), unsubstituted cycloalkylene (e.g. C₃-C₈ cycloalkylene, C₄-C₈ cycloalkylene, or C₅-C₆ cycloalkylene), unsubstituted heterocycloalkylene (e.g. 3 to 8 membered heterocycloalkylene, 4 to 8 membered heterocycloalkylene, or 5 to 6 membered heterocycloalkylene), unsubstituted arylene (e.g. C₆-C₁₀ arylene or C₆ arylene), or unsubstituted heteroarylene (e.g. 5 to 10 membered heteroarylene, 5 to 9 membered heteroarylene, or 5 to 6 membered heteroarylene). In embodiments, L² is independently a bond, —NR¹ᵃ—, —O—, —S—, —C(O)—, —C(O)O—, —S(O)—, —S(O)₂—, —NR¹ᵃC(O)—, —C(O)NR¹ᵇ—, —C(O)(CH₂)$_{z1}$—, —NR¹ᵃC(O)O—, —NR¹ᵃC(O)NR¹ᵇ—, unsubstituted alkylene (e.g. C₁-C₈ alkylene, C₁-C₆ alkylene, or C₁-C₄ alkylene), unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), unsubstituted cycloalkylene (e.g. C₃-C₈ cycloalkylene, C₄-C₈ cycloalkylene, or C₅-C₆ cycloalkylene), unsubstituted heterocycloalkylene (e.g. 3 to 8 membered heterocycloalkylene, 4 to 8 membered heterocycloalkylene, or 5 to 6 membered heterocycloalkylene), unsubstituted arylene (e.g. C₆-C₁₀ arylene or C₆ arylene), or unsubstituted heteroarylene (e.g. 5 to 10 membered heteroarylene, 5 to 9 membered heteroarylene, or 5 to 6 membered heteroarylene).

R⁴ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, R⁵-substituted or unsubstituted alkyl (e.g. C₁-C₈ alkyl, C₁-C₆ alkyl, or C₁-C₄ alkyl), R⁵-substituted or unsubstituted heteroalkyl (e.g. 2 to 8 membered heteroalkyl, 2 to 6 membered heteroalkyl, or 2 to 4 membered heteroalkyl), R⁵-substituted or unsubstituted cycloalkyl (e.g. C₃-C₈ cycloalkyl, C₄-C₈ cycloalkyl, or C₅-C₆ cycloalkyl), R⁵-substituted or unsubstituted heterocycloalkyl (e.g. 3 to 8 membered heterocycloalkyl, 4 to 8 membered heterocycloalkyl, or 5 to 6 membered heterocycloalkyl), R⁵-substituted or unsubstituted aryl (e.g. C₆-C₁₀ aryl or C₆ aryl), or R⁵-substituted or unsubstituted heteroaryl (e.g. 5 to 10 membered heteroaryl, 5 to 9 membered heteroaryl, or 5 to 6 membered heteroaryl).

In embodiments, L³ is independently a bond, —NR²ᵃ—, —O—, —S—, —C(O)—, —C(O)O—, —S(O)—, —S(O)₂—, —NR²ᵃC(O)—, —C(O)NR²ᵇ—, —C(O)(CH₂)$_{z2}$—, —NR²ᵃC(O)O—, —NR²ᵃC(O)NR²ᵇ—, substituted or unsubstituted alkylene (e.g. C₁-C₈ alkylene, C₁-C₆ alkylene, or C₁-C₄ alkylene), substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), substituted or unsubstituted cycloalkylene (e.g. C₃-C₈ cycloalkylene, C₄-C₈ cycloalkylene, or C₅-C₆ cycloalkylene), substituted or unsubstituted heterocycloalkylene (e.g. 3 to 8 membered heterocycloalkylene, 4 to 8 membered heterocycloalkylene, or 5 to 6 membered heterocycloalkylene), substituted or unsubstituted arylene (e.g. C₆-C₁₀ arylene or C₆ arylene), or substituted or unsubstituted heteroarylene (e.g. 5 to 10 membered heteroarylene, 5 to 9 membered heteroarylene, or 5 to 6 membered heteroarylene).

In embodiments, L³ is independently a bond, —NR²ᵃ—, —O—, —S—, —C(O)—, —C(O)O—, —S(O)—, —S(O)₂—, —NR²ᵃC(O)—, —C(O)NR²ᵇ—, —C(O)(CH₂)$_{z2}$—, —NR²ᵃC(O)O—, —NR²ᵃC(O)NR²ᵇ—, R⁶-substituted or unsubstituted alkylene (e.g. C₁-C₈ alkylene, C₁-C₆ alkylene, or C₁-C₄ alkylene), R⁶-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), R⁶-substituted or unsubstituted cycloalkylene (e.g. C₃-C₈ cycloalkylene, C₄-C₈ cycloalkylene, or C₅-C₆ cycloalkylene), R⁶-substituted or unsubstituted heterocycloalkylene (e.g. 3 to 8 membered heterocycloalkylene, 4 to 8 membered heterocycloalkylene, or 5 to 6 membered heterocycloalkylene), R⁶-substituted or unsubstituted arylene (e.g. C₆-C₁₀ arylene or C₆ arylene), or $R^6$-substituted or unsubstituted heteroarylene (e.g. 5 to 10 membered heteroarylene, 5 to 9 membered heteroarylene, or 5 to 6 membered heteroarylene).

$R^6$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, $R^7$-substituted or unsubstituted alkyl (e.g. $C_1$-$C_8$ alkyl, $C_1$-$C_6$ alkyl, or $C_1$-$C_4$ alkyl), $R^7$-substituted or unsubstituted heteroalkyl (e.g. 2 to 8 membered heteroalkyl, 2 to 6 membered heteroalkyl, or 2 to 4 membered heteroalkyl), $R^7$-substituted or unsubstituted cycloalkyl (e.g. $C_3$-$C_8$ cycloalkyl, $C_4$-$C_8$ cycloalkyl, or $C_5$-$C_6$ cycloalkyl), $R^7$-substituted or unsubstituted heterocycloalkyl (e.g. 3 to 8 membered heterocycloalkyl, 4 to 8 membered heterocycloalkyl, or 5 to 6 membered heterocycloalkyl), $R^7$-substituted or unsubstituted aryl (e.g. $C_6$-$C_{10}$ aryl or $C_6$ aryl), or $R^7$-substituted or unsubstituted heteroaryl (e.g. 5 to 10 membered heteroaryl, 5 to 9 membered heteroaryl, or 5 to 6 membered heteroaryl).

$R^5$ and $R^7$ are independently oxo, halogen, —F, —Cl, —Br, —I, —$CF_3$, —$CCl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^{1a}$, $R^{2a}$, $R^{1b}$, and $R^{2b}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl). In embodiments, $R^{1a}$, $R^{2a}$, $R^{1b}$, and $R^{2b}$ are independently hydrogen, halogen, —$CF_3$, —CN, —OH, —COOH, —$CONH_2$, substituted or unsubstituted alkyl (e.g. $C_1$-$C_8$ alkyl, $C_1$-$C_6$ alkyl, or $C_1$-$C_4$ alkyl), substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), substituted or unsubstituted cycloalkyl (e.g. $C_3$-$C_8$ cycloalkyl, $C_4$-$C_8$ cycloalkyl, or $C_5$-$C_6$ cycloalkyl), substituted or unsubstituted heterocycloalkyl (e.g. 3 to 8 membered heterocycloalkyl, 4 to 8 membered heterocycloalkyl, or 5 to 6 membered heterocycloalkyl), substituted or unsubstituted aryl (e.g. $C_6$-$C_{10}$ aryl or $C_6$ aryl), or substituted or unsubstituted heteroaryl (e.g. 5 to 10 membered heteroaryl, 5 to 9 membered heteroaryl, or 5 to 6 membered heteroaryl).

In embodiments, $R^{1a}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^8$-substituted or unsubstituted alkyl (e.g. $C_1$-$C_8$ alkyl, $C_1$-$C_6$ alkyl, or $C_1$-$C_4$ alkyl), $R^8$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^8$-substituted or unsubstituted cycloalkyl (e.g. $C_3$-$C_5$ cycloalkyl, $C_4$-$C_8$ cycloalkyl, or $C_5$-$C_6$ cycloalkyl), $R^8$-substituted or unsubstituted heterocycloalkyl (e.g. 3 to 8 membered heterocycloalkyl, 4 to 8 membered heterocycloalkyl, or 5 to 6 membered heterocycloalkyl), $R^8$-substituted or unsubstituted aryl (e.g. $C_6$-$C_{10}$ aryl or $C_6$ aryl), or $R^8$-substituted or unsubstituted heteroaryl (e.g. 5 to 10 membered heteroaryl, 5 to 9 membered heteroaryl, or 5 to 6 membered heteroaryl). In embodiments, $R^{1a}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^8$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^9$-substituted or unsubstituted alkyl (e.g. $C_1$-$C_8$ alkyl, $C_1$-$C_6$ alkyl, or $C_1$-$C_4$ alkyl), $R^9$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^9$-substituted or unsubstituted cycloalkyl (e.g. $C_3$-$C_8$ cycloalkyl, $C_4$-$C_8$ cycloalkyl, or $C_5$-$C_6$ cycloalkyl), $R^9$-substituted or unsubstituted heterocycloalkyl (e.g. 3 to 8 membered heterocycloalkyl, 4 to 8 membered heterocycloalkyl, or 5 to 6 membered heterocycloalkyl), $R^9$-substituted or unsubstituted aryl (e.g. $C_6$-$C_{10}$ aryl or $C_6$ aryl), or $R^9$-substituted or unsubstituted heteroaryl (e.g. 5 to 10 membered heteroaryl, 5 to 9 membered heteroaryl, or 5 to 6 membered heteroaryl).

In embodiments, $R^{1b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^{10}$-substituted or unsubstituted alkyl (e.g. $C_1$-$C_8$ alkyl, $C_1$-$C_6$ alkyl, or $C_1$-$C_4$ alkyl), $R^{10}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{10}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{10}$-substituted or unsubstituted heterocycloalkyl (e.g. 3 to 8 membered heterocycloalkyl, 4 to 8 membered heterocycloalkyl, or 5 to 6 membered heterocycloalkyl), $R^{10}$-substituted or unsubstituted aryl (e.g. $C_6$-$C_{10}$ aryl or $C_6$ aryl), or $R^{10}$-substituted or unsubstituted heteroaryl (e.g. 5 to 10 membered heteroaryl, 5 to 9 membered heteroaryl, or 5 to 6 membered heteroaryl). In embodiments, $R^{1b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{10}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^{11}$-substituted or unsubstituted alkyl (e.g. $C_1$-$C_8$ alkyl, $C_1$-$C_6$ alkyl, or $C_1$-$C_4$ alkyl), $R^{11}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11}$-substituted or unsubstituted aryl (e.g. $C_6$-$C_{10}$ aryl or $C_6$ aryl), or $R^{11}$-substituted or unsubstituted heteroaryl (e.g. 5 to 10 membered heteroaryl, 5 to 9 membered heteroaryl, or 5 to 6 membered heteroaryl).

In embodiments, $R^{2a}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2R^{12}$-substituted or unsubstituted alkyl (e.g. $C_1$-$C_8$ alkyl, $C_1$-$C_6$ alkyl, or $C_1$-$C_4$ alkyl), $R^{12}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{12}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12}$-substituted or unsubstituted aryl (e.g. $C_6$-$C_{10}$ aryl or $C_6$ aryl), or $R^{12}$-substituted or unsubstituted heteroaryl (e.g. 5 to 10 membered heteroaryl, 5 to 9 membered heteroaryl, or 5 to 6 membered heteroaryl). In embodiments, $R^{2a}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{12}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, $R^1$-substituted or unsubstituted alkyl (e.g. $C_1$-$C_8$ alkyl, $C_1$-$C_6$ alkyl, or $C_1$-$C_4$ alkyl), $R^{13}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{13}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13}$-substituted or unsubstituted aryl (e.g. $C_6$-$C_{10}$ aryl or $C_6$ aryl), or $R^{13}$-substituted or unsubstituted heteroaryl (e.g. 5 to 10 membered heteroaryl, 5 to 9 membered heteroaryl, or 5 to 6 membered heteroaryl).

In embodiments, $R^{2b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2R^{14}$-substituted or unsubstituted alkyl (e.g. $C_1$-$C_8$ alkyl, $C_1$-$C_6$ alkyl, or $C_1$-$C_4$ alkyl), $R^{14}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{14}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{14}$-substituted or unsubstituted heterocycloalkyl (e.g. 3 to 8 membered heterocycloalkyl, 4 to 8 membered heterocycloalkyl, or 5 to 6 membered heterocycloalkyl), $R^{14}$-substituted or unsubstituted aryl (e.g. $C_6$-$C_{10}$ aryl or $C_6$ aryl), or $R^{14}$-substituted or unsubstituted heteroaryl (e.g. 5 to 10 membered heteroaryl, 5 to 9 membered heteroaryl, or 5 to 6 membered heteroaryl). In embodiments, $R^{2b}$ is independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCF_3$, —$OCHF_2$, unsubstituted alkyl (e.g. $C_1$-$C_8$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

$R^{14}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCF_3$, —$OCHF_2$, $R^{15}$-substituted or unsubstituted alkyl (e.g. $C_1$-$C_8$ alkyl, $C_1$-$C_6$ alkyl, or $C_1$-$C_4$ alkyl), $R^{15}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{15}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{15}$-substituted or unsubstituted heterocycloalkyl (e.g. 3 to 8 membered heterocycloalkyl, 4 to 8 membered heterocycloalkyl, or 5 to 6 membered heterocycloalkyl), $R^{15}$-substituted or unsubstituted aryl (e.g. $C_6$-$C_{10}$ aryl or $C_6$ aryl), or $R^{15}$-substituted or unsubstituted heteroaryl (e.g. 5 to 10 membered heteroaryl, 5 to 9 membered heteroaryl, or 5 to 6 membered heteroaryl).

In embodiments, $R^9$, $R^{11}$, $R^{13}$, $R^{15}$ are independently oxo, halogen, —F, —Cl, —Br, —I, —$CF_3$, —$CCl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^3$ is monovalent polyethylene glycol (PEG). In embodiments, $R^3$ is monovalent $PEG_{400}$-SH. In embodiments, $R^3$ is monovalent $PEG_{1000}$-SH. In embodiments, $R^3$ is monovalent $PEG_{2000}$-SH. In embodiments, $R^3$ is monovalent $PEG_{5000}$-SH. It will be understood that the immediately preceding divalent PEG-SH groups may be bonded to a separate moiety through the terminal thiol group where the bond between sulfur and hydrogen is replaced with a bond between sulfur and another moiety. In embodiments, $R^3$ is monovalent TFP-$(PEG_{11})_3$. It will be understood that the immediately preceding monovalent TFP-PEG groups may be bonded to a separate moiety through the tetrafluorophenyl (TFP) ester group where the is between the tetrafluorophenyl ester and another moiety. In embodiments, $R^3$ is monovalent NHS-$(PEG_{24})_3$. It will be understood that the immediately preceding monovalent NSH-PEG groups may be bonded to a separate moiety through the N-hydroxysuccinimide group where the bond is between N-hydroxysuccinimide and another moiety. In embodiments, $R^3$ is a monovalent polyethylene glycol with an average molecular weight of about 400 g/mol, 484 g/mol, 1000 g/mol, 1450 g/mol, 1500 g/mol, 2000 g/mol, or 5000 g/mol. In embodiments, $R^3$ is a monovalent polyethylene glycol with an average molecular weight of about 400 g/mol. In embodiments, $R^3$ is a monovalent polyethylene glycol with an average molecular weight of about 484 g/mol. In embodiments, $R^3$ is a monovalent polyethylene glycol with an average molecular weight of about 484 g/mol per arm. In embodiments, $R^3$ is a monovalent polyethylene glycol with an average molecular weight of about 1000 g/mol. In embodiments, $R^3$ is a monovalent polyethylene glycol with an average molecular weight of about 1450 g/mol. In embodiments, $R^3$ is a monovalent polyethylene glycol with an average molecular weight of about 1500 g/mol. In embodiments, $R^3$ is a monovalent polyethylene glycol with an average molecular weight of about 2000 g/mol. In embodiments, $R^3$ is a monovalent polyethylene glycol with an average molecular weight of about 5000 g/mol.

In embodiments, —$X^2$— has the formula:

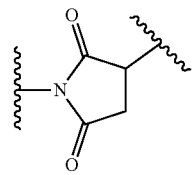

In embodiments, —$X^2$-$L^3$- has the formula:

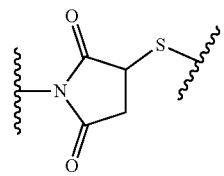

In embodiments, $X^3$ is —$NH_2$, —COOH, —N-hydroxysuccinimide, or maleimide. In embodiments, $X^3$ is

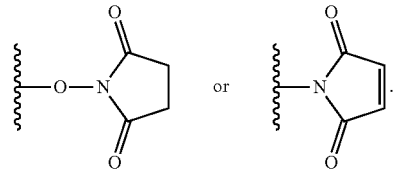 [SMILES: *ON1C(=O)CCC1=O ; *N1C(=O)C=CC1=O]

In embodiments, $X^3$ is -haloacetyl (eg., iodoacetyl, bromoacetyl, or chloroacetyl). In embodiments, $X^3$ is pyridyl. In embodiments, $X^3$ is maleimide. In embodiments, $X^3$ is —N-hydroxysuccinimide. In embodiments, $X^3$ is —COOH. In embodiments, $X^3$ is —$NH_2$.

In embodiments, z1 is independently 10. In embodiments, z1 is independently 9. In embodiments, z1 is independently 8. In embodiments, z1 is independently 7. In embodiments, z1 is independently 6. In embodiments, z1 is independently 5. In embodiments, z1 is independently 4. In embodiments, z1 is independently 3. In embodiments, z1 is independently 2. In embodiments, z1 is independently 1. In embodiments, z2 is independently 10. In embodiments, z2 is independently 9. In embodiments, z2 is independently 8. In embodiments, z2 is independently 7. In embodiments, z2 is independently 6. In embodiments, z2 is independently 5. In embodiments, z2 is independently 4. In embodiments, z2 is independently 3. In embodiments, z2 is independently 2. In embodiments, z2 is independently 1.

In embodiments, the platinum is in a (II) oxidation state. In embodiments, the platinum is in a (II) oxidation state when conjugated to the nanoparticle.

In embodiments, the nanoparticle-cell construct has the formula:

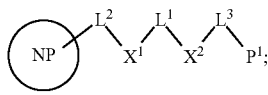

wherein NP is a nanoparticle and $P^1$ is a protein optionally attached to a cell (e.g., a stem cell). $L^2$, $X^1$, $L^1$, $X^2$, and $L^3$ are as described herein. In embodiments, the protein is attached to cell and is a cell surface protein.

In embodiments, the nanoparticle is a silica nanoparticle. The nanoparticle is typically composed of non-toxic material. The nanoparticle may be an inorganic nanoparticle. The inorganic nanoparticle may be a metal nanoparticle. The inorganic nanoparticle may be a metal oxide nanoparticle. The metal oxide nanoparticle may be titanium oxide or zirconium oxide. The nanoparticle may be titanium. The nanoparticle may be gold. The nanoparticle may be iron. The nanoparticle may be iron oxide.

In embodiments, the nanoparticle is a silica nanoparticle including a platinum anti-cancer agent, wherein the platinum anti-cancer agent is conjugated (e.g., covalently bound, bond between the Pt and an oxygen bound to Si) to the silica nanoparticle. In embodiments, the nanoparticle is a silica nanoparticle comprising cisplatin, wherein the cisplatin is conjugated directly to the silica nanoparticle (e.g., a Pt ligand of cisplatin has been replaced with a bond directly to an oxygen of silica). In embodiments, the cisplatin is encapsulated within the silica nanoparticle. In embodiments, the cisplatin is encapsulated within the silica nanoparticle and at the surface.

In embodiments, the protein is a cell surface protein. A cell surface protein refers to a protein at the surface of a protein. In embodiments, the cell surface protein is a transmembrane protein. In embodiments the protein is in contact with the extracellular matrix (e.g., extracellular matrix associated with a cancer cell or in contact with a cancer cell). In embodiments, the protein is in contact with a tumor. In embodiments, the tumor includes stromal cells, immune cells, proteins, and extracellular matrix generated by those cells. In embodiments, immune cells, stromal cells, proteins associate with the immune cells, proteins associated with the stromal cells, and the extracellular matrix generated from immune cells and stromal cells forms part of a tumor. In embodiments, the nanoparticle is incorporated within the cell. In embodiments, the nanoparticle is incorporated within the cell via the enhanced permeability and retention (EPR) effect.

In embodiments, the nanoparticle is further covalently attached to one or more nanoparticle substituents. In embodiments, the nanoparticle substituent includes a polymeric moiety. In embodiments, the polymeric moiety is a polyethylene glycol moiety. In embodiments, the nanoparticle substituents occupy about 5%, 10%, 15%, 20%, 25%, 40%, 50%, 60%, 75%, 80%, 90%, 95%, 99%, or about 100% of the nanoparticle surface.

In embodiments, the nanoparticle includes a plurality of nanoparticle substituents of the formula (i) and a plurality of nanoparticle substituents of the formula (ii), and not formula (iii). In embodiments, the nanoparticle includes a plurality of nanoparticle substituents of the formula (i) and a plurality of nanoparticle substituents of the formula (iii), and not formula (ii). In embodiments, the nanoparticle includes a plurality of nanoparticle substituents of the formula (ii) and a plurality of nanoparticle substituents of the formula (iii), and not formula (i). In embodiments, the nanoparticle includes a plurality of nanoparticle substituents of the formula (i), and not formula (ii) or formula (iii). In embodiments, the nanoparticle includes a plurality of nanoparticle substituents of the formula (ii), and not formula (i) or formula (iii). In embodiments, the nanoparticle includes a plurality of nanoparticle substituents of the formula (iii), and not formula (i) or formula (ii).

In embodiments, the nanoparticle includes a plurality of nanoparticle substituents of the formula (i) and a plurality of nanoparticle substituents of the formula (ii) in a ratio of about 50:50 to about 80:20. In embodiments, the ratio of a plurality of nanoparticle substituents of the formula (i) and a plurality of substituents of the formula (ii) is about 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, or 80:20.

In embodiments, the nanoparticle includes a plurality of nanoparticle substituents of the formula (i) and a plurality of nanoparticle substituents of the formula (iii) in a ratio of about 50:50 to about 80:20. In embodiments, the ratio of a plurality of nanoparticle substituents of the formula (i) and a plurality of substituents of the formula (iii) is about 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, or 80:20.

In embodiments, the nanoparticle includes a plurality of nanoparticle substituents of the formula (ii) and a plurality of nanoparticle substituents of the formula (iii) in a ratio of about 50:50 to about 80:20. In embodiments, the ratio of a plurality of nanoparticle substituents of the formula (ii) and a plurality of nanoparticle substituents of the formula (iii) is about 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, or 80:20.

In embodiments, the linker is formed by a conjugation or bioconjugation reaction combining a first reactant moiety covalently bonded to the polymeric linker and a second reactant moiety covalently bonded to a protein. In such embodiments, the compound formed by such conjugation or bioconjugation reaction (including compounds as described herein) to a cell may be referred to as a nanoparticle-cell construct.

III. PHARMACEUTICAL COMPOSITIONS

In another aspect, is provided a pharmaceutical composition including a pharmaceutically acceptable excipient and a nanoparticle, cell, or nanoparticle-cell construct, as described herein.

The compositions (e.g., nanoparticle, cell, or nanoparticle-cell construct) of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions (e.g., nanoparticle, cell, or nanoparticle-cell construct) of the present invention can also be administered by injection, that is, intravenously, intramuscularly, intracutaneously, subcutaneously, intraduodenally, or intraperitoneally. Also, the compositions (e.g., nanoparticle, cell, or nanoparticle-cell construct) described herein can be administered by inhalation, for example, intranasally. Additionally, the compositions (e.g., nanoparticle, cell, or nanoparticle-cell construct) of the present invention can be administered transdermally. It is also envisioned that multiple routes of administration (e.g., intramuscular, oral, transdermal) can be used to administer the compositions (e.g., nanoparticle, cell, or nanoparticle-cell construct) of the invention. Accordingly, the present invention also provides pharmaceutical compositions comprising a pharmaceutically acceptable excipient and one or more compositions (e.g., nanoparticle, cell, or nanoparticle-cell construct) of the invention.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of cancer symptoms. Determination of a therapeutically effective amount of a composition (e.g., nanoparticle, cell, or nanoparticle-cell construct) of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., cancer, ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer), kind of concurrent treatment, complications from the disease being treated or other health-related problems. Other therapeutic regimens or agents can be used in conjunction with the methods and compositions (e.g., nanoparticle, cell, or nanoparticle-cell construct) described herein. Adjustment and manipulation of established dosages (e.g., frequency and duration) are well within the ability of those skilled in the art.

The ratio between toxicity and therapeutic effect for a particular compositions (e.g., nanoparticle, cell, or nanoparticle-cell construct) is its therapeutic index and can be expressed as the ratio between $LD_{50}$ (the amount of compositions (e.g., nanoparticle, cell, or nanoparticle-cell construct) lethal in 50% of the population) and $ED_{50}$ (the amount of compositions (e.g., nanoparticle, cell, or nanoparticle-cell construct) effective in 50% of the population). Compositions (e.g., nanoparticle, cell, or nanoparticle-cell construct) that exhibit high therapeutic indices are preferred. Therapeutic index data obtained from cell culture assays and/or animal studies can be used in formulating a range of dosages for use in humans. The dosage of such compositions (e.g., nanoparticle, cell, or nanoparticle-cell construct) preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the composition (e.g., nanoparticle, cell, or nanoparticle-cell construct) is used.

The neutral forms of the compositions (e.g., nanoparticle, cell, or nanoparticle-cell construct) may be regenerated by contacting the salt with a base or acid and isolating the parent compound in the conventional manner. The parent form of the composition (e.g., nanoparticle, cell, or nanoparticle-cell construct) differs from the various salt forms in certain physical properties, such as solubility in polar solvents, but otherwise the salts are equivalent to the parent form of the composition (e.g., nanoparticle, cell, or nanoparticle-cell construct) for the purposes of the present invention.

Certain compositions described herein of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly include a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compositions (e.g., nanoparticle, cell, or nanoparticle-cell construct) described herein can be used in combination with one another, with other active agents known to be useful in treating cancer (e.g. ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer), or with adjunctive agents that may not be effective alone, but may contribute to the efficacy of the active agent.

In embodiments, the nanoparticles, cells, or nanoparticle-cell constructs described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), other platinum-based compounds (e.g. cisplatin, oxaloplatin, carboplatin, a second platinum-based compound described herein), and the like.

The nanoparticles, cells, or nanoparticle-cell constructs or drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

In a further embodiment, the nanoparticles, cells, or nanoparticle-cell constructs or drugs described herein can be co-administered with conventional radiotherapeutic agents including, but not limited to, radionuclides such as $^{47}Sc$, $^{64}Cu$, $^{67}Cu$, $^{89}Sr$, $^{86}Y$, $^{87}Y$, $^{90}Y$, $^{105}Rh$, $^{111}Ag$, $^{111}In$, $^{117m}Sn$, $^{149}Pm$, $^{153}Sm$, $^{166}Ho$, $^{177}Lu$, $^{186}Re$, $^{188}Re$, $^{211}At$, and $^{212}Bi$, optionally conjugated to antibodies directed against tumor antigens.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged nanoparticles, cells, or nanoparticle-cell constructs or drug suspended in diluents, e.g., water, saline, or PEG 400; (b) capsules, sachets, or tablets, each containing a predetermined amount of a nanoparticles, cells, or nanoparticle-cell constructs or drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a nanoparticles, cells, or nanoparticle-cell constructs or drug in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The nanoparticles, cells, or nanoparticle-cell constructs or drug (e.g., anti-cancer agent) of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged nanoparticles, cells, or nanoparticle-cell constructs or drug with a suppository base. Suitable suppository bases include natural or synthetic triglycerides or paraffin hydrocarbons. In addition, it is also possible to use gelatin rectal capsules which contain a combination of the nanoparticles, cells, or nanoparticle-cell constructs or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compositions (e.g., nanoparticle, cell, or nanoparticle-cell construct) can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., nanoparticles, cells, or nanoparticle-cell constructs or drug. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

IV. METHODS OF USE

In an aspect is provided a method of treating cancer in a patient in need of such treatment, the method including administering to a subject in need thereof a therapeutically effective amount of the nanoparticle, the cell, or the nanoparticle-cell construct, as described herein. In embodiments, the method is administering to a subject in need thereof a therapeutically effective amount of the nanoparticle as described herein. In embodiments, the method is administering to a subject in need thereof a therapeutically effective amount of the cell as described herein. In embodiments, the method is administering to a subject in need thereof a therapeutically effective amount of the nanoparticle-cell construct as described herein.

In embodiments, the cancer is ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer. In embodiments, the cancer is ovarian cancer, bladder cancer, head and neck cancer, prostate cancer, brain cancer, breast cancer, lung cancer, cervical cancer, liver cancer, bone cancer, or spinal cancer. In embodiments, the cancer is ovarian cancer.

In embodiments, the nanoparticle, cell, or nanoparticle-cell construct is administered via intraperitoneal injection, intratumoral injection, intraurethral injection, or intramuscular injection. In embodiments, the nanoparticle, cell, or nanoparticle-cell construct is administered via intraperitoneal injection. In embodiments, the nanoparticle, cell, or nanoparticle-cell construct is administered via intraurethral injection. In embodiments, the nanoparticle, cell, or nanoparticle-cell construct is administered via intramuscular injection. In embodiments, the nanoparticle, cell, or nanoparticle-cell construct is administered via intratumoral injection.

V. EMBODIMENTS

Embodiment P1

A silica nanoparticle comprising an unmodified platinum anti-cancer agent.

Embodiment P2

The silica nanoparticle of embodiment P1, wherein the unmodified platinum anti-cancer agent is conjugated directly to the silica nanoparticle.

Embodiment P3

The silica nanoparticle of embodiments P1 or P2, wherein the unmodified platinum anti-cancer agent is cisplatin, carboplatin, oxaliplatin, nedaplatin, lobaplatin, or heptaplatin.

Embodiment P4

The silica nanoparticle of one of embodiments P1 to P3, wherein the silica:platinum mass ratio is about 10:1 to 40:1.

Embodiment P5

The silica nanoparticle of one of embodiments P1 to P4, wherein the average longest dimension of the silica nanoparticle is from about 10 nm to about 600 nm.

Embodiment P6

The silica nanoparticle of any one of embodiments P1 to P4, wherein the average longest dimension of the silica nanoparticle is from about 100 nm to about 400 nm.

Embodiment P7

The silica nanoparticle of any one of embodiments P1 to P4, wherein the average longest dimension of the silica nanoparticle is from about 170 nm to about 270 nm.

Embodiment P8

The silica nanoparticle of any one of embodiments P1 to P7, wherein the silica nanoparticle further comprises a detectable agent.

Embodiment P9

The silica nanoparticle of embodiment P8, wherein the detectable agent is a radioisotope, fluorophore, electron-dense reagent, enzyme, biotin, paramagnetic agent, or magnetic agent.

Embodiment P10

A cell comprising the nanoparticle of one of embodiments P1 to P9.

Embodiment P11

The cell of embodiment P10, wherein the cell is a neural stem cell.

Embodiment P12

A pharmaceutical composition comprising a pharmaceutically acceptable excipient and the silica nanoparticle of any one of embodiments P1 to P9 or the cell of one of embodiments P10 or P11.

Embodiment P13

A nanoparticle-cell construct comprising a nanoparticle covalently attached to a protein through a covalent linker, said covalent linker having the formula:

$$-L^2-X^1-L^1-X^2-L^3-;\quad\quad\quad\text{(Ia) or}$$

$$-L^2-X^2-L^3-;\quad\quad\quad\text{(Ib)}$$

wherein
X¹ and X² are independently a bioconjugate linker or a bond, wherein at least one of X¹ or X² is a bioconjugate linker;
L¹ is independently a polymeric linker;
L² is independently a bond, —NR$^{1a}$—, —O—, —S—, —C(O)—, —C(O)O—, —S(O)—, —S(O)$_2$—, —NR$^{1a}$C(O)—, —C(O)NR$^{1b}$—, —C(O)(CH$_2$)$_{z1}$—, —NR$^{1a}$C(O)O—, —NR$^{1a}$C(O)NR$^{1b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
L³ is independently a bond, —NR$^{2a}$—, —O—, —S—, —C(O)—, —C(O)O—, —S(O)—, —S(O)$_2$—, —NR$^{2a}$C(O)—, —C(O)NR$^{2b}$—, —C(O)(CH$_2$)$_{z2}$—, —NR$^{2a}$C(O)O—, —NR$^{2a}$C(O)NR$^{2b}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
R$^{1a}$, R$^{2a}$, R$^{1b}$, and R$^{2b}$ are independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
the symbols z1 and z2 are independently an integer from 1 to 10.

Embodiment P14

The nanoparticle-cell construct of embodiment P13, wherein the nanoparticle is a silica nanoparticle.

Embodiment P15

The nanoparticle-cell construct of embodiments P13 or P14, wherein the nanoparticle comprises a platinum anti-cancer agent.

Embodiment P16

The nanoparticle-cell construct of any of embodiments P13 to P15, wherein the nanoparticle comprises a platinum anti-cancer agent conjugated directly to the nanoparticle.

Embodiment P17

The nanoparticle-cell construct of any one of embodiments P13 to P16, wherein the nanoparticle comprises cisplatin.

Embodiment P18

The nanoparticle-cell construct of any one of embodiments P13 to P17, wherein the protein is a cell surface protein.

Embodiment P19

The nanoparticle-cell construct of any one of embodiments P13 to P18, wherein the protein comprises a sulfur-containing amino acid.

Embodiment P20

The nanoparticle-cell construct of any one of embodiments P13 to P19, wherein X² has the formula:

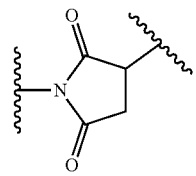

Embodiment P21

The nanoparticle-cell construct of any one of embodiments P13 to P19, wherein X²-L³- has the formula:

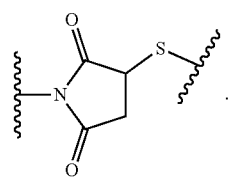 [SMILES: *SC1CC(=O)N(*)C1=O]

Embodiment P22

The nanoparticle-cell construct of any one of embodiments P13 to P21, wherein L¹ is a branched polymeric linker.

Embodiment P23

The nanoparticle-cell construct of any one of embodiments P13 to P22, wherein L¹ is polyethylene glycol with an average molecular weight of 400, 484, 1000, 1450, 1500, 2000, or 5000.

Embodiment P24

The nanoparticle-cell construct of any one of embodiments P13 to P22, wherein L¹ is polyethylene glycol with an average molecular weight of 2000.

Embodiment P25

The nanoparticle-cell construct of any one of embodiments P13 to P23, wherein said nanoparticle is further covalently attached to one or more nanoparticle substituents.

Embodiment P26

The nanoparticle-cell construct of embodiment P25, wherein said nanoparticle substituent is:

-L²-X¹—R³;  (i)

-L²-X¹-L¹-X³;  (ii) or

-L²-X³;  (iii)

wherein

R³ is a polymeric moiety;

X³ is a bioconjugate reactive group.

Embodiment P27

The nanoparticle-cell construct of embodiment P26, wherein R³ is a polyethylene glycol moiety.

Embodiment P28

The nanoparticle-cell construct of embodiments P26 or P27, wherein the bioconjugate reactive group is —NH₂, —COOH, —N-hydroxysuccinimide, or -maleimide.

Embodiment P29

The nanoparticle-cell construct of any one of embodiments P26 to P28 comprising a plurality of nanoparticle substituents of the formula (i) and a plurality of nanoparticle substituents of the formula (ii) in a ratio of about 50:50 to about 80:20.

Embodiment P30

The nanoparticle-cell construct of any one of embodiments P26 to P28 comprising a plurality of nanoparticle substituents of the formula (ii) and a plurality of nanoparticle substituents of the formula (iii) in a ratio of about 50:50 to about 80:20.

Embodiment P31

The nanoparticle-cell construct of any one of embodiments P26 to P28 comprising a plurality of nanoparticle substituents of the formula (i) and a plurality of nanoparticle substituents of the formula (iii) in a ratio of about 50:50 to about 80:20.

Embodiment P32

The nanoparticle-cell construct of any one of embodiments P13 to P31, wherein each L¹ is independently a linear or branched polymeric linker.

Embodiment P33

A pharmaceutical composition comprising a pharmaceutically acceptable excipient and a construct of any one of embodiments P13 to P32.

Embodiment P34

A method of treating cancer in a subject in need of such treatment, said method comprising administering to the subject a therapeutically effective amount of the nanoparticle, or pharmaceutical composition thereof, of any one of embodiments P1 to P9, the cell, or pharmaceutical composition thereof of embodiments P10 or P11, or the nanoparticle-cell construct of any one of embodiments P13 to P32, or a pharmaceutical composition thereof of embodiment 33.

Embodiment P35

The method of embodiment P34, wherein the cancer is ovarian cancer, bladder cancer, head and neck cancer, brain cancer, breast cancer, lung cancer, cervical cancer, bone cancer, spinal cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer.

Embodiment P36

The method of embodiment P34 or P35, wherein the cancer is ovarian cancer, bladder cancer, head and neck cancer, prostate cancer, brain cancer, breast cancer, lung cancer, cervical cancer, liver cancer, bone cancer, or spinal cancer.

Embodiment P37

The method of any one of embodiments P34 to P36, wherein the nanoparticle, cell, or nanoparticle-cell construct is administered via intraperitoneal injection, intratumoral injection, intraurethral injection, or intramuscular injection.

VI. ADDITIONAL EMBODIMENTS

Embodiment 1

A silica nanoparticle comprising a platinum anti-cancer agent, wherein the platinum anti-cancer agent is conjugated to silica directly, though an oxygen linker, or through a nitrogen linker.

Embodiment 2

The silica nanoparticle of embodiment 1, wherein the platinum anti-cancer agent is conjugated to silica though an oxygen linker.

Embodiment 3

The silica nanoparticle of embodiments 1 or 2, wherein the platinum anti-cancer agent is cisplatin, carboplatin, oxaliplatin, nedaplatin, lobaplatin, or heptaplatin.

Embodiment 4

The silica nanoparticle of embodiments 1 or 2, wherein the platinum anti-cancer agent is a platinum salt.

Embodiment 5

The silica nanoparticle of one of embodiments 1 to 4, wherein the silica:platinum mass ratio is about 10:1 to 40:1.

Embodiment 6

The silica nanoparticle of one of embodiments 1 to 5, wherein the average longest dimension of the silica nanoparticle is from about 10 nm to about 1000 nm.

Embodiment 7

The silica nanoparticle of one of embodiments 1 to 5, wherein the average longest dimension of the silica nanoparticle is from about 10 nm to about 600 nm.

Embodiment 8

The silica nanoparticle of one of embodiments 1 to 5, wherein the average longest dimension of the silica nanoparticle is from about 100 nm to about 400 nm.

Embodiment 9

The silica nanoparticle of one of embodiments 1 to 5, wherein the average longest dimension of the silica nanoparticle is from about 170 nm to about 270 nm.

Embodiment 10

The silica nanoparticle of any one of embodiments 1 to 9, wherein the silica nanoparticle further comprises a detectable agent.

Embodiment 11

The silica nanoparticle of embodiment 10, wherein the detectable agent is a radioisotope, fluorophore, electron-dense reagent, enzyme, biotin, paramagnetic agent, or magnetic agent.

Embodiment 12

The silica nanoparticle of embodiment 10, wherein the detectable agent is a fluorophore.

Embodiment 13

A cell comprising the silica nanoparticle of one of embodiments 1 to 12.

Embodiment 14

The cell of embodiment 13, wherein the cell is a neural stem cell.

Embodiment 15

A pharmaceutical composition comprising a pharmaceutically acceptable excipient and the silica nanoparticle of any one of embodiments 1 to 12 or the cell of one of embodiments 13 or 14.

Embodiment 16

A nanoparticle-cell construct comprising an inorganic nanoparticle covalently attached to a protein through a covalent linker, said covalent linker having the formula:

$$-L^2-X^1-L^1-X^2-L^3-;  \quad (Ia)$$

or $$-L^2-X^2-L^3-;  \quad (Ib)$$

wherein $X^1$ and $X^2$ are independently a bioconjugate linker or a bond, wherein at least one of $X^1$ or $X^2$ is a bioconjugate linker;

$L^1$ is independently a polymeric linker;

$L^2$ is independently a bond, $-NR^{1a}$, $-O-$, $-S-$, $-C(O)-$, $-C(O)O-$, $-S(O)-$, $-S(O)_2-$, $-NR^{1a}C(O)-$, $-C(O)NR^{1b}-$, $-C(O)(CH_2)_{z1}-$, $-NR^{1a}C(O)O-$, $-NR^{1a}C(O)NR^{1b}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is independently a bond, $-NR^{2a}-$, $-O-$, $-S-$, $-C(O)-$, $-C(O)O-$, $-S(O)-$, $-S(O)_2-$, $-NR^{2a}C(O)-$, $-C(O)NR^{2b}-$, $-C(O)(CH_2)_{z2}-$, $-NR^{2a}C(O)O-$, $-NR^{2a}C(O)NR^{2b}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{1a}$, $R^{2a}$, $R^{1b}$, and $R^{2b}$ are independently hydrogen, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and the symbols z1 and z2 are independently an integer from 1 to 10.

Embodiment 17

The nanoparticle-cell construct of embodiment 16, wherein the inorganic nanoparticle is a silica nanoparticle.

Embodiment 18

The nanoparticle-cell construct of embodiments 16 or 17, wherein the inorganic nanoparticle comprises a platinum anti-cancer agent.

Embodiment 19

The nanoparticle-cell construct of embodiment 18, wherein the inorganic nanoparticle comprises a platinum anti-cancer agent, which is conjugated to silica through an oxygen linker.

Embodiment 20

The nanoparticle-cell construct of any one of embodiments 18 to 19, wherein the nanoparticle comprises cisplatin.

Embodiment 21

The nanoparticle-cell construct of any one of embodiments 16 to 20, wherein the protein is a cell surface protein.

Embodiment 22

The nanoparticle-cell construct of any one of embodiments 16 to 20, wherein the protein comprises a sulfur-containing amino acid.

Embodiment 23

The nanoparticle-cell construct of any one of embodiments 16 to 22, wherein $X^2$ has the formula:

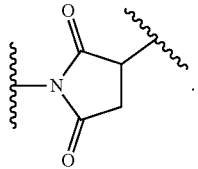 [SMILES: *C1CC(=O)N(*)C1=O]

Embodiment 24

The nanoparticle-cell construct of any one of embodiments 16 to 22, wherein $X^2$-$L^3$- has the formula:

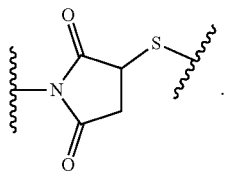 [SMILES: *SC1CC(=O)N(*)C1=O]

Embodiment 25

The nanoparticle-cell construct of any one of embodiments 16 to 24, wherein $L^1$ is a branched polymeric linker.

Embodiment 26

The nanoparticle-cell construct of any one of embodiments 16 to 25, wherein $L^1$ is polyethylene glycol with an average molecular weight of 400 g/mol, 484 g/mol, 1000 g/mol, 1450 g/mol, 1500 g/mol, 2000 g/mol, or 5000 g/mol.

Embodiment 27

The nanoparticle-cell construct of any one of embodiments 16 to 25, wherein $L^1$ is polyethylene glycol with an average molecular weight of 2000 g/mol.

Embodiment 28

The nanoparticle-cell construct of any one of embodiments 16 to 27, wherein said nanoparticle is further covalently attached to one or more nanoparticle substituents.

Embodiment 29

The nanoparticle-cell construct of embodiment 28, wherein said nanoparticle substituent is:

-$L^2$-$X^1$—$R^3$;  (i)

-$L^2$-$X^1$-$L^1$-$X^3$;  (ii) or

-$L^2$-$X^3$;  (iii)

wherein
$R^3$ is a polymeric moiety; and
$X^3$ is a bioconjugate reactive group.

Embodiment 30

The nanoparticle-cell construct of embodiment 29, wherein $R^3$ is a polyethylene glycol moiety.

Embodiment 31

The nanoparticle-cell construct of embodiments 29 or 30, wherein the bioconjugate reactive group is —$NH_2$, —COOH,

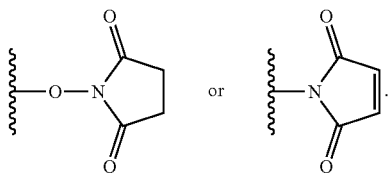 [SMILES: *ON1C(=O)CCC1=O ; *N1C(=O)C=CC1=O]

Embodiment 32

The nanoparticle-cell construct of any one of embodiments 29 to 31 comprising a plurality of nanoparticle substituents of the formula (i) and a plurality of nanoparticle substituents of the formula (ii) in a ratio of from about 50:50 to about 80:20.

Embodiment 33

The nanoparticle-cell construct of any one of embodiments 29 to 31 comprising a plurality of nanoparticle substituents of the formula (ii) and a plurality of nanoparticle substituents of the formula (iii) in a ratio of from about 50:50 to about 80:20.

Embodiment 34

The nanoparticle-cell construct of any one of embodiments 29 to 31 comprising a plurality of nanoparticle substituents of the formula (i) and a plurality of nanoparticle substituents of the formula (iii) in a ratio of from about 50:50 to about 80:20.

Embodiment 35

The nanoparticle-cell construct of any one of embodiments 16 to 32, wherein each $L^1$ is independently a linear or branched polymeric linker.

Embodiment 36

A pharmaceutical composition comprising a pharmaceutically acceptable excipient and a nanoparticle-cell construct of any one of embodiments 16 to 35.

Embodiment 37

A method of treating cancer in a subject in need of such treatment, said method comprising administering to the subject a therapeutically effective amount of the nanoparticle of one of embodiments 1 to 12, the cell of one of embodiments 13 to 14, the pharmaceutical composition of embodiment 15 or 36, or the nanoparticle-cell construct of one of embodiments 16 to 35.

Embodiment 38

The method of embodiment 37, wherein the cancer is ovarian cancer, bladder cancer, head and neck cancer, brain cancer, breast cancer, lung cancer, cervical cancer, bone cancer, spinal cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer.

Embodiment 39

The method of embodiment 37 or 38, wherein the cancer is ovarian cancer, bladder cancer, head and neck cancer, prostate cancer, brain cancer, breast cancer, lung cancer, cervical cancer, liver cancer, bone cancer, or spinal cancer.

Embodiment 40

The method of any one of embodiments 37 to 39, wherein the nanoparticle, cell, or nanoparticle-cell construct is administered via intraperitoneal injection, intratumoral injection, intraurethral injection, or intramuscular injection.

Embodiment 41

The method of any one of embodiments 37 to 39, wherein the nanoparticle, cell, or nanoparticle-cell construct is administered via intraperitoneal injection.

EXAMPLES

Applicants have optimized the preparation to encapsulate an unmodified cisplatin precursor by silica nanoparticles (NPs) via a one-pot reaction, and these cisplatin-NPs demonstrated delayed drug release over 3 days via in vitro efficacy MTT assay. We then labeled NSCs with cisplatin-NPs and injected these NSC-NP constructs in mice bearing ovarian cancer tumors. We then quantified the amount of Pt accumulation at tumors and in organs by ICP-MS. Our data demonstrated that NSC-NP constructs have superior accumulation and retention of Pt in tumors than both free cisplatin and free cisplatin-NPs. Current work focuses on the long term survival of ovarian cancer-bearing mice treated with NSC-NP constructs.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

A. Synthesis Conditions

In a standard reaction, 12 mg cisplatin powder and 40 mL tetraethyl orthosilicate (TEOS) were added to a microemulsion system that contains a mixture of 7.7 mL cyclohexane, 2 mL Triton X-100, 1.6 mL hexanol, and 0.34 mL MilliQ water. This mixture was stirred at 400 rpm for 5 h, at room temperature, followed by the addition of 100 μL aqueous ammonia. This reaction mixture was stirred at 400 rpm for 16 h, at room temperature. The following day, the mixture was transferred to a 50 mL tube and EtOH was used to quench the NPs out of solution. SiNP-Cis was collected by centrifugation (3220 g, 10 min). The supernatant was discarded, the NP pellet was redispersed in 2 mL EtOH and transferred to a 2 mL eppendorf. SiNP-Cis was washed via repeated centrifugation by 2 more times with EtOH and 3 more times with MilliQ water (21,000 g, 1.5 min). The NP solution was sonicated in between washes to assist their redispersion back into solution. After the final wash, SiNP-Cis was dispersed in 0.5 mL MilliQ water and stored at 4° C.

For non-cisplatin containing nanoparticles. In a standard reaction, 40 mL tetraethyl orthosilicate (TEOS) were added to a microemulsion system that contains a mixture of 7.7 mL cyclohexane, 2 mL Triton X-100, 1.6 mL hexanol, and 0.34 mL MilliQ water. This mixture was stirred at 400 rpm for 5 h, at room temperature, followed by the addition of 100 μL aqueous ammonia. This reaction mixture was stirred at 400 rpm for 16 h, at room temperature. To prepare the fluorophore for silica nanoparticle incorporation, 35 μmol of amine-reactive fluorophore (NHS- or TFP-activated dyes) and 35 μmol of (3-Aminopropyl)triethoxysilane was added to 100 μL of absolute EtOH and shaken overnight at room temperature. The following day, the mixture containing APS-fluorophore adduct and 20 μL of aqueous ammonia was added to the silica microemulsion system and it was stirred for another 16 hr at room temperature. Upon reaction completion, the mixture was transferred to a 50 mL tube and EtOH was used to quench the NPs out of solution. Fluorescently-labeled SiNPs were collected by centrifugation (3220 g, 10 min). The supernatant was discarded, the NP pellet was redispersed in 2 mL EtOH and transferred to a 2 mL eppendorf SiNPs were washed via repeated centrifugation by 2 more times with EtOH and 3 more times with MilliQ water (21,000 g, 1.5 min). The NP solution was sonicated in between washes to assist their redispersion back into solution. After the final wash, SiNPs were dispersed in MilliQ water and stored at 4° C.

Functionalizing the terminal —OH with —NH$_2$. A 25 mL round bottom flask with a magnetic stirring bar was flushed with nitrogen for 10 minutes. A dispersion of red silica nanoparticles (500 nm, $3.8 \times 10^{11}$ NPs) in 4 mL ethanol was added to the flask under nitrogen followed by the addition of 0.67 mL of aqueous ammonia. The final NP concentration was 10 g/L in the solution mixture with a final ammonia concentration of 4 vol. %. (3-Aminopropyl)triethoxysilane (APTES, 1 uL) in 0.33 mL of EtOH was then added to the reaction mixture and it was stirred at room temperature overnight. The following day, the reaction was refluxed at 85° C. while stirring for 2 h. The resulting NPs in the dispersion were collected and washed by repeated centrifugation at 21,000 g, 1 min (3 washes in EtOH, followed by 3 washes in MilliQ water). The amount of APTES was calculated under the assumption that each APTES molecule takes up 0.6 nm$^2$ on the NP surface. To ensure the complete conversion of the hydroxyl groups to amine groups on the NP surface, a 7-fold excess of APTES was used in the reaction. SiNP—NH$_2$ was redispersed in MilliQ water and stored at 4° C.; see FIG. 1.

Functionalizing terminal —NH$_2$ with maleimide. A water dispersion of SiNP—NH$_2$ containing $1.9 \times 10^{11}$ NPs was exchanged to PBS solution by 3 repeated centrifugation cycles at 21,000 g, 1 min in PBS. A 25-fold molar excess of sulfo-SMCC solution in PBS was added to the SiNP—NH$_2$ and the mixture was shaken at 37° C. for 1 hr. To remove the salts and excess sulfo-SMCC, SiNPs were pelleted and washed 3 times with MilliQ water by centrifugation (21,000 g, 1 min). The resulting SiNP-Mal particles were redispersed in MilliQ water and stored at 4° C.; see FIG. 1.

Figure 2:
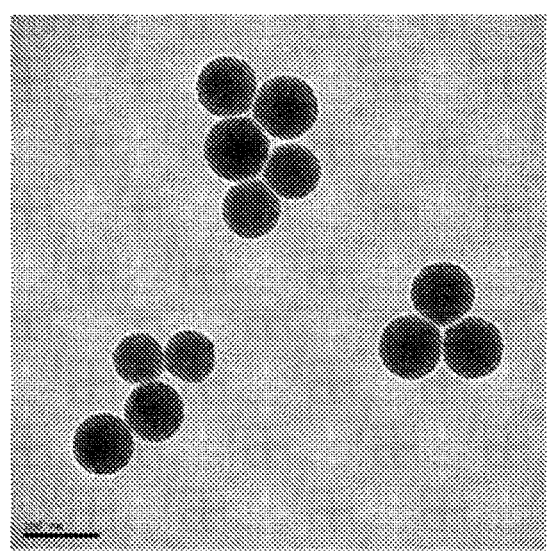
FIG. 2. A TEM image of carboplatin loaded nanoparticles. The synthesis of SiNP-Carbo was identical to standard synthetic preparation of SiNP-Cis. Instead of 12 mg cisplatin, 12 mg of carboplatin was added to the reaction mixture. Comparing to SiNP-Cis particles, SiNP-Carbo also maintained their morphology. They appear to be roughly the same size and shape to SiNP-Cis.
Figure 3:
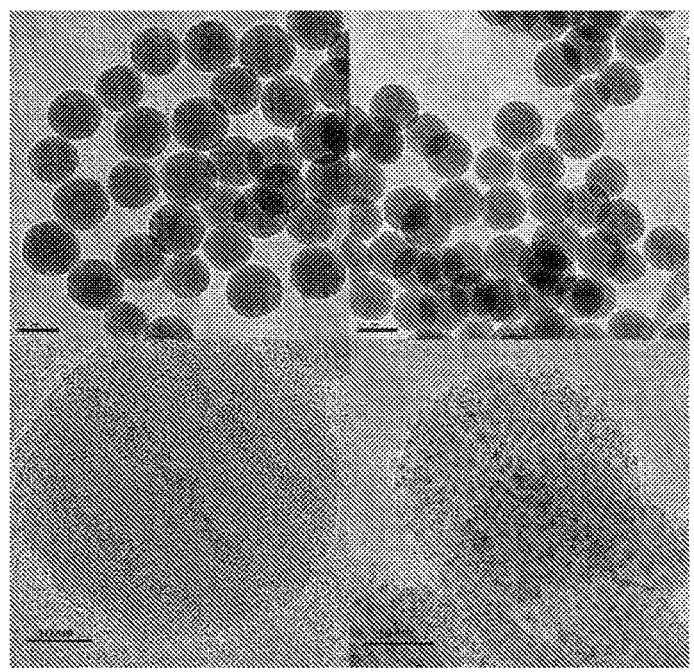
FIG. 3. High resolution TEM image of empty and cisplatin loaded nanoparticles. Dark spots indicating Pt are only visible in the loaded particles.
Figure 4:
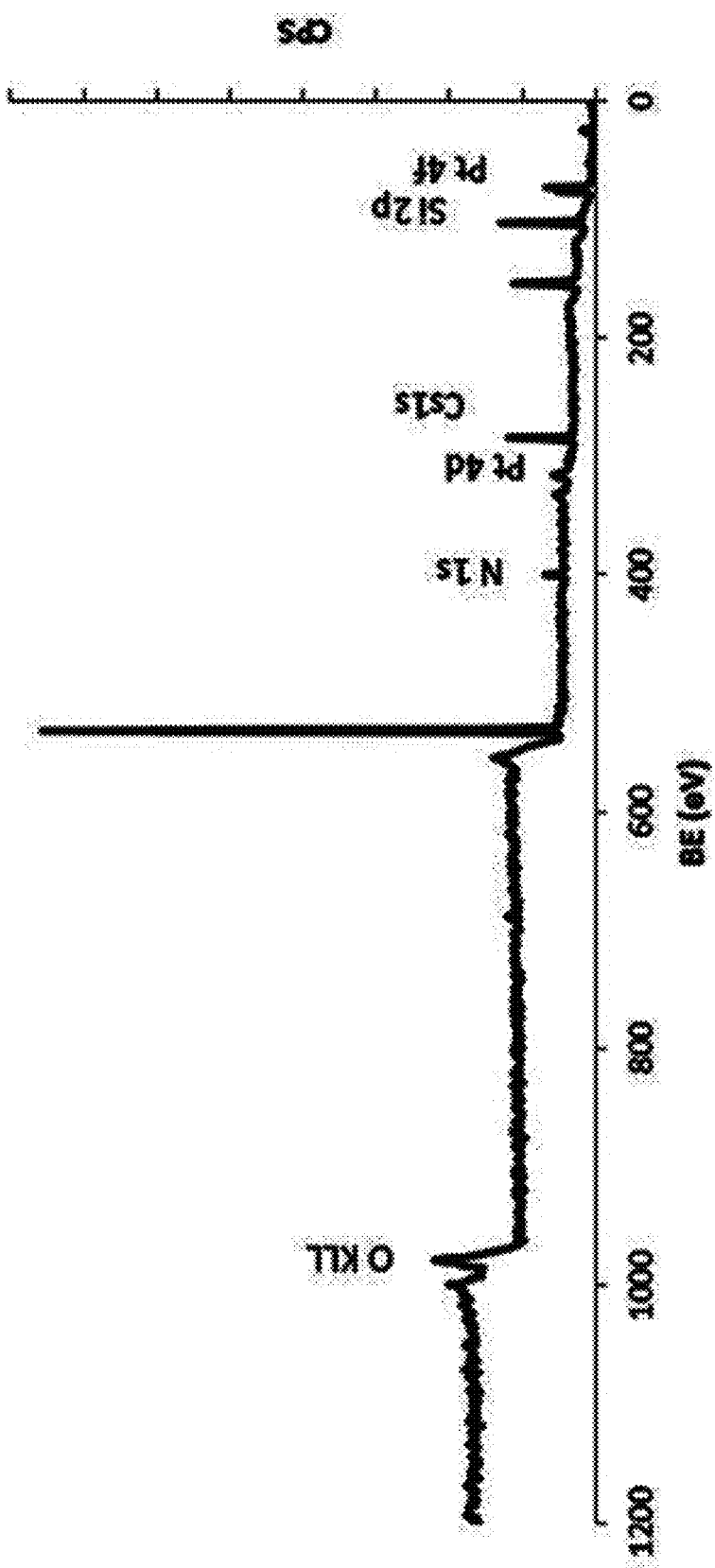
FIG. 4. XPS analysis of cisplatin loaded nanoparticles.
Figure 5:
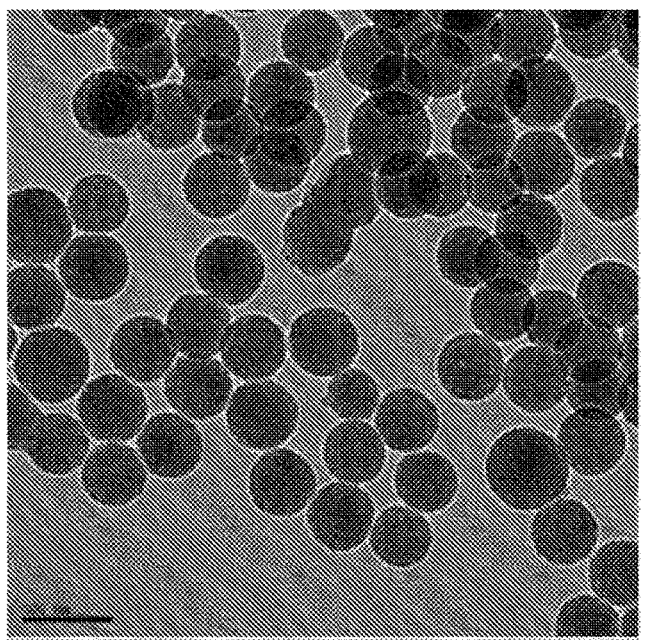
FIG. 5. The effects of surface modification. PEGylated SiNP-Cis retained their morphology as they had very similar shape and size to SiNP-Cis. The amount of Pt in SiNP-Cis-PEG was measured by ICP-MS, noted to be about 0.1 µg/µL Pt.
Figure 6A:
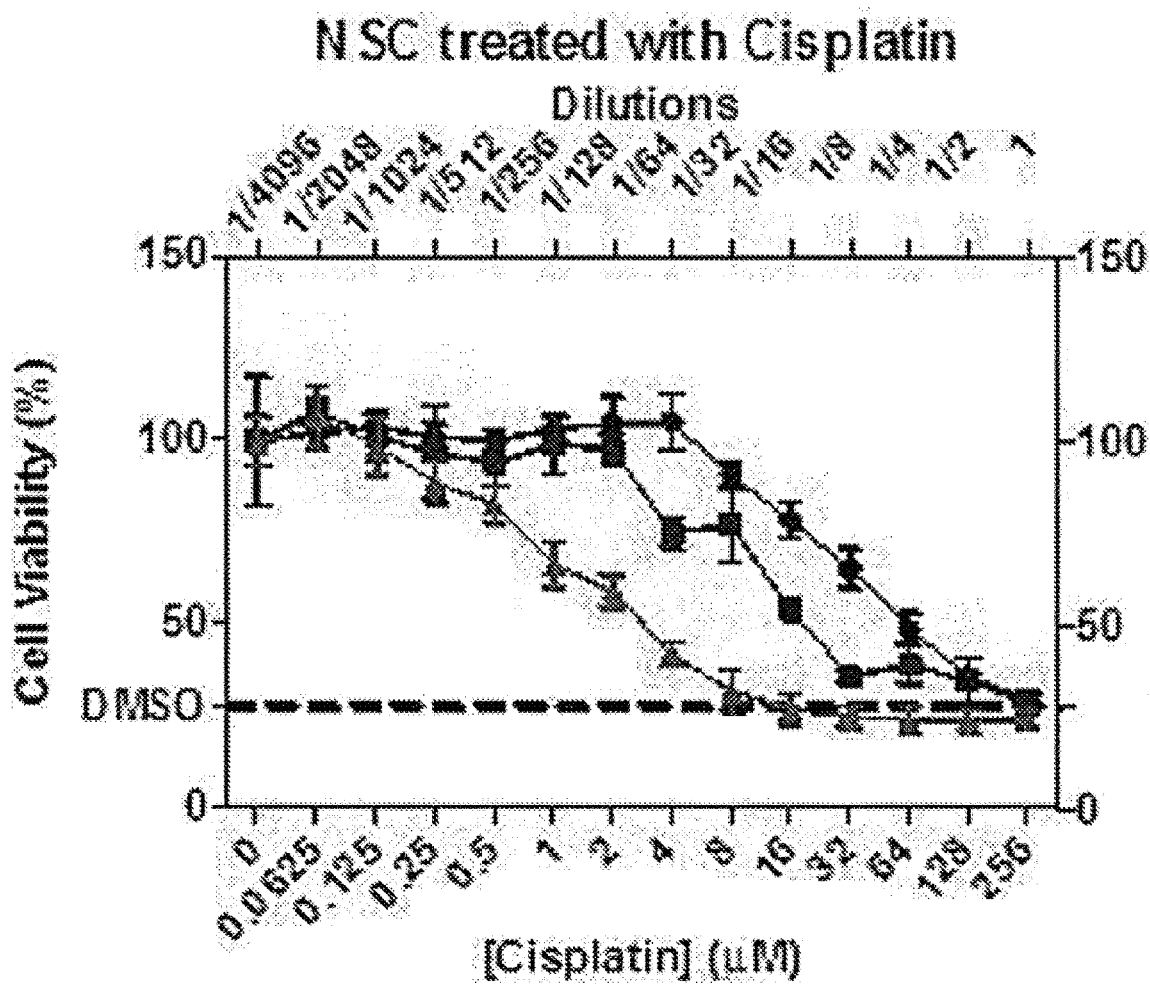
FIGS. 6A-6C. The results of the delayed release for SiNP-Cis synthesized using 200 µL TEOS and 500 µL NH$_4$OH. In vitro study suggested that SiNP-Cis was able to delay the effect of cisplatin on NSCs by roughly 2 d. This may be enough time for NSCs loaded with SiNP-Cis to migrate to tumors.
Figure 6B:
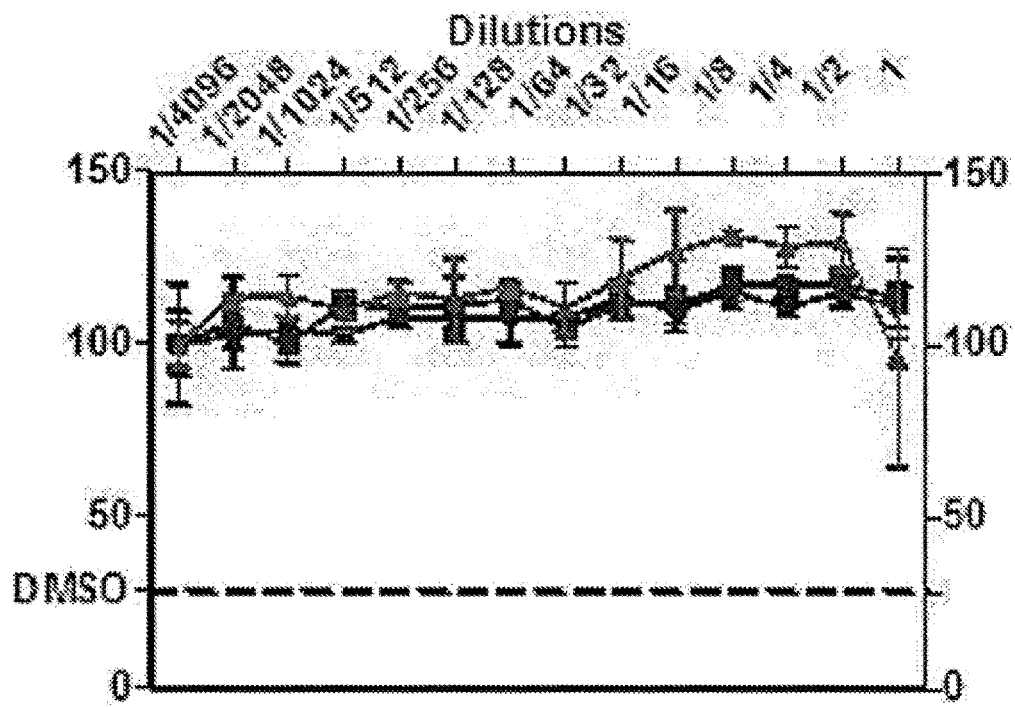
Figure 6C:
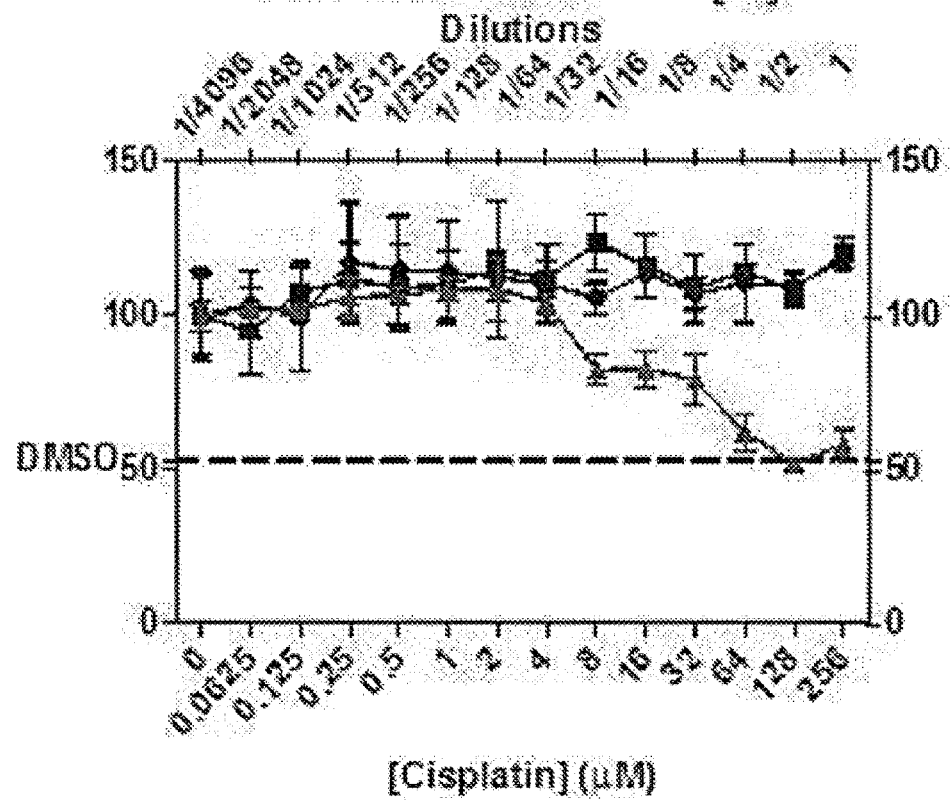
Figure 7A:
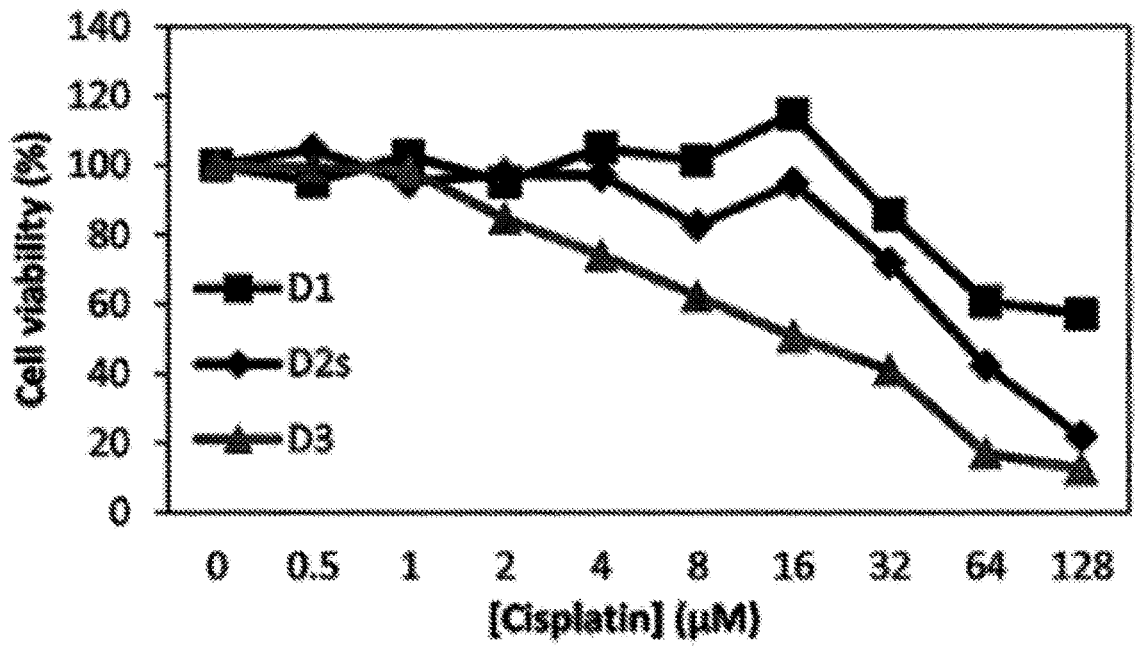
FIGS. 7A-7D. The effect of treatment of NSCs (FIGS. 7A-7B) and OVCAR8 (FIGS. 7C-7D) cells with SiNP-Cis made using two different synthesis protocols, 200 µL TEOS and 500 µL NH$_4$OH (FIG. 7B and FIG. 7D) vs 1000 µL TEOS and 300 µL NH$_4$OH (FIG. 7A and FIG. 7C).
Figure 7B:
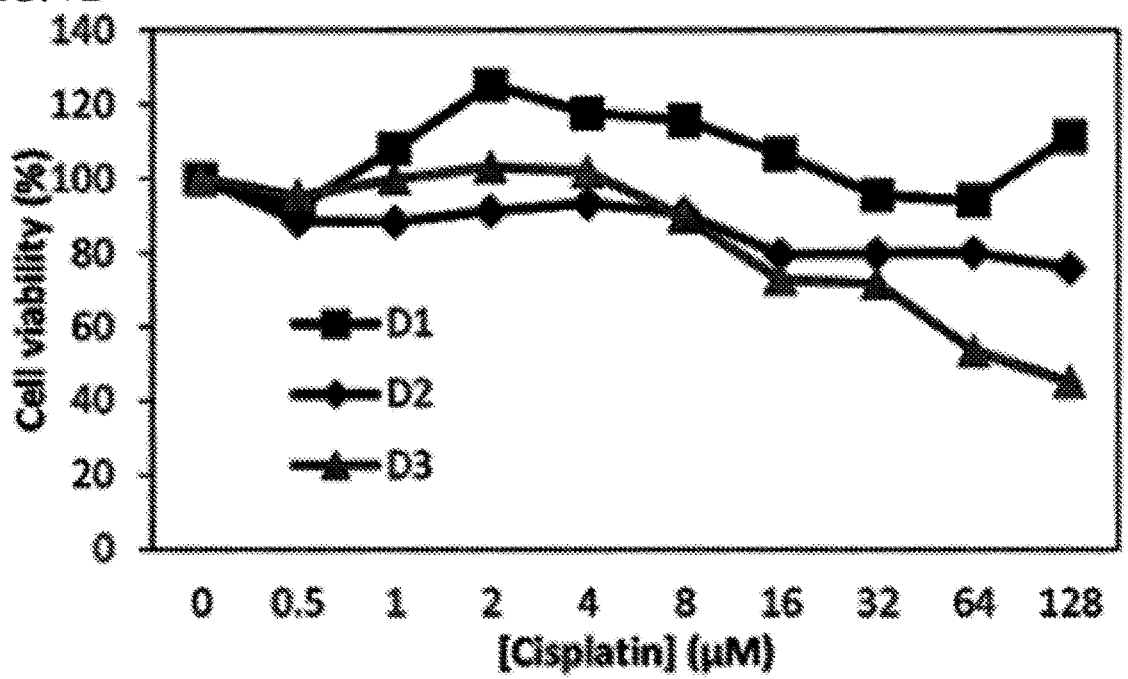
Figure 7C:
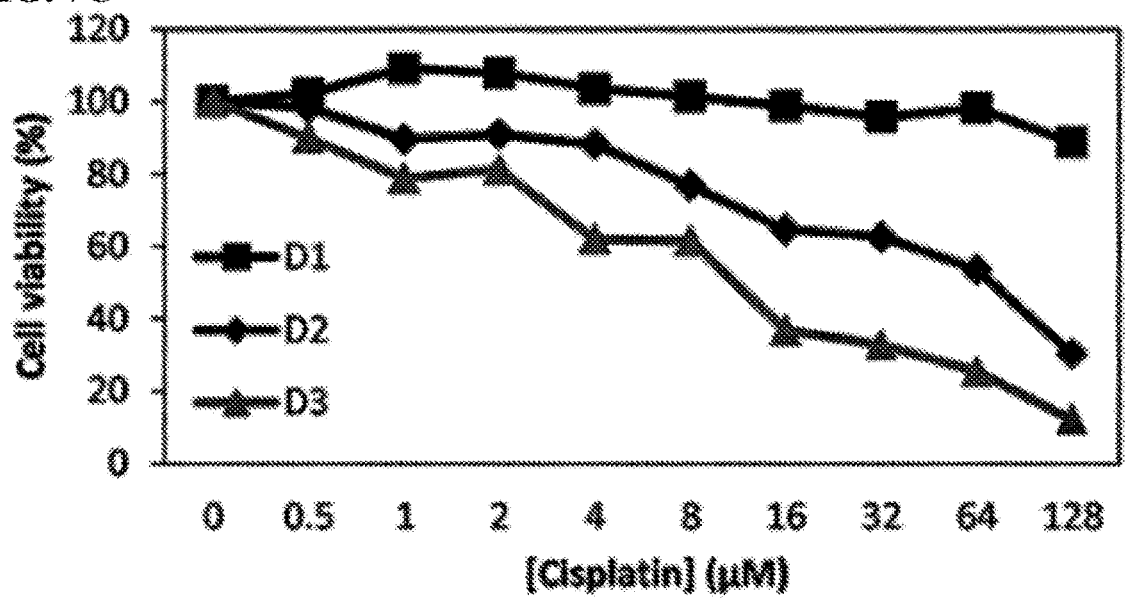
Figure 7D:
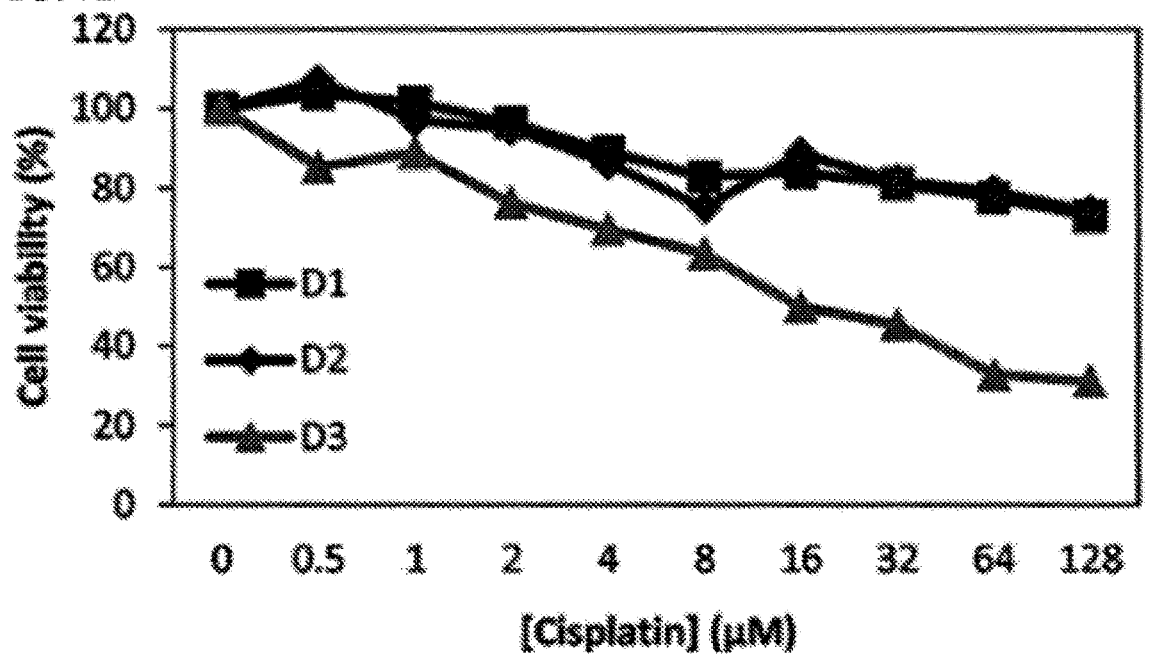
Figure 8:
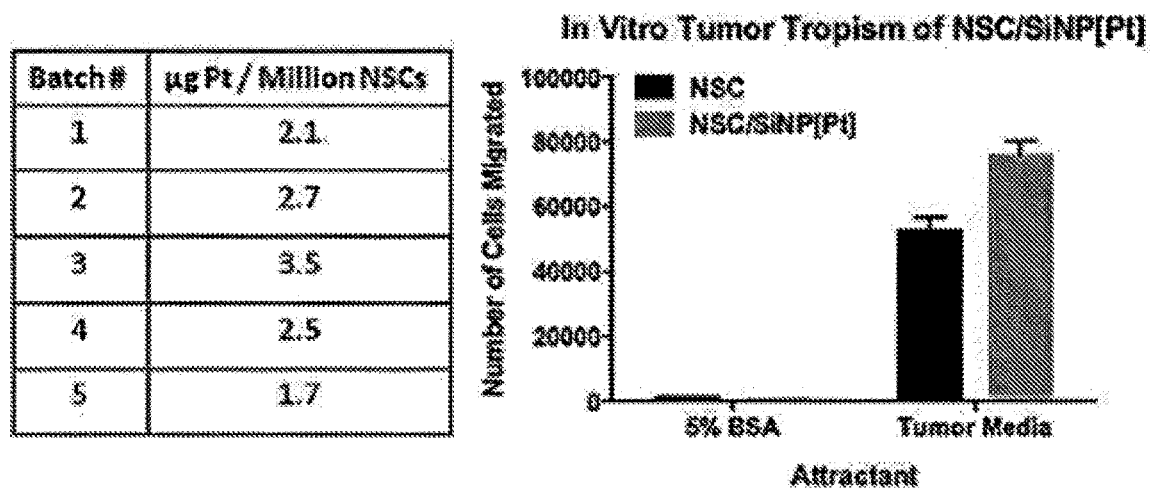
FIG. 8. The loading of NSCs with SiNP-Cis. The cells maintained their tumor tropism after loading.
Figure 9A:
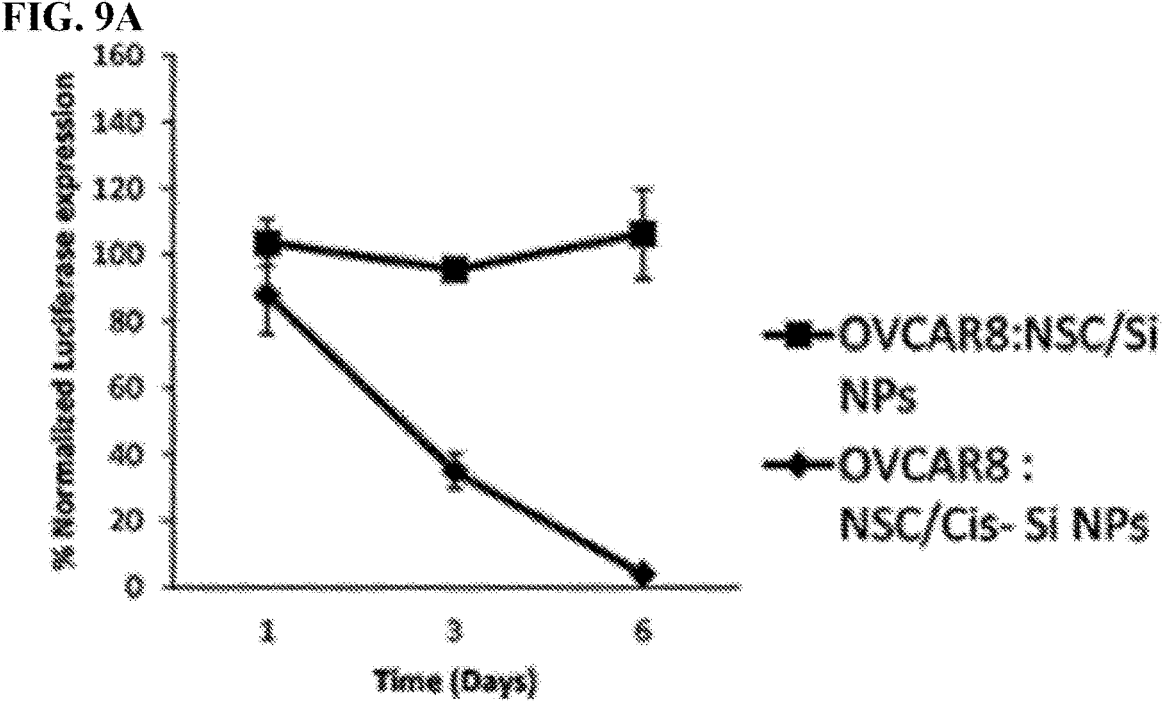
FIGS. 9A-9D. The effects of loaded NSCs on OVCAR 8 cells. The cells were cocultured and the amount of OVCAR8 cells was measured by luciferase imaging. Cells loaded with SiNP-Cis made using 1000 µL TEOS and 300 µL NH$_4$OH (FIGS. 9A-9B) showed good OVCAR8 killing when a DNA-repair inhibitor (VE-822) was added (FIGS. 9A and 9C) but not in the absence (FIGS. 9B and 9D), while SiNP-Cis made using 200 µL TEOS and 500 µL NH$_4$OH (FIGS. 9C-9D) did not show good killing in either condition.
Figure 9B:
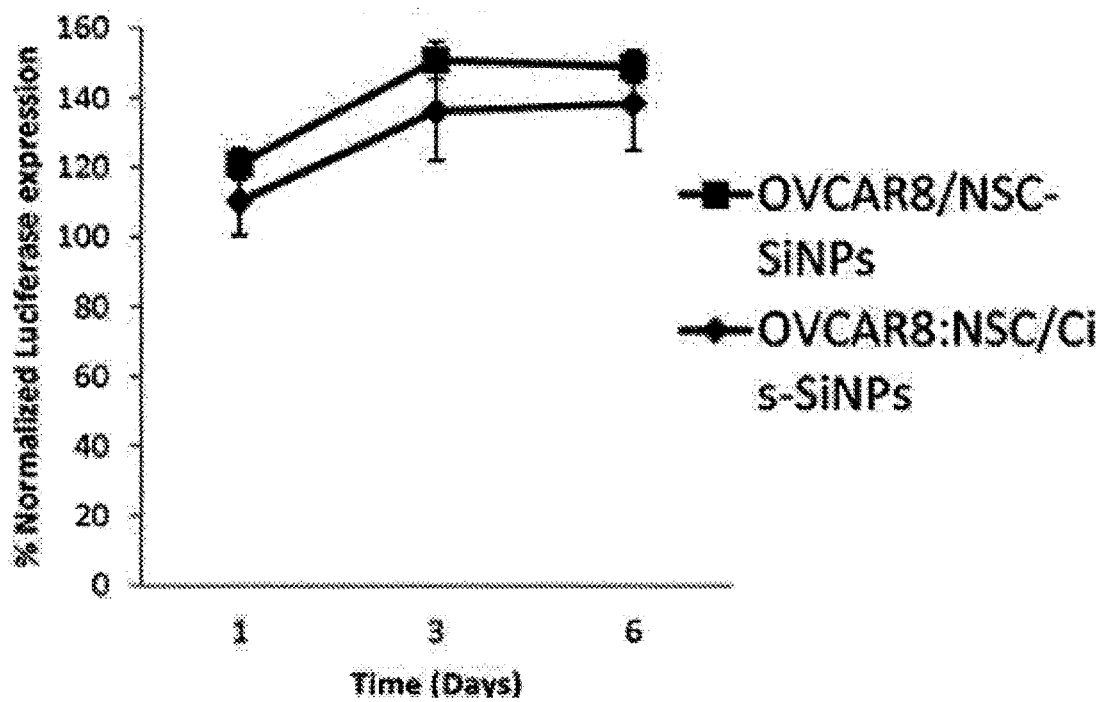
Figure 9C:
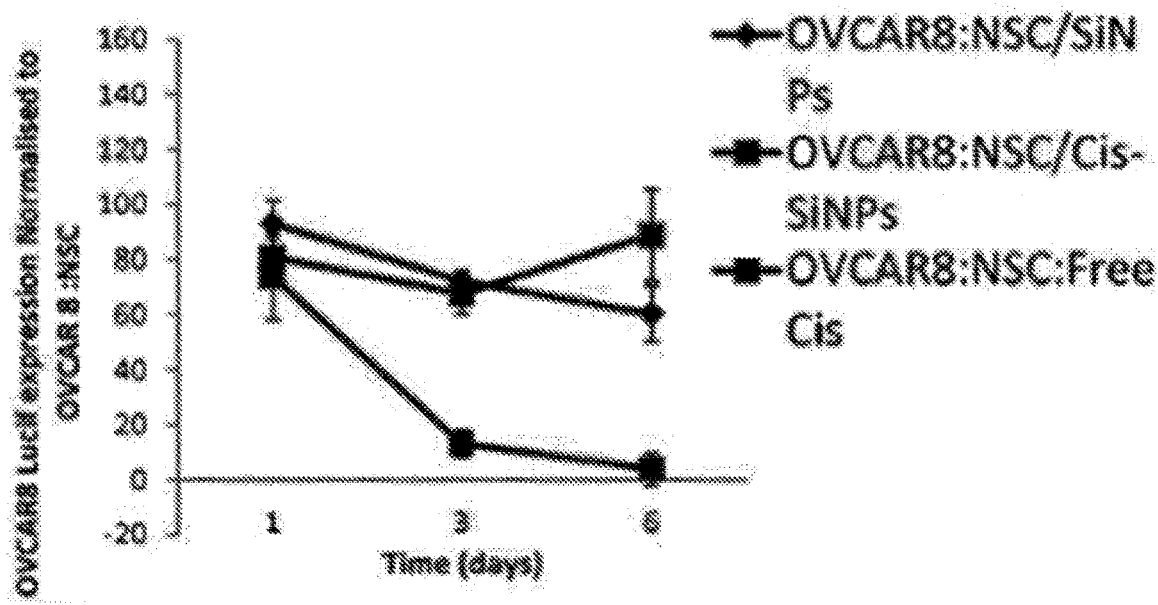
Figure 9D:
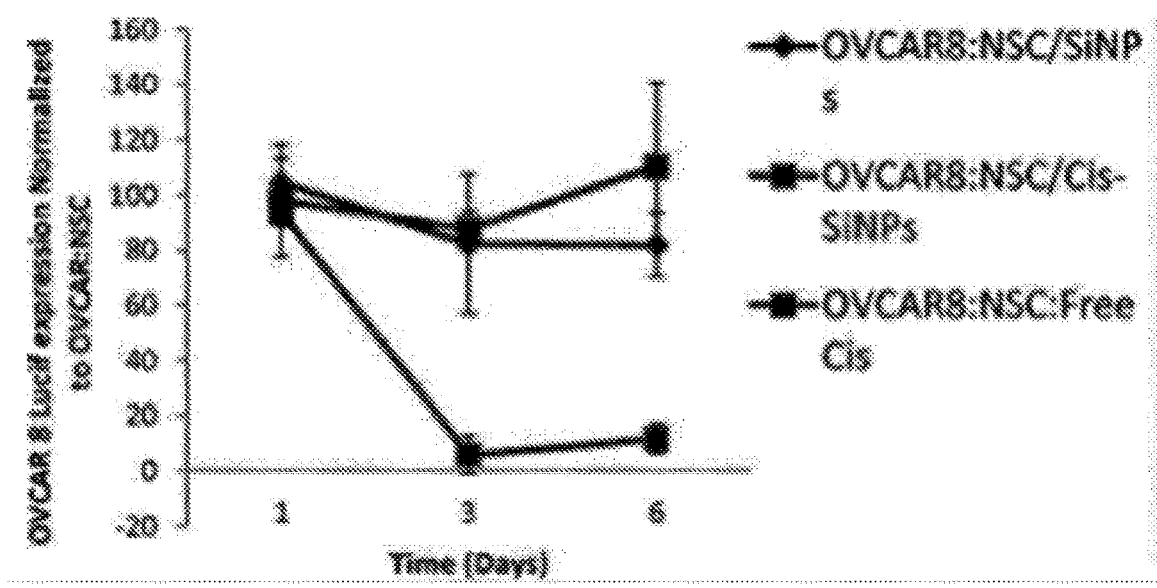
Figure 10:
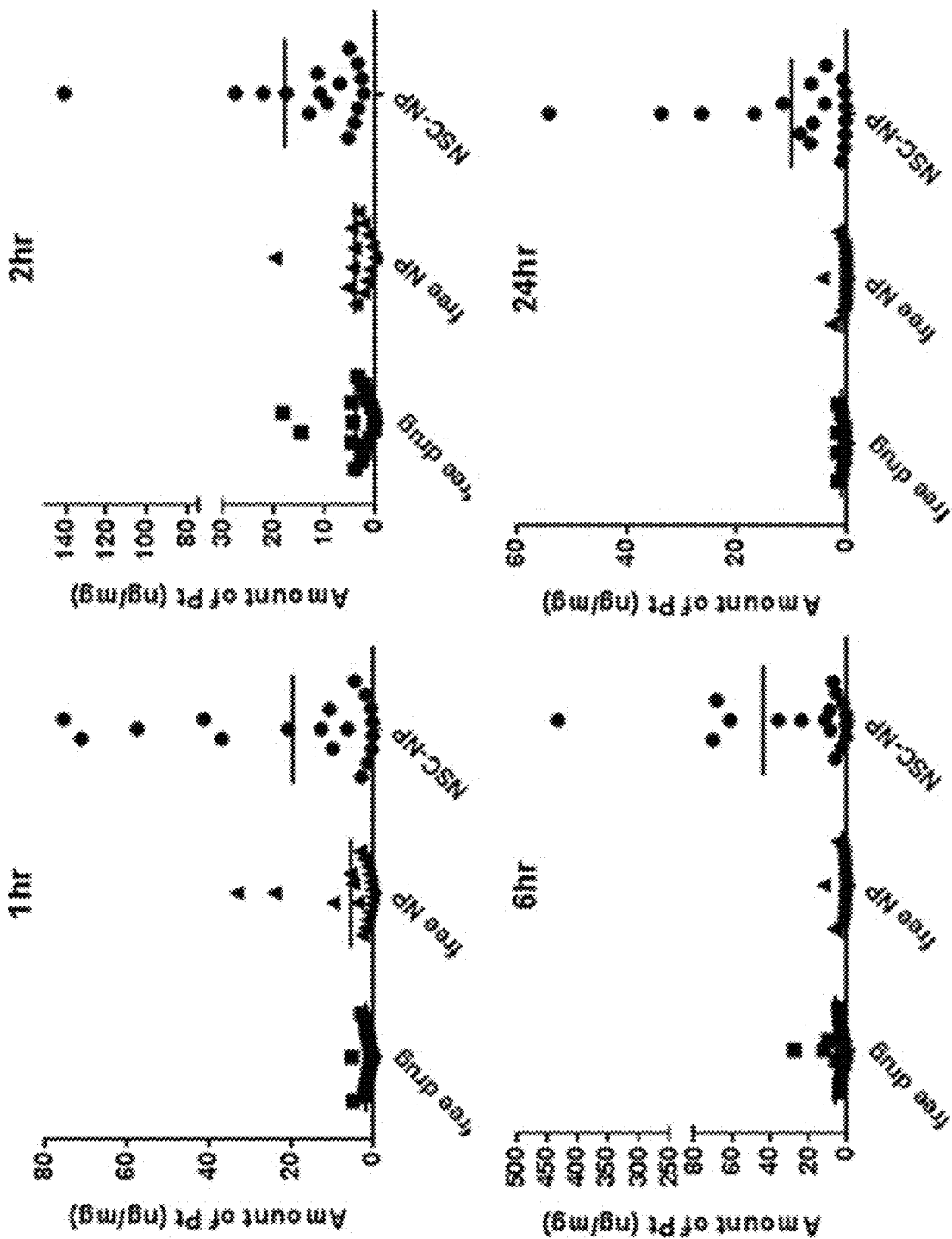
FIG. 10. Results of Pt accumulated at tumors in animal studies. At every time point, tumors from animals injected with NSC+SiNP-Cis showed enhanced accumulation and retention of Pt.
Figure 11A:
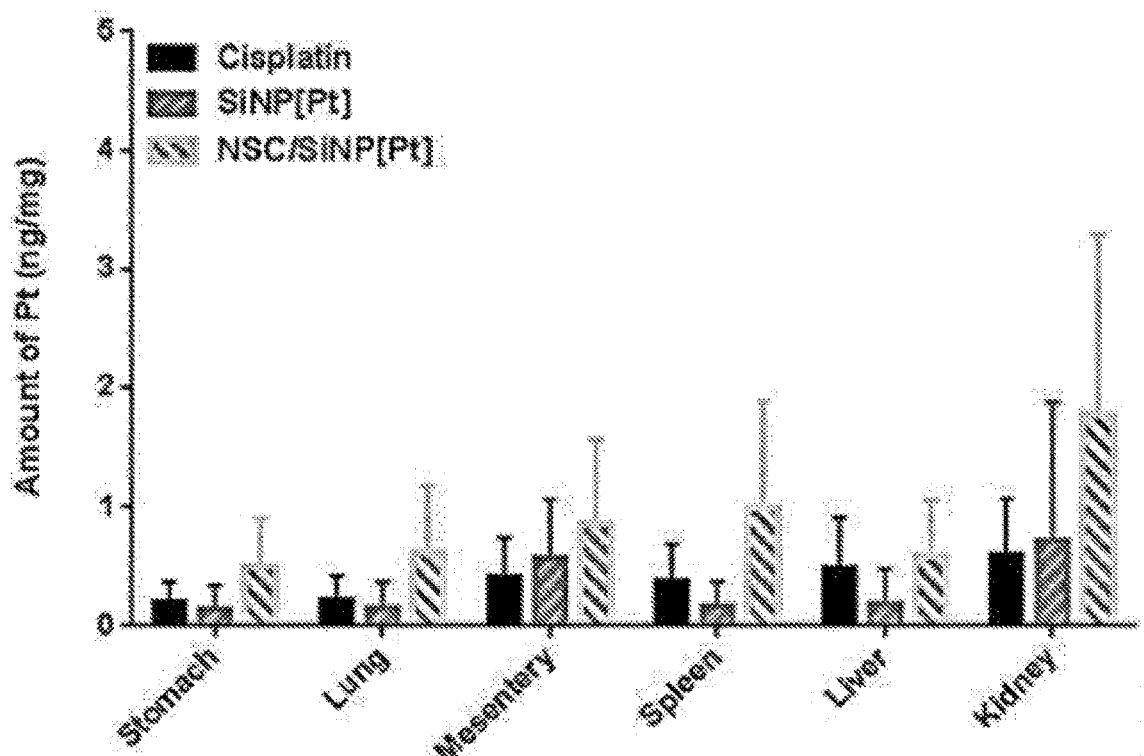
FIGS. 11A-11D. Results of total platinum accumulation at the organs, stomach, lung, mesentry, spleen, liver, and kidney, respectively.
Figure 11B:
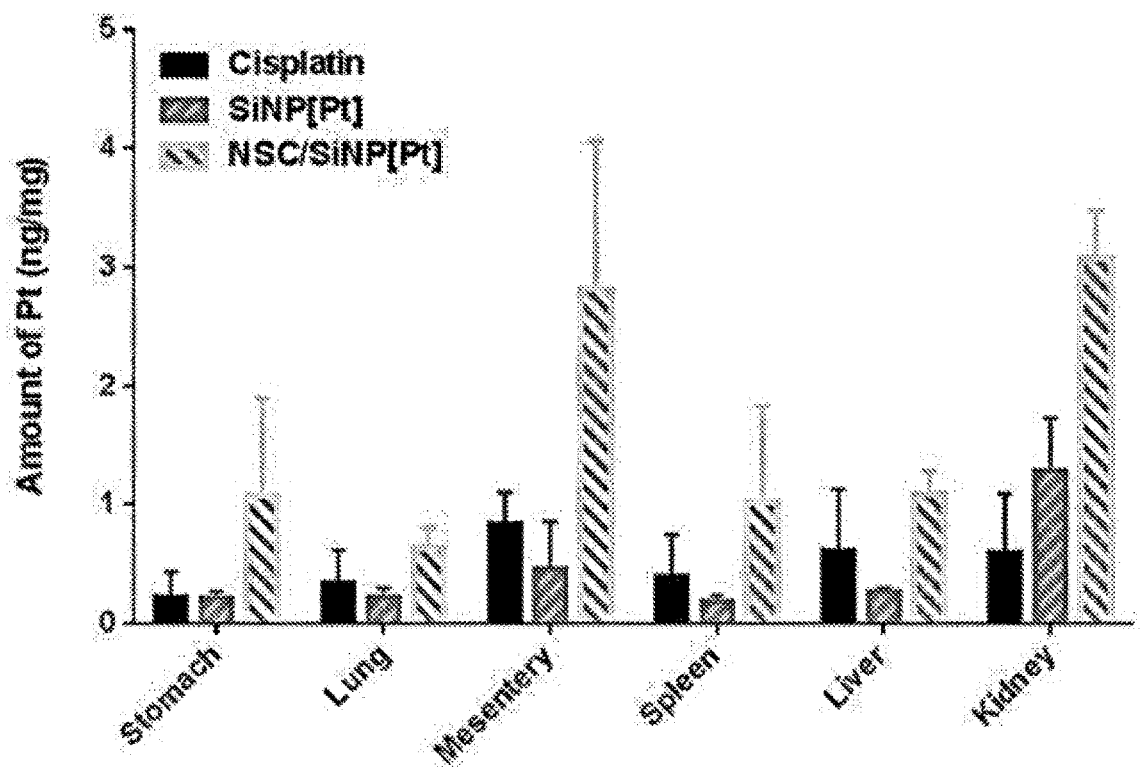
Figure 11C:
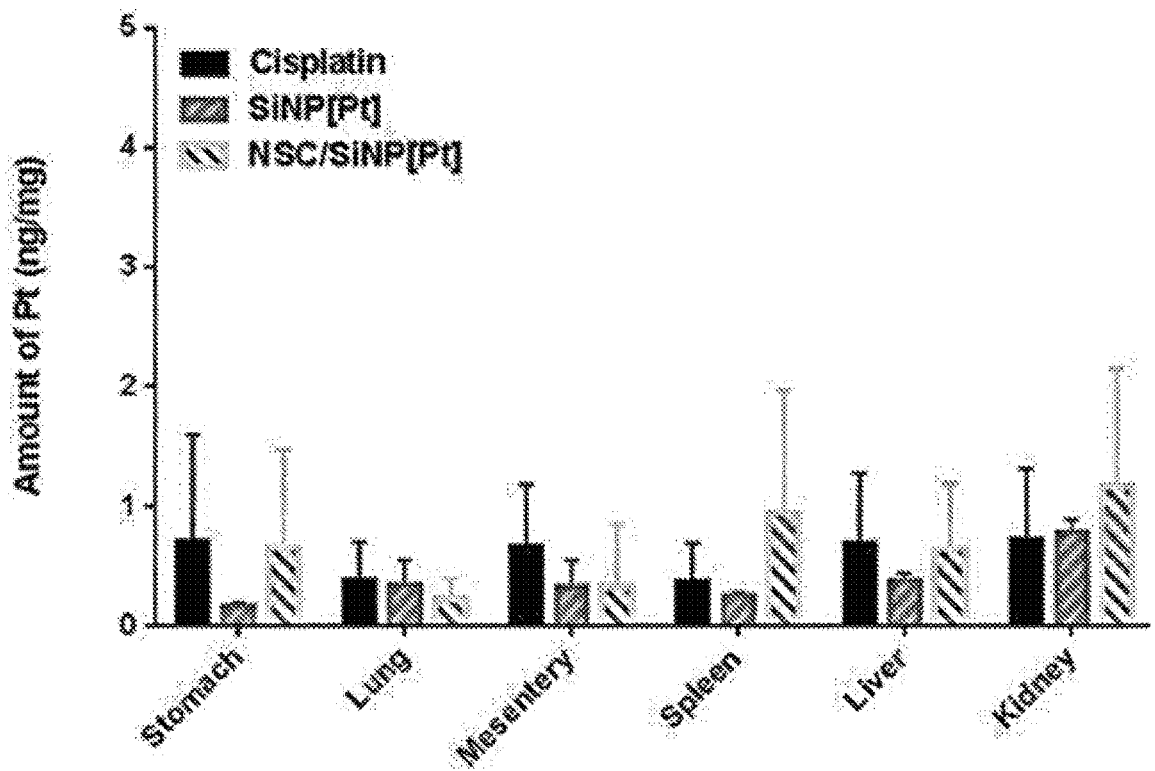
Figure 11D:
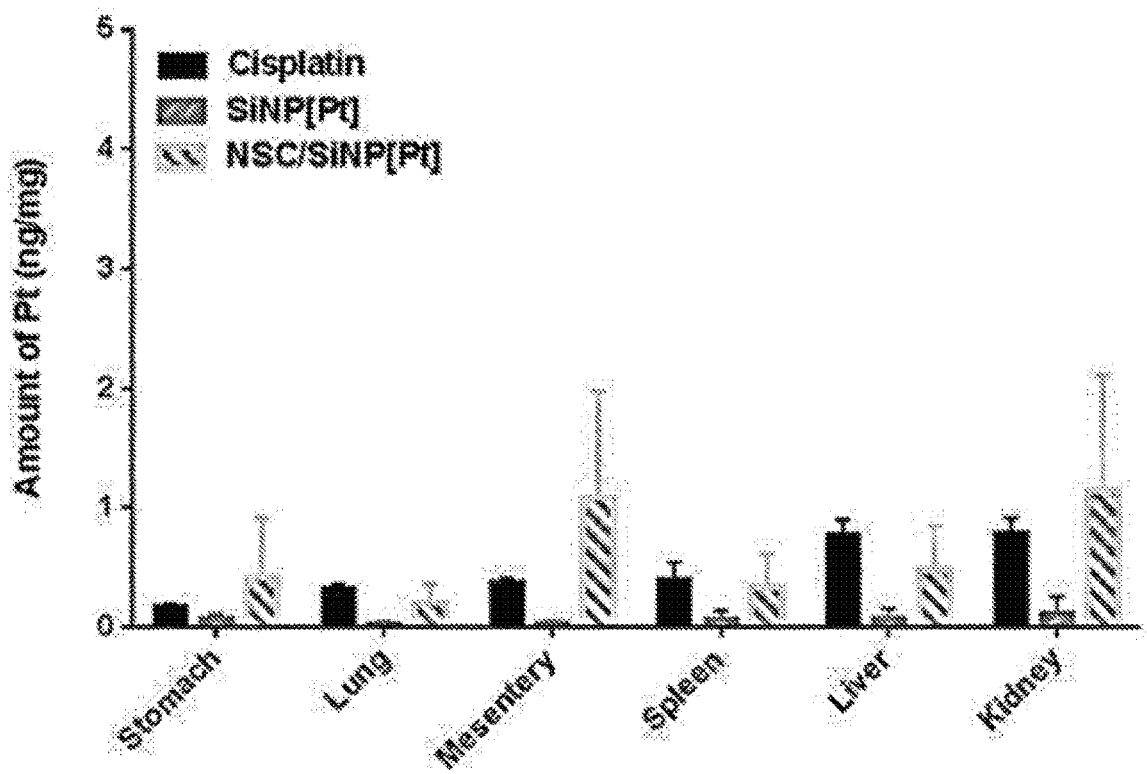
Figures 12, 13A:
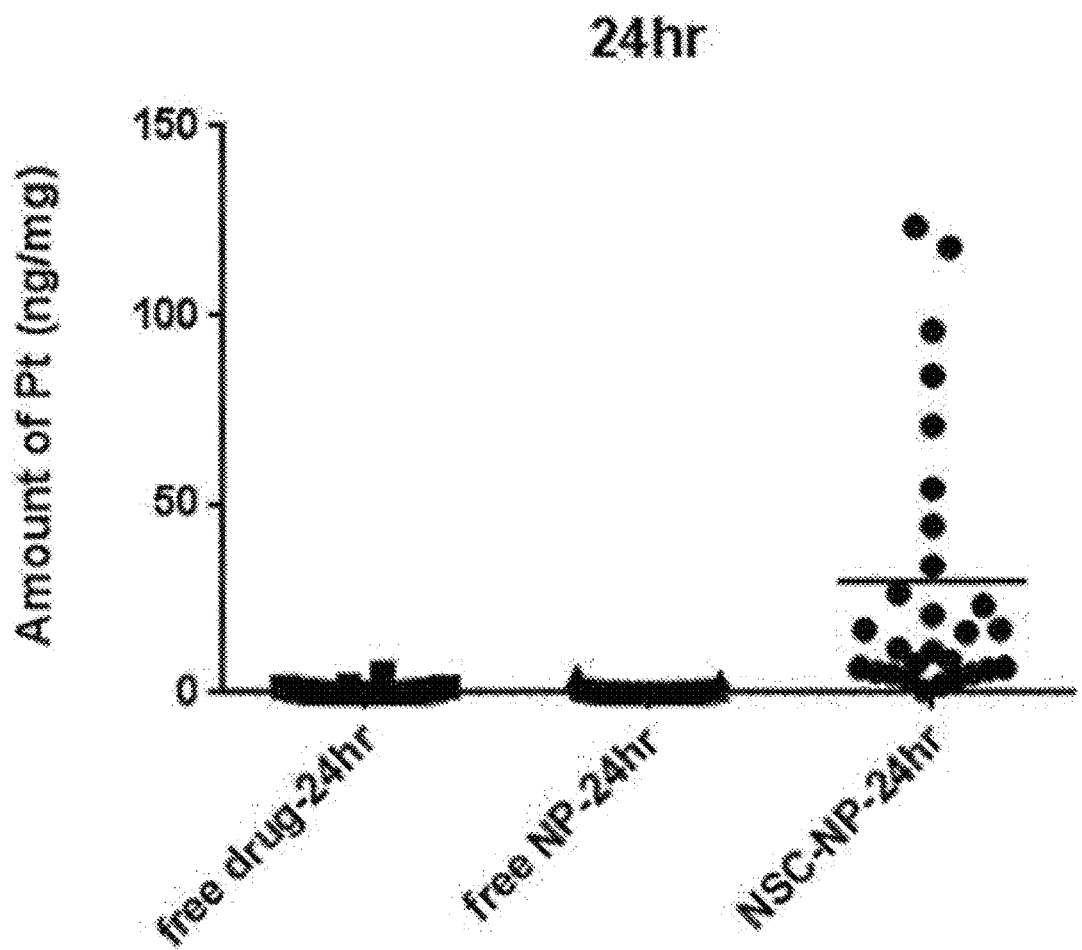
FIG. 12. Results of the total amount of Pt accumulated at tumors after 24 hrs, the combined result of 2 animal studies.
FIGS. 13A-13C. The experimental synthesis scheme showing the bare silica nanoparticle (SiNP—OH) and how it can be functionalized with functional groups, or with polymers such as polyethylene glycol, or a combination of polyethylene glycol with functional groups. Tables show the ratios of polymers/functional groups tested, including preferred ratios of non-functional PEG:functionalized PEG.
Figure 13B:
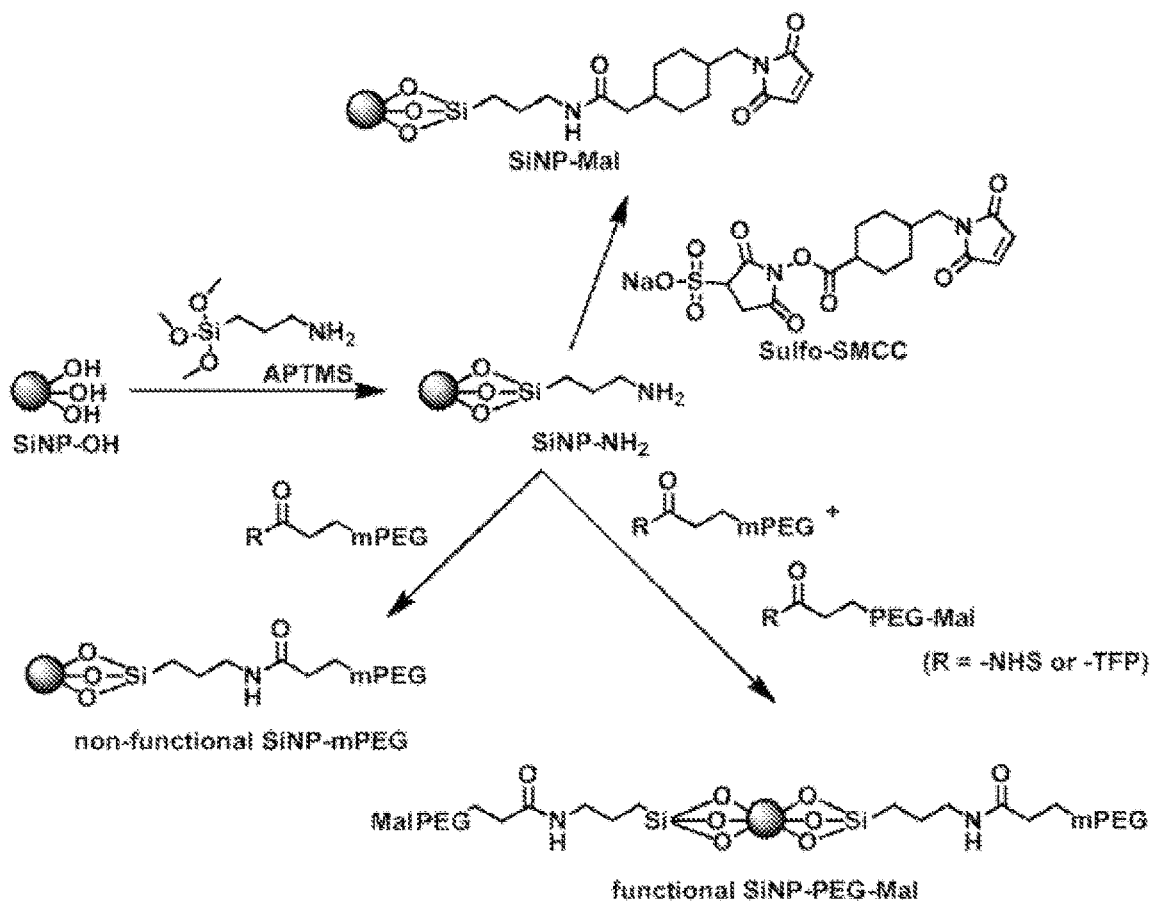
Figure 13C:
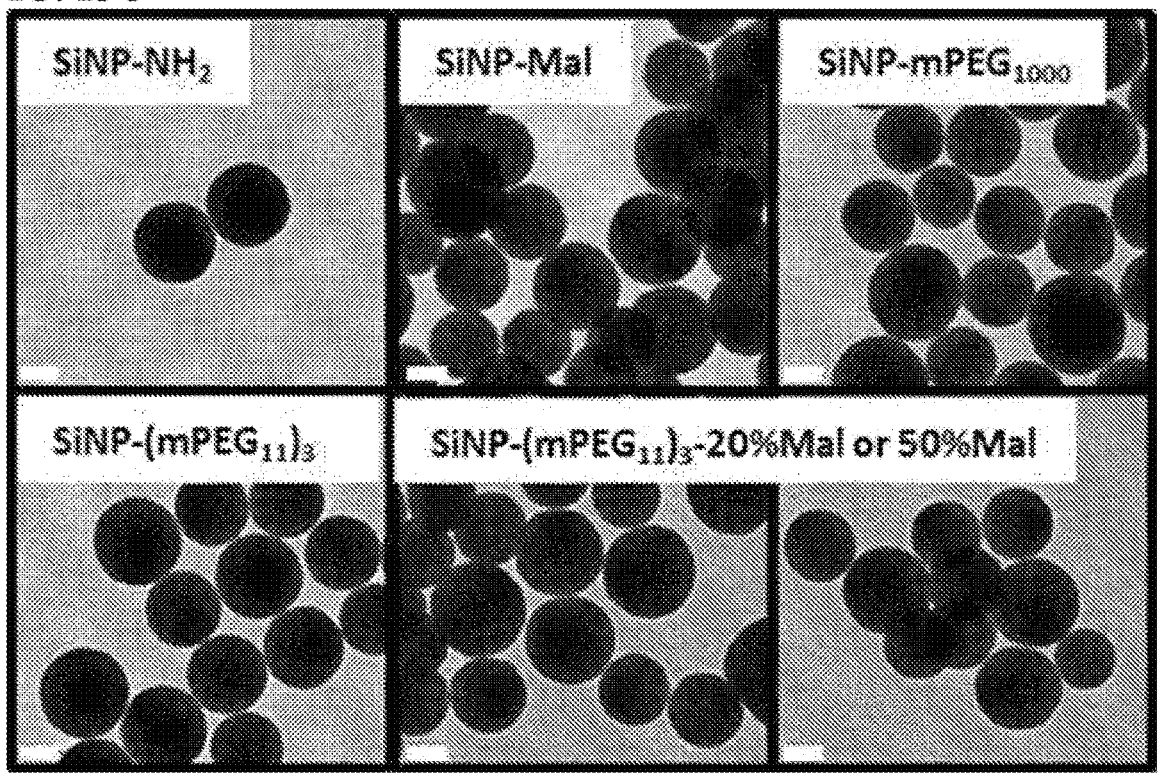
Figure 14:
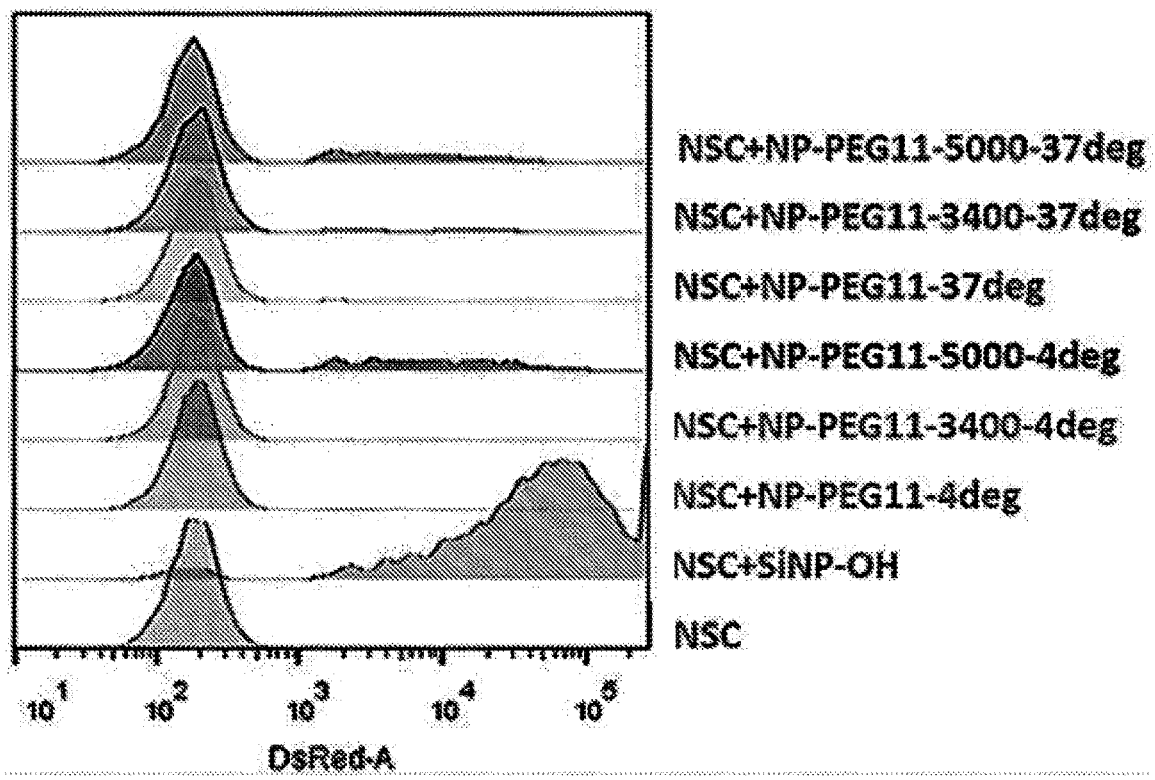
FIG. 14. Cell labeling results determining the preferred ratio of non-functional PEG:functionalized PEG.
Figure 15:
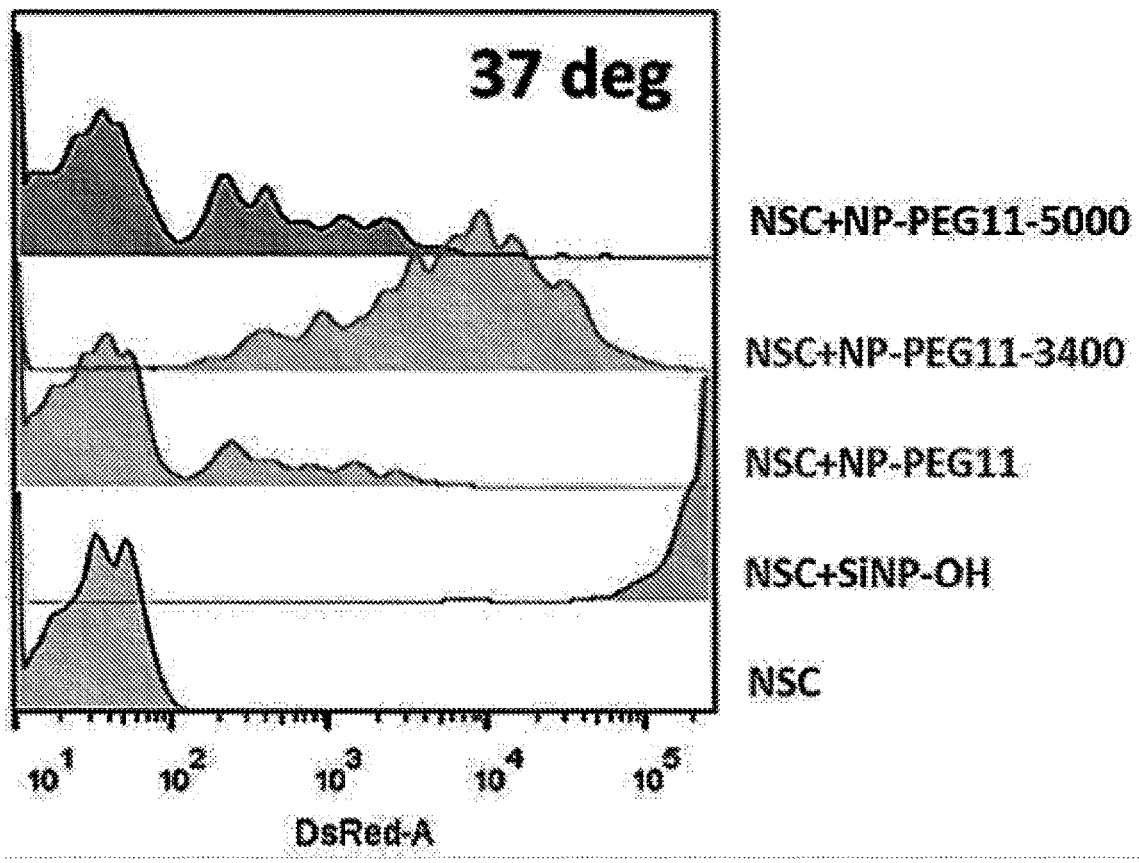
FIG. 15. Cell labeling results determining the preferred ratio of non-functional PEG:functionalized PEG.
Figure 16:
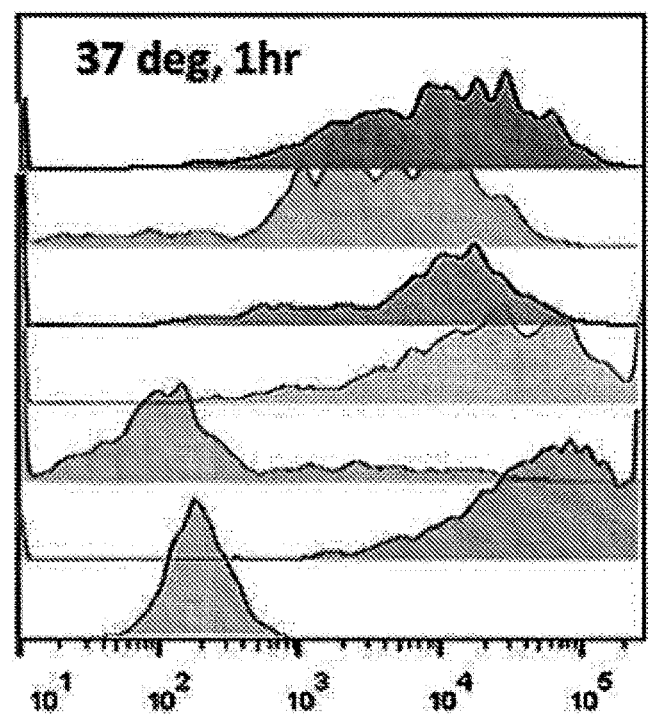
FIG. 16. Further optimizations of cell labeling studies. It appears that labeling NSCs via functionalized PEGylated SiNPs reaches a limit. NP attachment to the cell surface will eventually plateau as more NPs conjugate to cells. At 50%:50% composition, there was not much difference in the size of functional Mal-PEGs while making functional SiNPs. Mal-PEG2000 and Mal-PEG3400 appear to work better than Mal-PEG5000. At 80%:20%, Mal-PEG2000 is preferred over Mal-PEG3400 and Mal-PEG5000 as it was able to label NSCs efficiently.
Figure 17A:
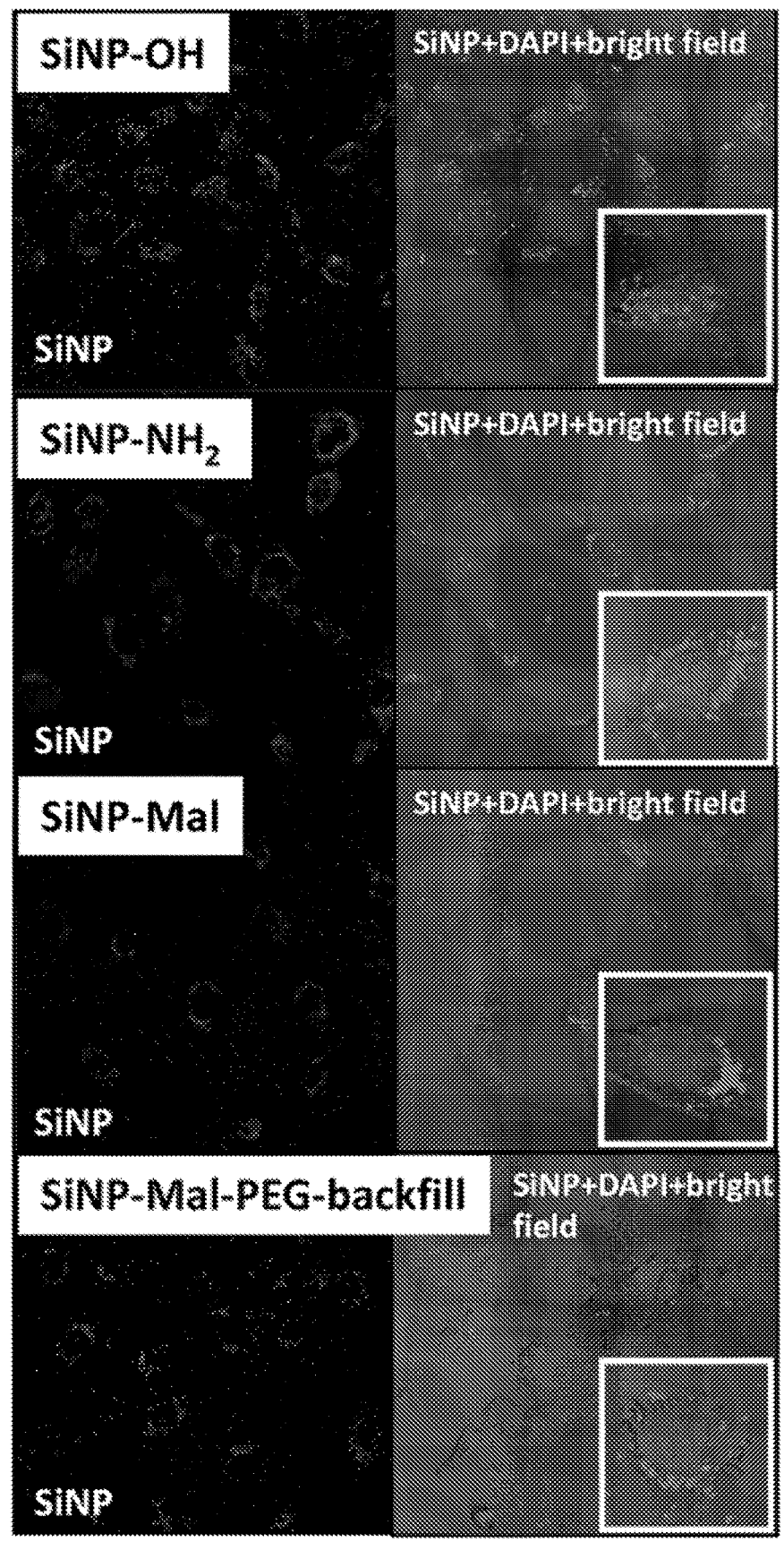
FIGS. 17A-17D. Confocal images of NSCs labeled with functional PEG-SiNPs. For bare SiNPs (SiNP—OH), those functionalized with surface amines (SiNP—NH$_2$), those further derivatized with surface maleimides (SiNP-Mal), they were internalized by NSCs most likely via endocytosis as these NPs were located in the perinuclear space (the circle near the nuclei), an indicator of internalization by endocytosis. This was also true when SiNP-Mal was used and then PEG thiol was added after incubation (SiNP-Mal-PEG-backfill). For PEGylated SiNPs, little association with the cells was seen. For PEGylated SiNPs also functionalized with functional groups, SiNPs were associated with the cells but were not found in the perinuclear space, indicating there were most likely attached to the surface of the cells without being internalized.
Figure 17B:
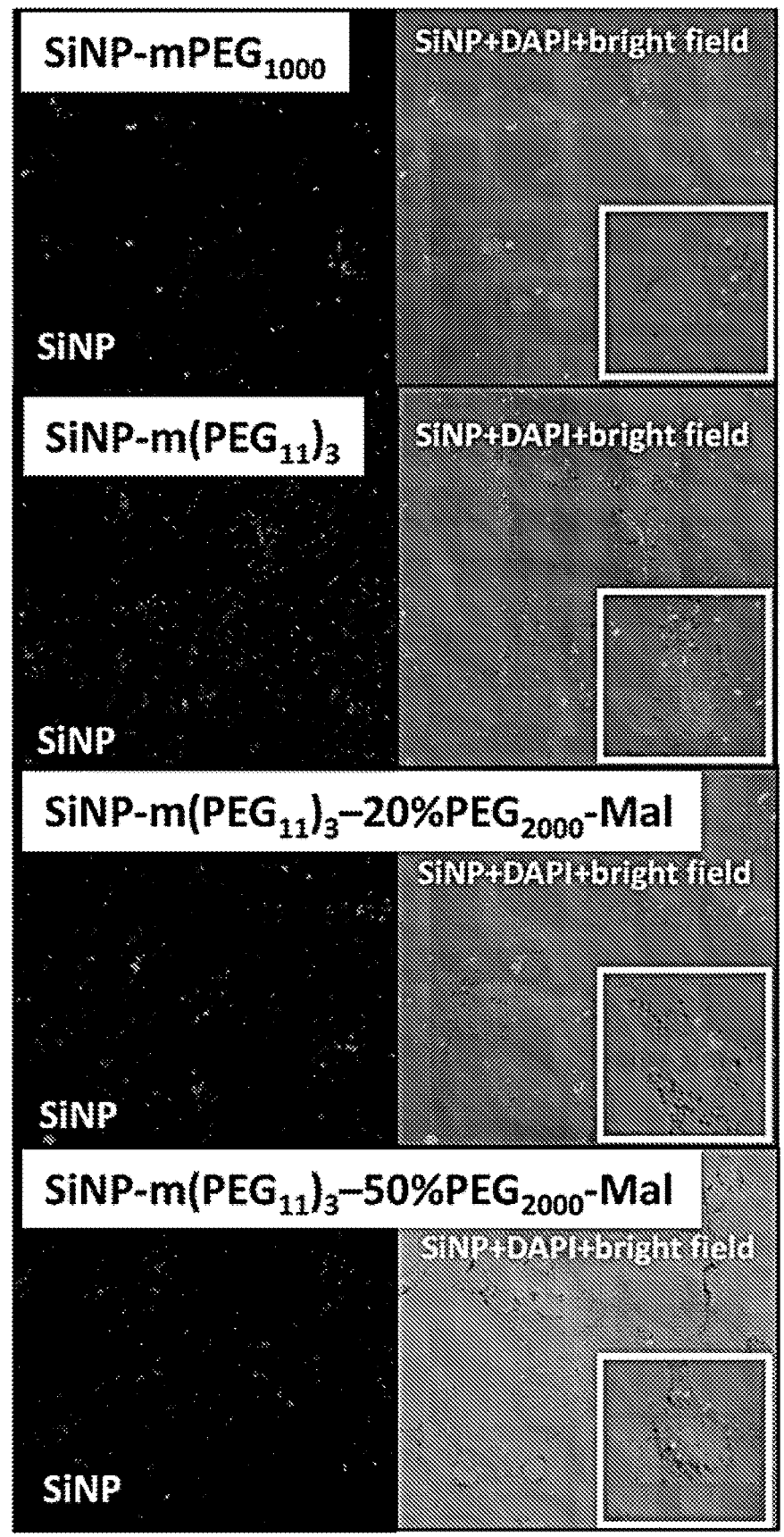
Figure 17C:
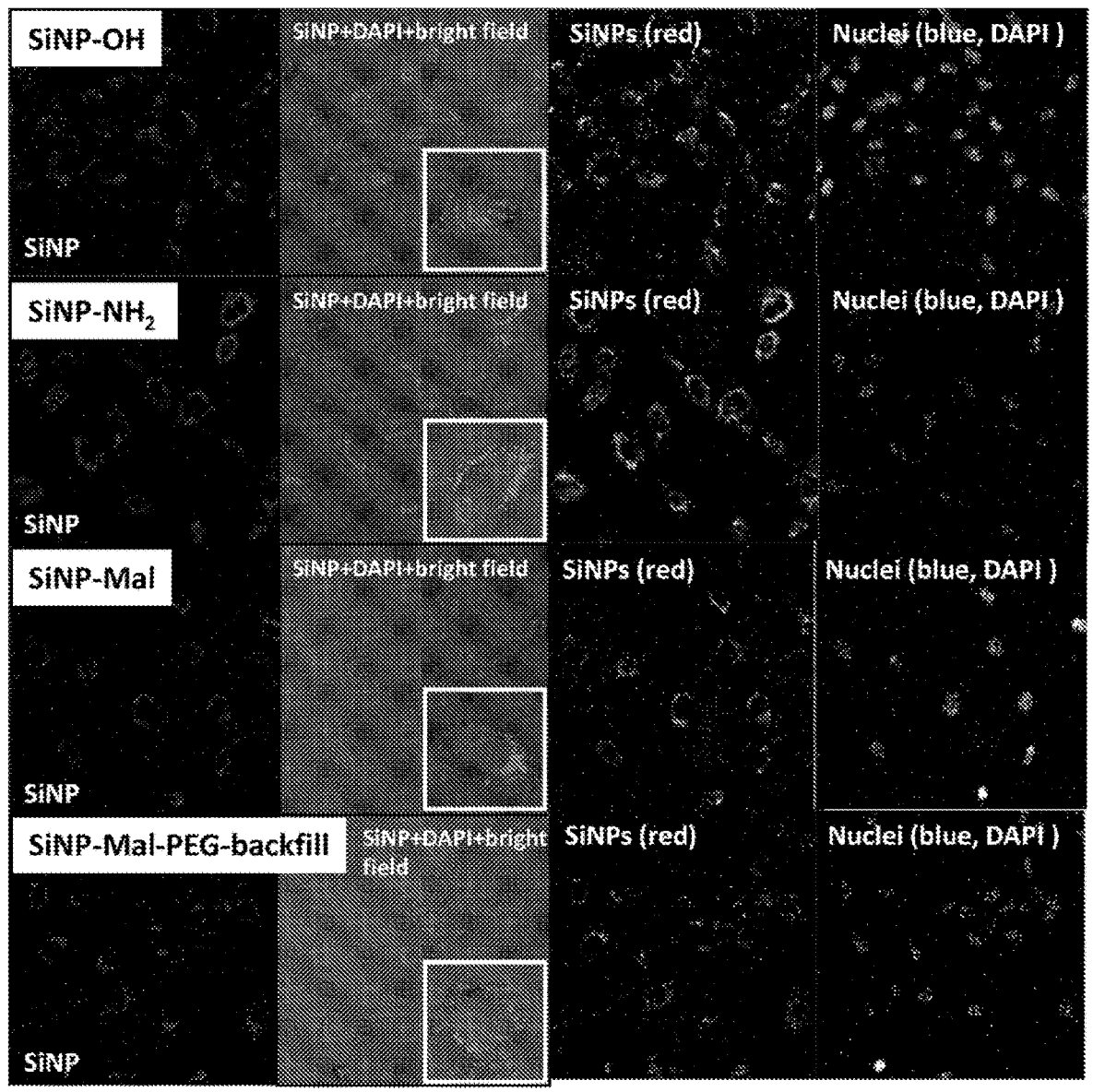
Figure 17D:
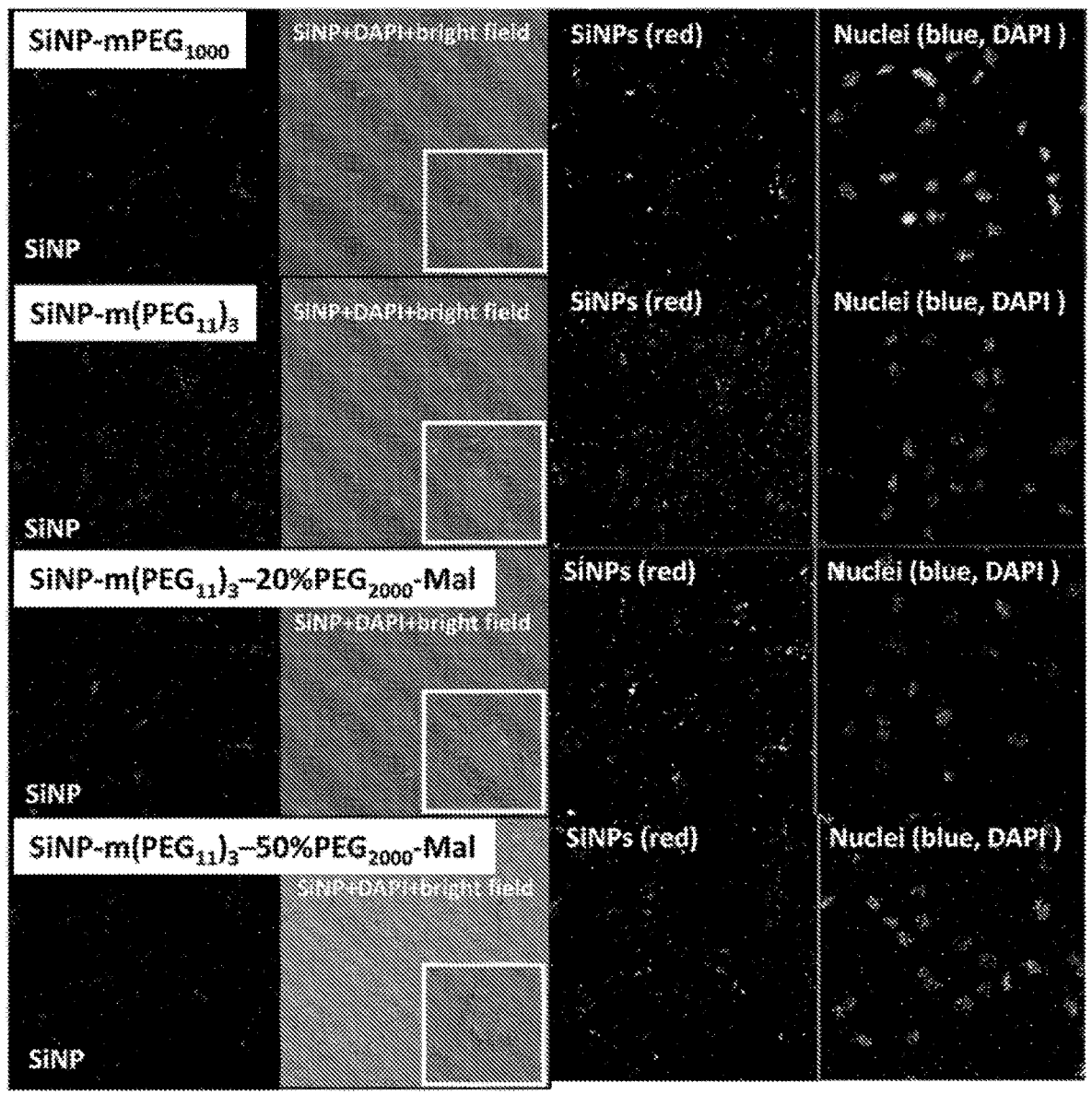
Figure 18A:
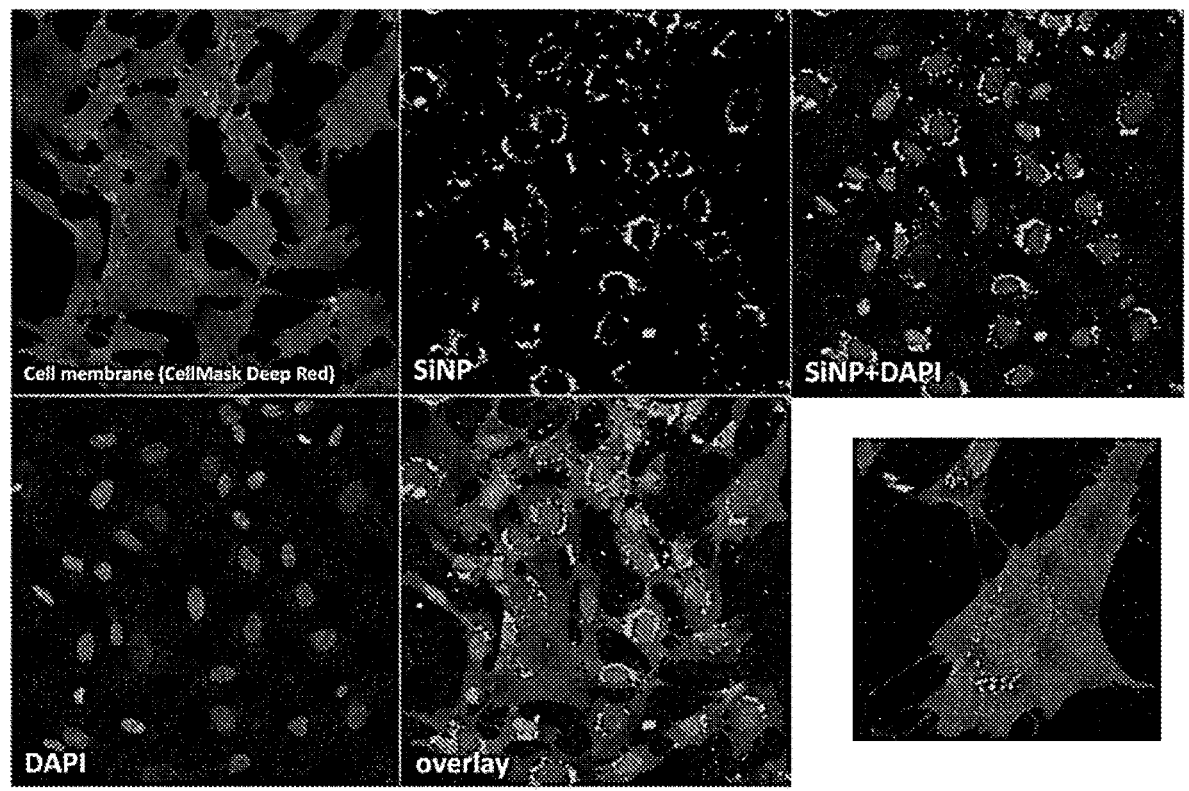
FIGS. 18A-18B. Confocal images and 3D reconstruction of NSCs labeled with functional PEG-SiNPs after 24 hours, specifically NSC+SiNP-Mal.
Figure 18B:
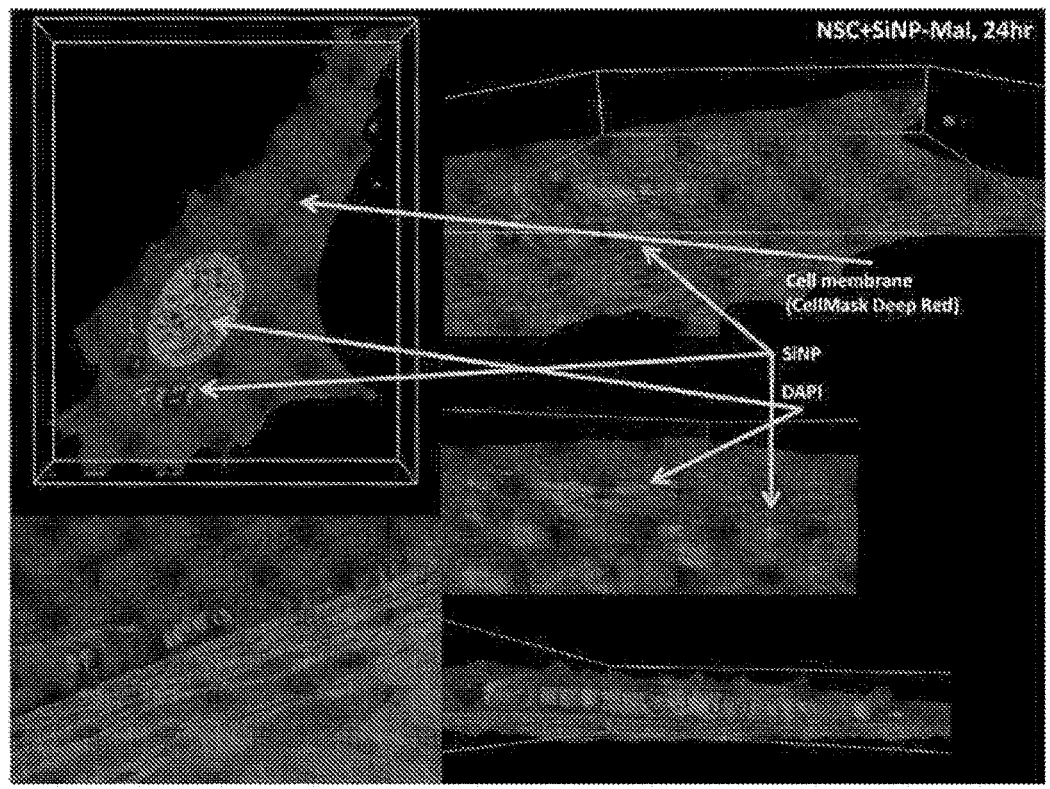
Figure 19A:
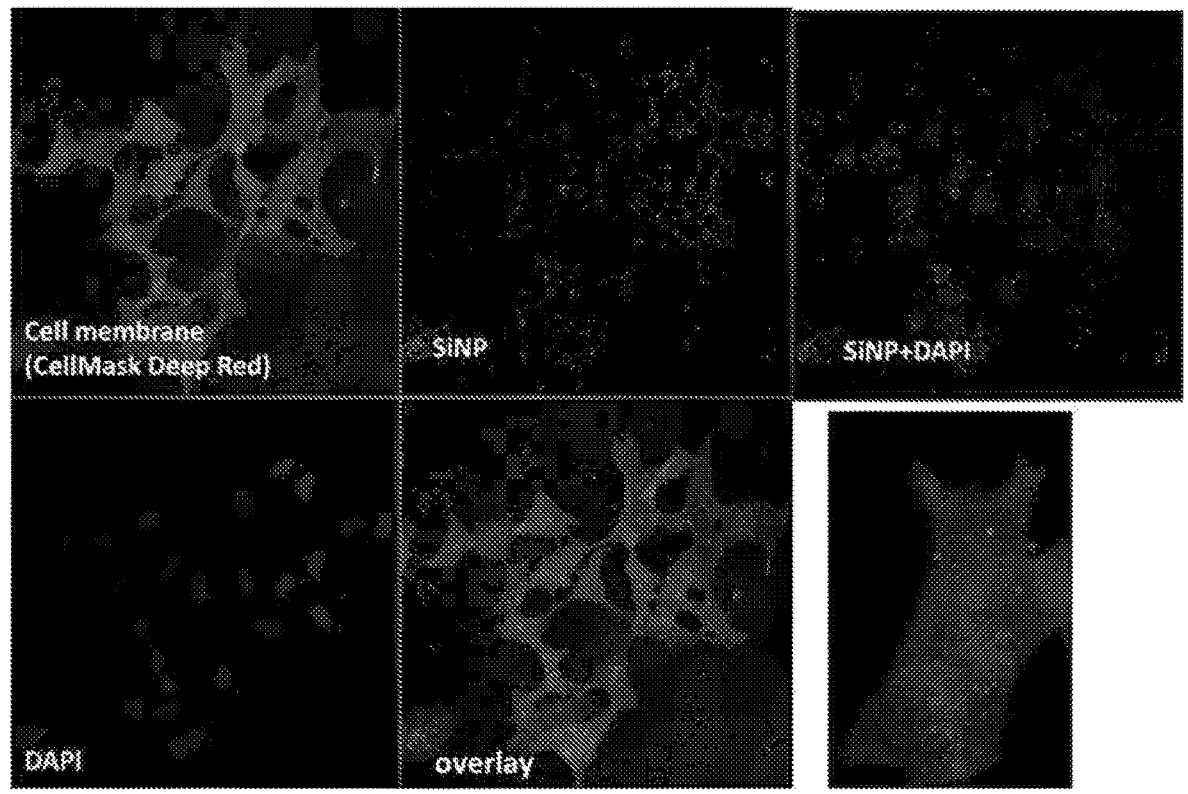
FIGS. 19A-19C. Confocal images and 3D reconstruction of NSCs labeled with functional PEG-SiNPs after 24 hours, specifically NSC+SiNP-(PEG$_{11}$)$_3$-20% Mal.
Figure 19B:
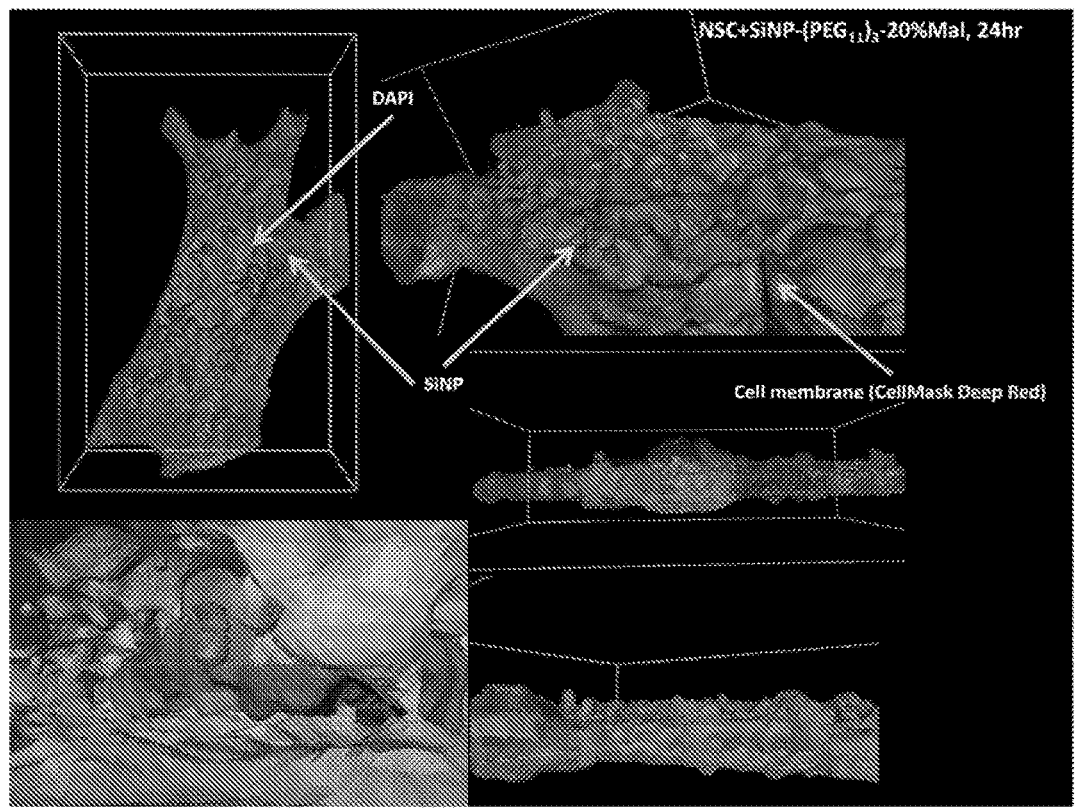
Figure 19C:
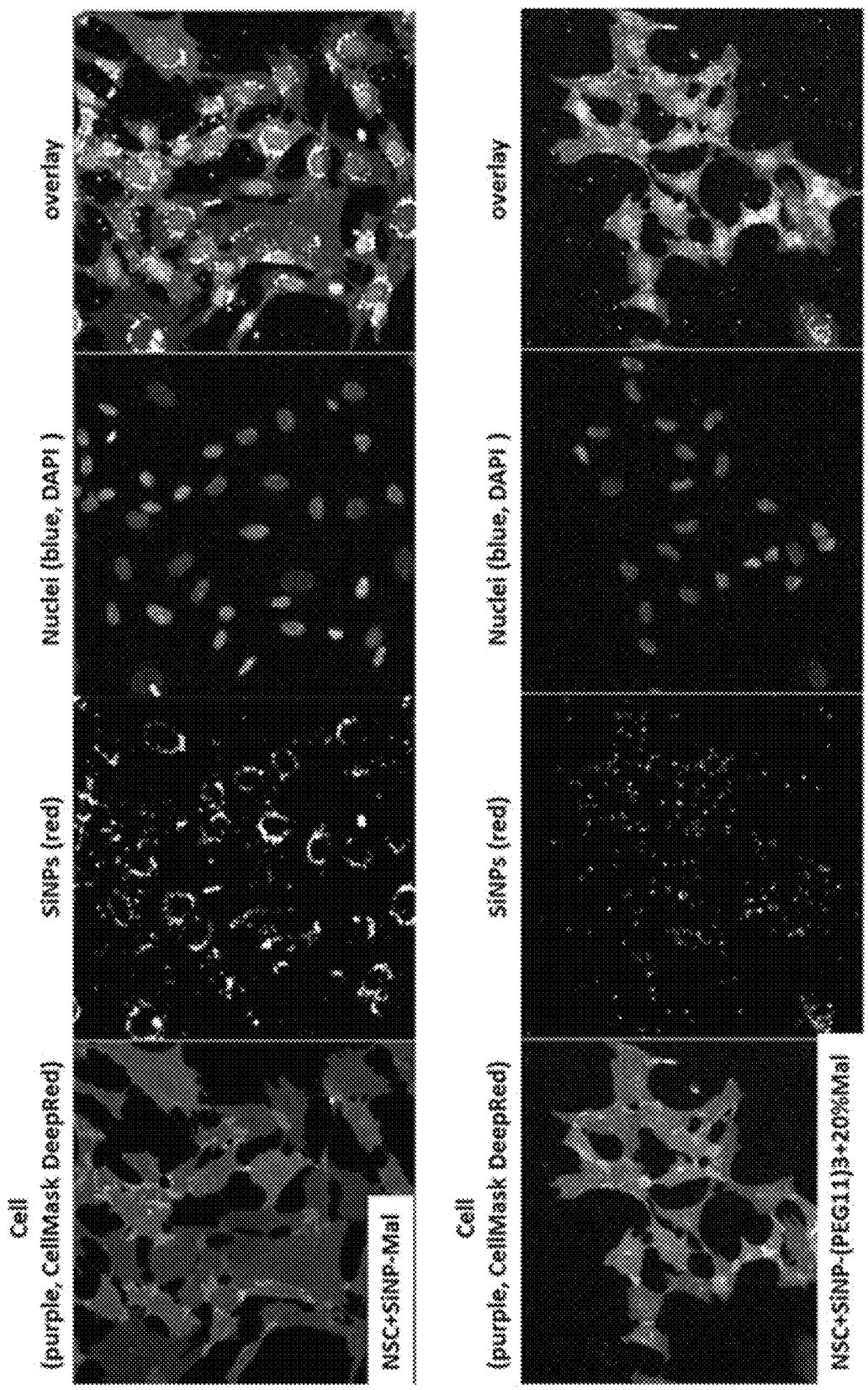
Figure 20:
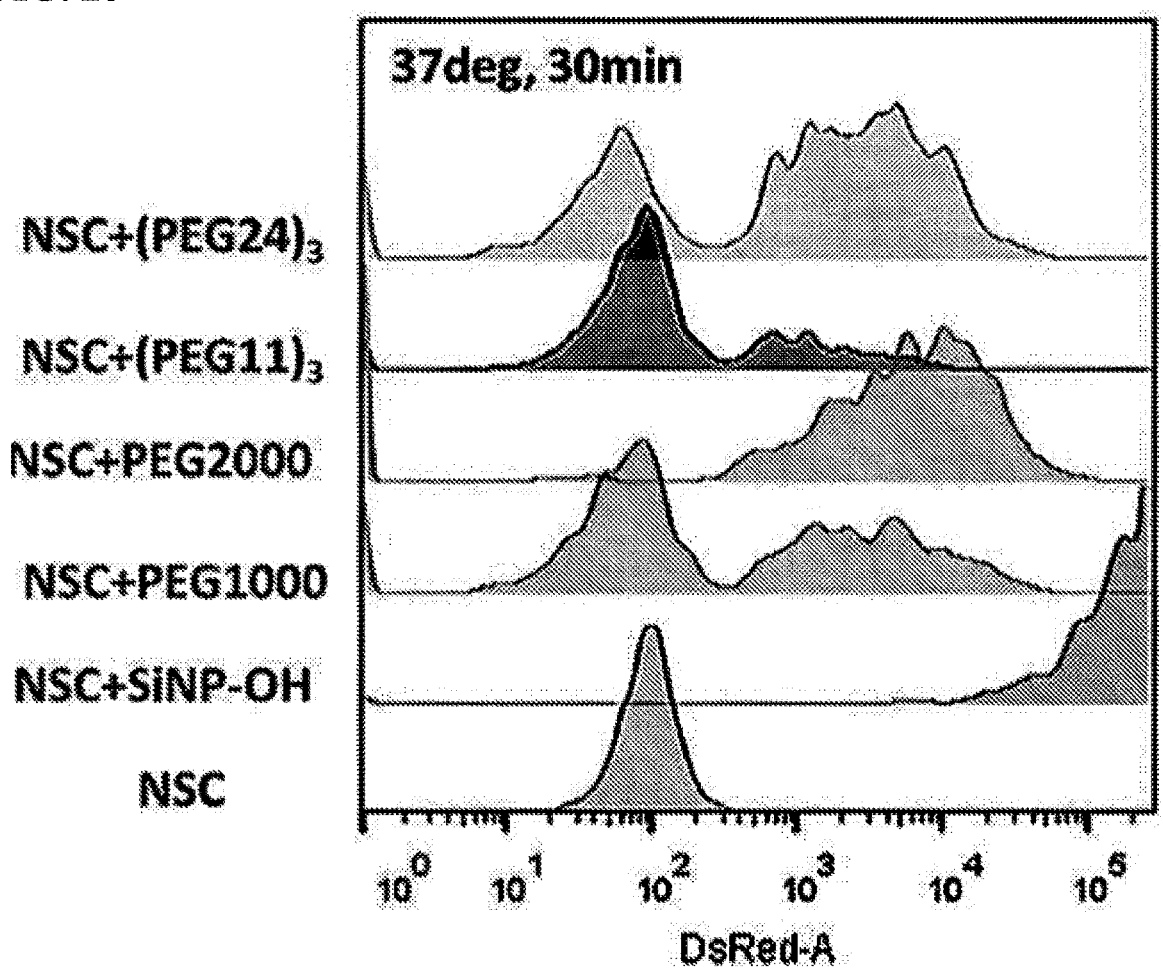
FIG. 20. Cell labeling with bare and PEGylated silica nanoparticles. Comparing the PEGs, PEG$_{1000}$ vs. PEG$_{2000}$, (PEG$_{11}$)$_3$ vs. (PEG$_{24}$)$_3$, it appears that shorter PEGs perform better at reducing the non-specific binding of SiNPs to cells as cells had lower level of red fluorescence. Comparing the structure of the PEGs, linear vs. branched, branched PEGs, (PEG$_{11}$)$_3$ and (PEG$_{24}$)$_3$ work better than the linear PEGs, PEG$_{1000}$ and PEG$_{2000}$. Overall, (PEG$_{11}$)$_3$ is preferred at preventing non-specific binding of the SiNPs to NSCs.

Cell labeling study for SEM images, as observed in FIG. 2. 1. Take 2 small, circular cover glasses, sterilize them by soaking them in absolute EtOH overnight. 2. Take the cover glasses out of EtOH using tweezers, once dried, flame them over the fire. 3. Put each cover glass in a 24-well plate well, close the lid, leave the plate under UV light for 10 min. 4. Add 0.33M NSCs in 0.5 mL of media to each well with cover glass. Let the cells adhere overnight. 5. Next day, remove the old media. Cells were washed once with PBS. 6. Treat cells with NPs (SiNP—OH, 1 uL; SiNP-Mal, 2 uL) in 0.5 mL DMEM media without amine or free thiol groups, incubate at 4° C. for 30 min. 7. Remove the media, wash cells once with PBS 8. Fix the cells with 1 mL of 2% glutaraldehyde in each well, leave samples in the fixing solution for 1 hr at r.t. 9. Samples were dried and stained for SEM imaging.

TABLE 1

Library of polyethylene glycol (PEG) used to coat the nanoparticle surface.

| Linear PEGs | Branched PEGs |
|---|---|
| mPEG$_{400}$—SH | TFP-(m-dPEG$_{11}$)$_3$ |
| mPEG$_{1000}$—SH | NHS-(m-dPEG$_{24}$)$_3$ |
| mPEG$_{1000}$—NSH | |
| mPEG$_{2000}$—SH | |
| mPEG$_{2000}$—NSH | |
| Mal—PEG$_{2000}$—NSH | |
| Mal—PEG$_{3400}$—NSH | |
| mPEG$_{5000}$—SH | |
| Mal—PEG$_{5000}$—NSH | |

Functionalizing silica nanoparticles terminated with -Mal with linear PEGs selected from Table 1. SiNP-Mal in MilliQ was washed 3 times with PBS to convert their solvent to PBS followed by the addition of a PEG-SH solution in PBS. The mixture was placed in a shaker and incubated at 37° C. overnight. It was assumed that each maleimide group on the NP surface takes up 0.6 nm$^2$ and each maleimide functional group reacts with one thiol group on the PEG-SH molecules. To maximize PEG coverage on the NP surface, 10-fold molar excess of PEG-SH to the number of maleimide groups on the SiNP surface was used in the reaction. Upon reaction completion, PEGylated SiNPs were collected and washed by repeated centrifugation at 21,000 g for 1 min (3 times with MilliQ water). PEGylated SiNPs were resuspended in MilliQ water and stored at 4° C.

Functionalizing silica nanoparticles terminated with —NH$_2$ with branched PEGs selected from Table 1. SiNP—NH$_2$ in MilliQ was washed 3 times with PBS to convert their solvent to PBS followed by the addition of a TFP-(PEG$_{11}$)$_3$ or N-Hydroxysuccinimide-(PEG$_{24}$)$_3$ solution in PBS. Note N-Hydroxysuccinimide is alternatively written as NHS. The mixture was placed in a shaker and incubated at 37° C. overnight. It was assumed that each amine group NH$_2$— on the NP surface takes up 0.6 nm$^2$ and each amine functional group reacts with one activated ester group (TFP- or N-Hydroxysuccinimide-) on the branched PEG molecules. To maximize PEG coverage on the NP surface, 10-fold molar excess of PEG to the number of amine groups on the SiNP surface was used in the reaction. Upon reaction completion, PEGylated SiNPs were collected and washed by repeated centrifugation at 21,000 g for 1 min (3 times with MilliQ water). PEGylated SiNPs were resuspended in MilliQ water and stored at 4° C.

Functionalizing silica nanoparticles terminated with —NH$_2$ with functionalized-PEGs. SiNP—NH$_2$ in MilliQ was washed 3 times with PBS to convert their solvent to PBS followed by the addition of a mixture of TFP-(PEG$_{11}$)$_3$ and N-Hydroxysuccinimide-PEG-Mal solution in PBS. The mixture was placed in a shaker and incubated at 37° C. overnight. It was assumed that each maleimide group on the NP surface takes up 0.6 nm$^2$ and each maleimide functional group reacts with one thiol group on the PEG-SH molecules. To maximize PEG coverage on the NP surface, 10-fold molar excess of Mal-PEG-NHS to the number of amine groups on the SiNP surface was used in the reaction. Upon reaction completion, PEGylated SiNPs were collected and washed by repeated centrifugation at 21,000 g for 1 min (3 times with MilliQ water). PEGylated SiNPs were resuspended in MilliQ water and stored at 4° C.

Additional synthetic routes are outlined in Scheme 2 below with one or two reactive groups shown for clarity:

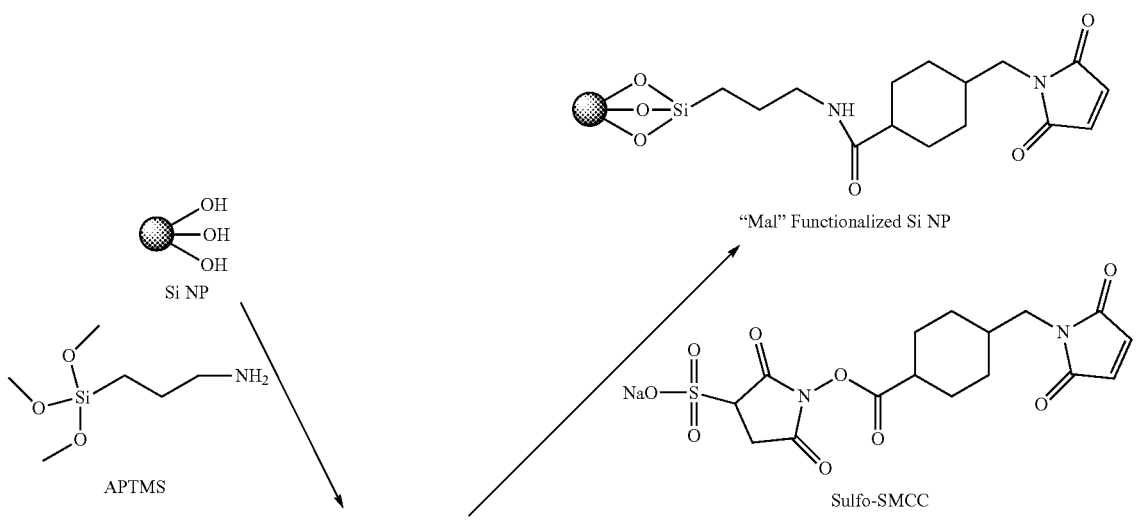

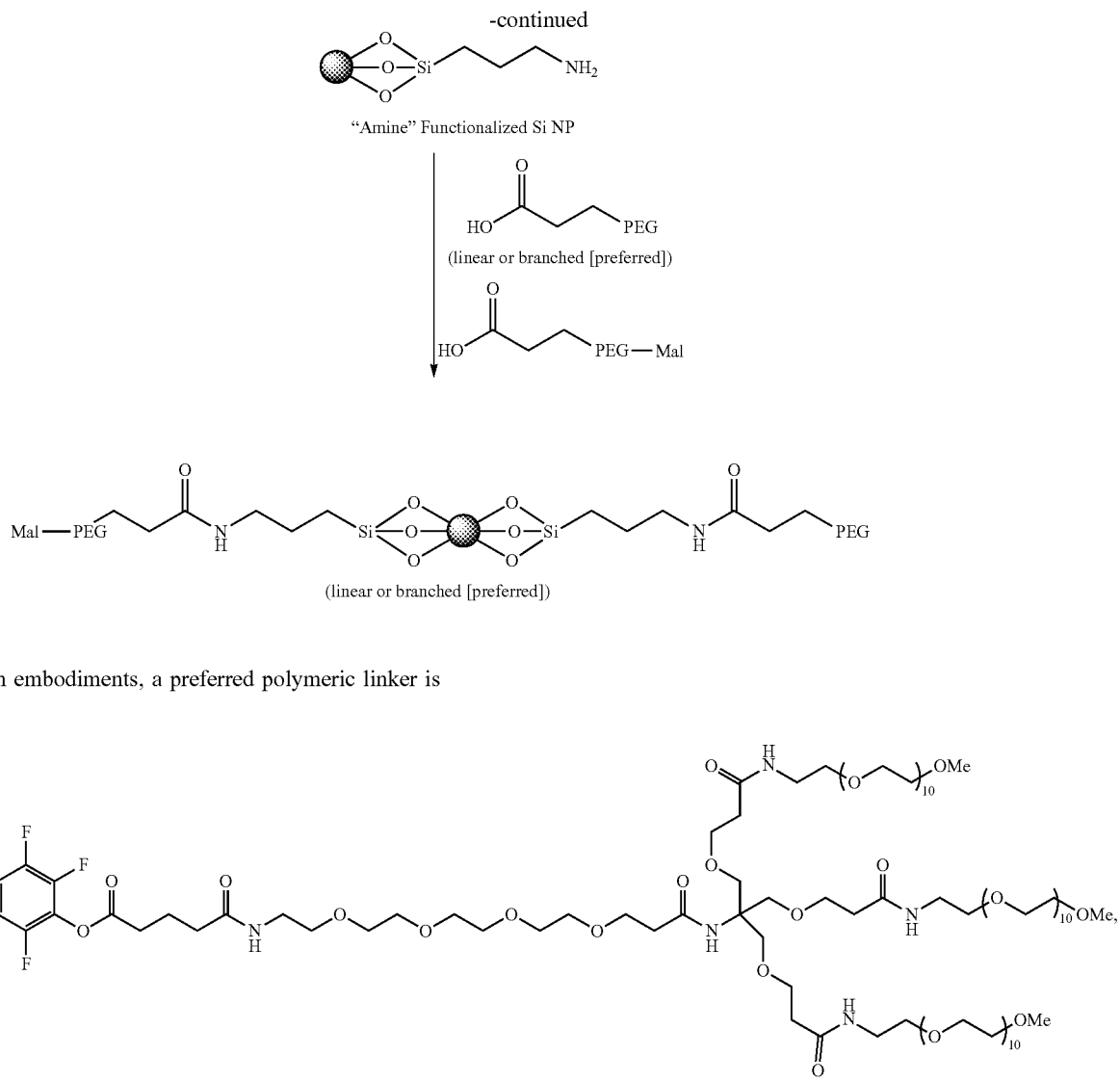
In embodiments, a preferred polymeric linker is
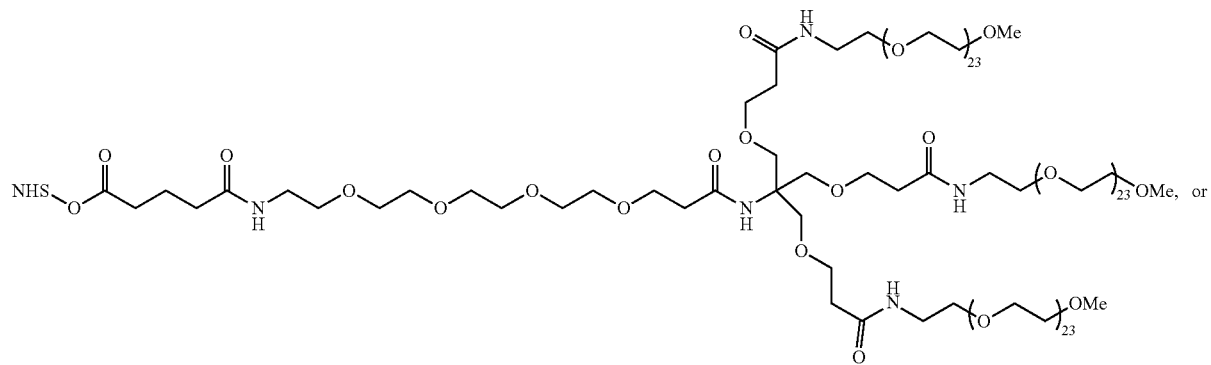

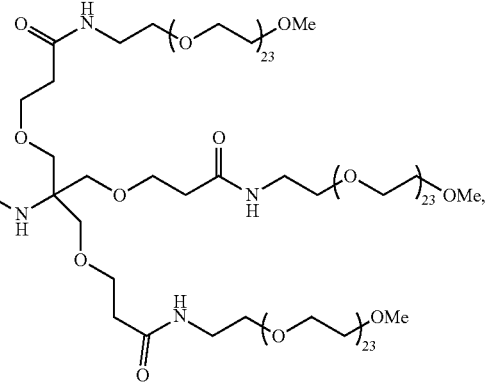

-continued

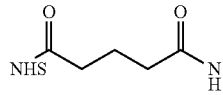

wherein NHS is N-hydroxysuccinimide.

Variables tested during the synthesis of SiNP-Cis: 1. The amount of cisplatin to load to each standard batch of SiNPs. The amount of silica precursor and the solvent system during the synthesis was kept consistent. The amount of cisplatin added during the reaction was varied to check the loading efficiency. 2. The type of drug: cisplatin vs. carboplatin. 3. The scale of the reaction. When the reaction was scaled up, it was tested whether the formation of SiNPs and the loading of cisplatin was consistent. 4. The stirring speed of the reaction. 5. The stability of cisplatin in the NPs. 6. Surface functionalization of SiNP-Cis. One batch of SiNP-Cis was PEGylated.

Variable 1: The amount of cisplatin. Comparing to the control nanoparticles SiNP-empty that do not have any drug added, SiNP-Cis particles loaded with 3 mg, 6 mg, and 12 mg cisplatin also maintained their morphology. They appear to be roughly the same size and shape as the control NPs. They are all monodisperse, and colloidally stable in water. The amount of Pt in cisplatin was quantified by ICP-MS: 10 μL of SiNP-Cis was added to a 15 mL tube followed by the addition of 1 mL of 70% concentrated nitric acid HNO3. SiNP-Cis was digested in 70% HNO3 for 1 h, at room temperature. Samples were diluted with MilliQ water to reach a desired concentration before ICP-MS measurements (ICP-MS measurement window: Pt 1 ppb-500 ppb). As the amount of cisplatin was increased during the synthesis, the Pt loading to the SiNPs appeared to reach a plateau between 6 mg and 12 mg as the loading efficiency dropped at 12 mg. All future preparations used 12 mg per batch as the standard synthesis procedure. The SiNP-Cis-3 mg had 1.9 μg/uL Pt, leaded Pt is about 1 mg, yielding a loading efficiency of 33%. The SiNP-Cis-6 mg had 3.7 μg/uL Pt, leaded Pt is about 1.8 mg, yielding a loading efficiency of 30%. The SiNP-Cis-12 mg had 5.2 μg/uL Pt, leaded Pt is about 2.6 mg, yielding a loading efficiency of 21.2%.

Variable 2: The type of drug encapsulated by SiNP. The synthesis of SiNP-Carbo was the same as a standard synthetic preparation of SiNP-Cis. Instead of 12 mg cisplatin, 12 mg of carboplatin was added to the reaction mixture. Comparing to SiNP-Cis particles, SiNP-Carbo also maintained their morphology. They appear to be roughly the same size and shape to SiNP-Cis.

Variable 3: The scale of the reaction. The syntheses of SiNP-Cis-3× and SiNP-Cis-5× followed the same procedure as in the 1× standard reaction with triple (3×) or quintuple (5×) the amount of reagents. Comparing to 1× SiNP-Cis particles, scaled up SiNP-Cis also maintained their morphology. They appear to be roughly the same size and shape to SiNP-Cis. The amount of Pt in these NPs was measured by ICP-MS.

Variable 4: The stirring speed. 1× reaction was stirred at speed 4 (500 rpm) whereas the 5× reaction was stirred at speed 4 and generated semi-empty SiNPs. This concludes us to stir all 5× reactions at speed 3 (400 rpm). Also, polystyrene serological pipettes are not chemical resistant and they should not be used to add cyclohexane or triton X-100 or hexanol to the reaction mixture. SiNP-Cis appeared to have some "empty" spots on them by TEM. This is due to dissolved polystryene from the pipettes that got incorporated to the SiNPs. This problem was solved by using all syringes to add the solvents.

Variable 5: The stability of SiNP-Cis in PBS and DMEM. SiNP-Cis were suspended in either full Dulbecco's Modified Eagle's Medium (DMEM) media or Phosphate-buffered saline (PBS) with 2% human serum albumin. They were incubated at 37° C. for 10 min, 30 min, 1 h, and 24 h. At each time point, the NPs were pelleted to the bottom of the eppendorf tube and a small fraction of the supernatant was collected (10 uL) for ICP-MS quantification of Pt. NPs were redispersed back into the solution by gently shaking. The 10 uL supernatant sample was added to a 15 mL tube and 1 mL concentrated 70% $HNO_3$ acid was added to digest the samples at room temperature for 1 h before measurements.

TABLE 2

3 different batches of SiNP—Cis were tested in the stability test.

| | Total amount of Pt in SiNP—Cis (ug) |
|---|---|
| Batch1 | 13.2 |
| Batch2 | 16 |
| Batch3 | 14.6 |

SiNP-Cis were stable in full DMEM media and PBS with 2% human serum albumin. After 24 h incubation at 37° C., only about 3% of Pt was lost in the supernatant.

Variable 6: Surface modification of SiNP-Cis-PEG. PEGylated SiNP-Cis retained their morphology as they had very similar shape and size to SiNP-Cis. The amount of Pt in SiNP-Cis-PEG was measured by ICP-MS, to be 0.1 μg/uL Pt.

Figure 21:
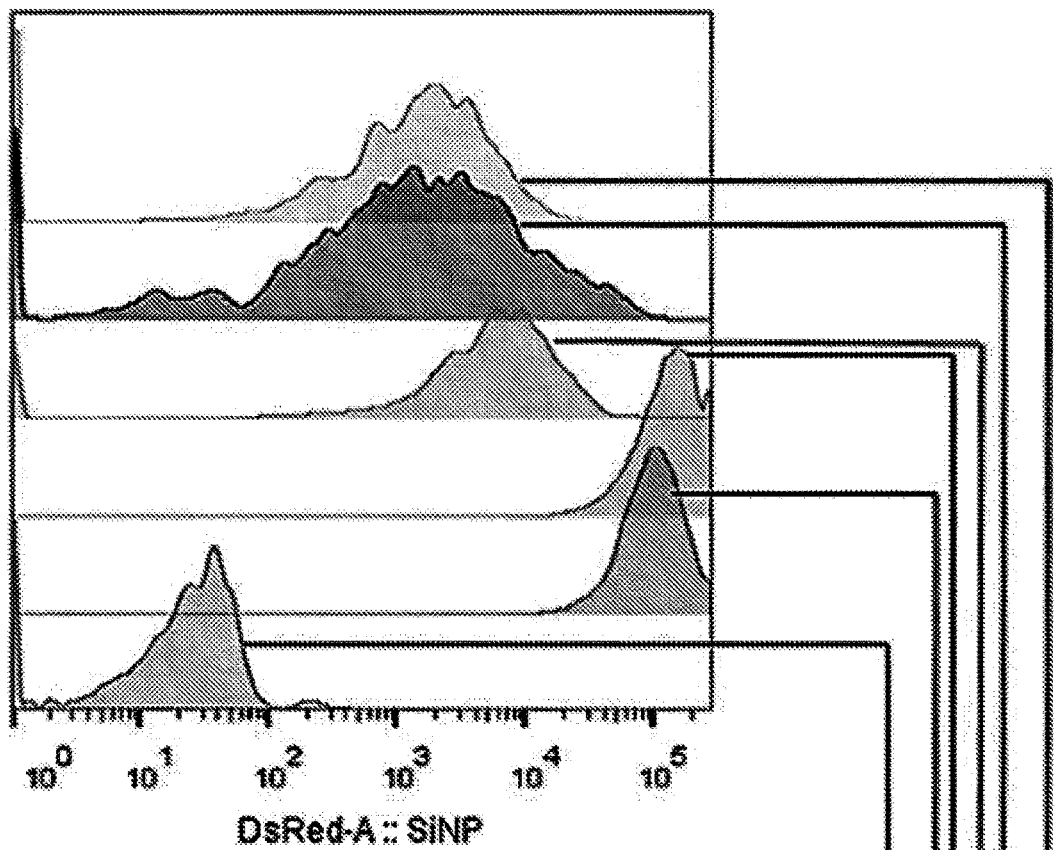
FIG. 21. Cell labeling to identify the non-specific binding of bare silica nanoparticles and PEG-silica nanoparticles to neural stem cells. NSCs treated with bare SiNPs have very high level of red fluorescence, indicating high level of non-specific binding and/or internalization of bare SiNPs to the cells. NSCs treated with PEGylated SiNPs have reduced non-specific binding and/or internalization of SiNPs to the cells.

Identifying the preferred ratio of non-functionalized PEG: functionalized PEG. NSCs were labeled with PEGylated SiNPs at both 4° C. and 37° C. for 30 min in FIG. 21A, and only at 37° C. for 30 min in FIG. 21B. At the composition of 80%:20%, the amount of Mal-PEG on the NP surface was low and NSCs were not optimally labeled with SiNPs. At the composition of 50%:50%, NSCs were labeled with much more NP-PEG11-3400. It appears that the shorter functional Mal-PEG3400 works better than the Mal-PEG5000. To ensure the reactivity between maleimide-thiol covalent bond formation, all future cell labeling steps were done at 37° C. At least 50% of functional Mal-PEGs in the coating to ensure NSC labeling is required. It appears that the short Mal-PEG3400 works better than the longer Mal-PEG5000, so we then tested Mal-PEG2000. It appears that labeling NSCs via functionalized PEGylated SiNPs reaches a limit which is consistent with what we found in the literature. NP attachment to the cell surface will eventually plateau as more NPs conjugate to cells. At 50%:50% composition, there was not much difference in the size of functional Mal-PEGs while making functional SiNPs. Mal-PEG2000 and Mal-PEG3400 appear to work better than Mal-PEG5000. At 80%:20%, Mal-PEG2000 works much better than Mal-PEG3400 and Mal-PEG5000 as it was able to label NSCs while the other two could not.

TEM experiments indicate empty silica nanoparticles (e.g., not loaded with a platinum containing compound) and platinum-loaded silica nanoparticles (e.g., Cisplatin loaded silica nanoparticles) have similar spherical morphology and size with a mean diameter of approximately 51 nm.

XPS survey spectrum of platinum-loaded silica nanoparticles (e.g., Cisplatin loaded silica nanoparticles) shows elemental composition of the NPs. High resolution spectra of platinum-loaded silica nanoparticles shows that Pt on the Si NPs is on +II state. Due to the absence of the chlorine band in the 198-200 eV region, it appears chlorine is not bound to the platinum following cisplatin conjugation to the silica nanoparticle.

Initial experiments on the stability of Cis-SiNPs and empty SiNPs indicate they dissolve in culture media and PBS in less than 24 h (using synthetic conditions in AB of Table 5 below). According to SiNPs synthesized using the AB method, analysis of the supernatant (water, DMEM/PBS) and the pellet after 24 hours reveal a portion of platinum (approximately 55%) is immediately released upon incubation in media or PBS and the rest remains encapsulated in the NPs (approximately 45%).

To optimize the delivery efficiency, modulating the synthetic conditions (i.e. changing the ratio of TEOS to $NH_4OH$) as seen in Table 5, changed the release profile and stability of the Cis-SiNPs and empty SiNPs.

TABLE 5

Synthesis conditions to optimize delivery.

| | $NH_4OH$ | |
|---|---|---|
| TEOS | 300 μL | 500 μL |
| 200 μL | AA | AB |
| 1000 μL | BA | BB |

Condition AA: Decreasing the $NH_4OH$ relative to AB, the silica is etched and the platinum is released in the supernatant at a similar rate to Cis-SiNPs synthesized according to AB. Approximately 60-75% of the platinum is released in the supernatant and 25-45% of the platinum remains in the nanoparticle.

Condition BB: Increasing the TEOS relative to AB, the nanoparticles become more dense and they are more stable. The silica is not etched and there is no burst release of the platinum. Approximately 10-15% of the platinum is released to the supernatant and 80-90% of the platinum is retained in the nanoparticle.

Condition BA: Increasing the TEOS and decreasing the $NH_4OH$ relative to AB. The nanoparticles synthesized by this method are more stable and have a desirable release profile. Approximately 10% of the platinum is released into the supernatant and 90-100% of the platinum is retained in the nanoparticle.

Utilizing the optimization protocol, the synthesis of the cisplatin loaded silica nanoparticles is as follows: Nonionic surfactant Triton X-100 (10 mL), Cyclohexane (35.8 mL), Hexanol (9 mL), TEOS (1000 μL), H2O (1.7 mL), 60 mg Cis cis-diamminedichloridoplatinum(II) (Cisplatin), 5 h later, ammonium hydroxide (300 uL), Stirring 16 h. The resulting NPs precipitated in Ethanol (centrifugation (4000 rpm, 10 min)), washed 2 times with Ethanol and 5 times with Water. Redispersed the final NPs Pellet in 2.5 mL Water. The nanoparticles synthesized via the AB method are sometimes referred to as 'Old Cis' and the nanoparticles synthesized according to the BA method are sometimes referred to as 'New Cis.'

TABLE 6

Properties of nanoparticles.

| | Size (nm) | Polydispersity index (PDI) | Zeta Potential (z) |
|---|---|---|---|
| SiNP—OH | 225.1 | 0.343 | −37.95 |
| SiNP—$NH_2$ | 440.3 | 0.366 | 26.76 |
| SiNP—Mal | 525.8 | 0.377 | −19.46 |
| SiNP—$PEG_{1000}$ | 482.3 | 0.064 | 30.55 |
| SiNP—$(PEG_{11})_3$ | 438.7 | 0.062 | 25.13 |
| SNP—$(PEG_{11})_3$—20% Mal | 447.3 | 0.116 | 19.90 |
| SiNP—$(PEG_{11})_3$—50% Mal | 481.6 | 0.021 | 14.24 |

TABLE 7

Synthesis details.

| | $NH_4OH$ | | | |
|---|---|---|---|---|
| | 300 μL | | 500 μL | |
| TEOS | Pt % in Supernatant | % Pt Pellet | Pt % in Supernatant | % Pt Pellet |
| 200 μL | 62.02 ± 1.40 | 34.56 ± 1.55 | 55.80 ± 3.83 | 48.14 ± 5.35 |
| 400 μL | 91.57 ± 3.7 | 4.9 ± 1.57 | 104 ± 22.19 | 3.26 ± 0.37 |
| 800 μL | 89.16 ± 10.22 | 11.14 ± 0.97 | 87.82 ± 6.3 | 12.94 ± 4.11 |
| 1000 μL | 9.65 ± 0.25 | 101.02 ± 4.41 | 9.19 ± 0.49 | 81.91 ± 30.95 |
| 1400 μL | 11.43 ± 1.13 | 90.07 ± 9.19 | 12.26 ± 0.11 | 87.73 ± 3.15 |
| 1800 μL | 10.61 ± 2.45 | 76.92 ± 5.78 | 8.25 ± 0.42 | 91.75 ± 0.005 |

B. In Vitro Efficacy

Assessing cell metabolic activity was performed using an MTT assay. Specifically, this MTT assay measures the cytotoxicity of free drug cisplatin, free NP carrier, and SiNP-Cis on cells. We tested their toxicities in NSCs and 2 ovarian cancer cell lines (OVCAR8 and Skov3) at 3 time points (after 1 d, 2 d, and 3 d). This assay was done in 96-well plates. To prepare the cells, a three step procedure was followed: 1. Plate 4000 cells/well in 100 uL full media to the 96-well plate 2. Each cell line was plated in 1 plates for each time point, for 3 days. NSCs and Skov3 cells were adhered well overnight. OV8 do not adhere well within 12-16 hr (overnight), so OV8 was given an extra day to adhere and stretch onto the plate. 3. Immediately prior to the drug treatment, take 5 μL of media out from each well (so that with the addition of 5 μL of solution containing free drug or free NP or SiNP-Cis solution, total volume of liquid remains 100 μL in each well).

Three solutions were prepared: 1. Free drug (cisplatin), 2. Free SiNPs, and 3. SiNP-Cis (drug-loaded SiNPs). The experimental conditions for the MTT assay are as follows: Doses of cisplatin (14 drug doses, and water as negative control, DMSO as positive control) 0, 0.0625, 0.125, 0.25, 0.5, 1, 2, 4, 8, 16, 32, 64, 128, 258 μM if cisplatin. Free cisplatin solutions were prepared by dissolving cisplatin powder in MilliQ water and a series of dilutions were made. SiNP-Cis solutions were made by matching the amount of Pt in the stock solution to the amount of Pt in the highest concentration of cisplatin free drug solution. A series of dilutions were made to obtain the lower concentrations of SiNP-Cis solutions. Free SiNPs solutions were prepared by matching the amount of SiNP in the free SiNP stock to the amount of SiNP carrier in the SiNP-Cis stock. A series of dilutions were made to obtain the lower concentrations of SiNP solutions.

MTT assay protocol: 1) at each time point (i.e. day1), create a 1 mg/mL MTT solution in warm media. 2) Filter the MTT using a sterile filter and syringe. 3) To each well, remove the old media, then add the new media with 1 mg/mL MTT. 4) Incubate cells at 37° C. for 1 hours, check every half an hour or so (make sure you see a gradient of purple color. Not too strong or too light). 5) Remove the MTT/media using a multi-well pipette. 6) Add in 100 μL of DMSO (does not need to be filtered) to dissolve the formazan crystals produced by the cells. To make sure all the crystals were dissolved, shake the plates gently and leave the plate at r.t. for 30 min before reading the plate. 7) Place the 96-well plate in the plate reader and measure the absorbance at 570 nm.

NSC–SiNP-Cis labeling studies to predict Pt loading. The experimental protocol is as follows: 1. 1M NSCs were plated in each well. 2. Old media of NSCs were removed and 1.5 mL of fresh media was added to each well before loading SiNP-Cis. 3. NSCs were incubated with SiNP-Cis at 37° C. for 1 h. 4. After 1 h, the media containing free NPs were removed and cells were washed once with PBS. 5. NSCs were then trypsinized to lift off the plate and collected by centrifugation (850 g, 3 min). 6. The supernatant was removed and the cell pellet was digested in 1 mL of concentrated HNO3. 7. The amount of Pt in 1M cells was measured by ICP-MS.

For each 1M NSCs, 1.7 μg of Pt was loaded on average. For the animal study, we planned to inject 10 M NSC–SiNP-Cis conjugates. Therefore, we estimated each animal would be injected with 17 μg of Pt. For animals to be injected with free drug and free drug NPs, they need to have matched amount of drug to the amount of Pt in the NSC+SiNP-Cis group (17 μg Pt/animal).

For the OV15-12 animal study, it was necessary to measure the Pt accumulation at tumors and in organs. There were four study groups: 1) PBS; 2) Free drug (cisplatin); 3) free drug SiNP-Cis; and 4) NSC–SiNP-Cis. Samples were collected from 6 tumors and 6 organs. For the groups of free drug (cisplatin), free drug NPs (SiNP-Cis), and NSC+NP-Cis, the targeted amount of Pt to inject to each animal was 17 μg/mouse. Each animal was injected with a total volume of 200 μL of PBS with 2% HBA that contained no drug, free drug, free drug NPs, or NSC+SiNP-Cis. To prepare the samples for injection: Group 2: cisplatin powder was dissolved in PBS with 2% HBA and dilutions were made to reach a final concentration of 85 μg Pt/mL for injection.

Group 3: Pt concentration in SiNP-Cis was measured by ICP-MS and dilutions were made to reach a final concentration of 85 μg Pt/mL for injection. Group 4: to prepare the NSC+SiNP-Cis sample: i) Each T175 flask containing roughly 10 M NSCs would be used to for 1 animal; ii) Old media of NSCs were removed and 7.5 mL of fresh media was added to each well before loading 1 mL SiNP-Cis; iii) NSCs were incubated with SiNP-Cis at 37° C. for 1 h; iv) After 1 h, the media containing free NPs were removed and cells were washed once with PBS; v) NSCs were then trypsinized (6 mL) to lift off the plate and collected by centrifugation (850 g, 3 min); vi) Each cell pellet was redispersed in 200 μL of PBS with 2% HBA and combined for animal injection.

TABLE 3

Amount of Pt in mice injection.

|  | Amount of platinum injected per mouse (μg) |
|---|---|
| Free drug | 8.3 |
| Free NPs | 17.7 |
| NSC—NP—Cis | 59.8 |

After animals were injected with free drug, free drug NPs, and NSC+SiNP-Cis, a small amount of each sample prepared was saved and measured by ICP-MS to assess the actual amount of Pt injected. Group 2 (free drug) were injected lower than estimated amount of Pt, 8.3 μg/animal. Group 3 (free drug NPs) were injected with the expected amount of Pt, 17.7 μg/animal. Group 4 (NSC+SiNP-Cis) were injected with higher than expected amount of Pt. It appears that the Pt loading study underestimated the amount of Pt that would load into each 1M NSCs. The amount of Pt accumulated at tumors and organs was measured by ICP-MS. Each tumor or organ was added to a 15 mL tube and it was digested by 1 mL of 70% HNO3 at 70° C. overnight (Livers needed 2 mL of conc. Acid). 4 mL of MilliQ water was added to each tube to dilute the samples prior to ICP-MS measurements. Due to the different amount of Pt injected to animals at the beginning, the measured Pt number in Group 2 and Group 3 were adjusted accordingly to match the amount of Pt in Group 4.

For the OV15-14 animal study, it was necessary to measure the Pt accumulation at tumors and in organs. There were three study groups: 1. Free drug (cisplatin); 2. Free drug NPs; and 3. NSC-NPs. Samples were obtained at 1 hr, 2 hr, 6, hr, and 24 hr increments with 12 mice in each group.

TABLE 4

OV15-14 animal study overview.

| 20151103-model addition of SiNP—Cis to NSCs for ICP-MS | |
|---|---|
| Free drug | |
| cisplatin MW | 300 g/mol |
| Pt MW | 195 g/mol |
| Each animal | Cisplatin treatment for mice: Target loading |
| Cisplatin conc (mg/kg) | 1.92 |
| mouse weight (g) | 20 |
| cisplatin per mouse | 0.038 |

TABLE 4-continued

OV15-14 animal study overview.

| | |
|---|---|
| Pt per mouse (mg) | 0.025 |
| Pt per mouse (μg) | 25 |

| Animal groups | For each animal |
|---|---|
| Cisplatin (free drug) | |
| Pt for 1 animal (μg) | 25 |
| total Pt for 18 animals (μg) | 450 |
| Pt conc (μg/μL) | 0.518 |
| total volume of Cisplatin solution (μL) | 869 |
| injection volume for 18mice (mL) | 18 |
| 2% HSA/PBS needed (mL) | 17.131 |
| NP only (free drug NPs) | |
| Pt conc in NP stock (μg/uL) | 3.45 |
| Pt for 1 animal (μg) | 25 |
| total Pt for 18 animals (μg) | 450 |
| NP volume | 130 |
| injection volume/animal (mL) | 1 |
| injection volume for 18mice (mL) | 18 |
| 2% HSA/PBS needed (mL) | 17.870 |
| NSC + NP | |
| Pt conc (μg/uL) | 0.025 |
| volume for 1 animal (μL) | 1000 |
| Pt for 1 animal (μg) | 25 |
| total Pt for 18 animals (μg) | 450 |
| injection volume/animal (mL) | 1 |
| injection volume for 18mice (mL) | 18 |

Experimental protocol for OV15-14 study: Each animal was injected with a total volume of 1 mL of PBS with 2% HBA that contained free drug, free drug NPs, or NSC+SiNP-Cis. For this experiment, to ensure that the exact same amount of Pt was injected in all groups of animals, the NSC+NP-Cis sample was prepared and the amount of Pt was determined right away by ICP-MS to be 25 μg/animal. For the groups of free drug (cisplatin) and free drug NPs (SiNP-Cis), a stock solution of each sample was prepared and measured by ICP-MS prior to injection. Dilution were made to match 25 μg/animal.

C. Using Neural Stem Cell-Nanoparticle Constructs to Selectively Deliver Therapeutics to Ovarian Cancer Ovarian cancer is a deadly disease that afflicts approximately 22,000 women per year in the US. Once the disease reaches stage III and has metastasized to the abdominal cavity, the 5-year survival rate is only 34%. Our goal is to develop stem cell/nanoparticle constructs for targeted and selective tumor killing in patients suffering from late stage ovarian cancer. Neural Stem Cells (NSCs) are appealing for use as targeted delivery platforms in the abdomen, as they have demonstrated inherent tumor tropic properties to ovarian cancer cells in vitro and in vivo following IP administration. However, NSCs do not intrinsically have any anti-tumor efficacy. As NSC-based therapy moves into the clinic, there is a need to develop complementary techniques to enable targeted delivery of chemotherapeutics by NSCs.

An attractive complementary approach involves the use of nanoparticles (NPs), which can be loaded with a broad spectrum of chemotherapeutic agents for delivery and dissemination at tumor sites. Therefore, we are developing delayed-drug release NP/NSC constructs to realize a modular and general drug targeting system. Here, we synthesized a library of model fluorescent silica NPs (SiNPs) with various surface functional groups, as well as cisplatin-loaded therapeutic silica NPs. The SiNPs were characterized by TEM, SEM, DLS, zetasizer, and the amount of Pt was quantified by ICP-MS. In vitro efficacy tests of these cisplatin-NPs demonstrated delayed drug release over 3 days. We then treated NSCs with cisplatin-NPs and injected these NSC-NP constructs in mice bearing ovarian cancer tumors. In this biodistribution study, the amount of Pt in tumors and organs were quantified by ICP-MS 24 h post injection. Our data demonstrated that NSC-NP constructs have much superior accumulation of Pt in tumors than both free cisplatin and free cisplatin-NPs. Current work focuses on the long term survival of ovarian cancer-bearing mice treated with NSC-NP constructs.

What is claimed is:

1. A nanoparticle-cell construct comprising an inorganic nanoparticle covalently attached to a cell surface protein through a covalent linker, wherein said cell surface protein is attached to a cell, and said covalent linker having the formula:

wherein:

$X^1$ and $X^2$ are independently a bioconjugate linker or a bond, wherein at least one of $X^1$ and $X^2$ is a bioconjugate linker having the formula:

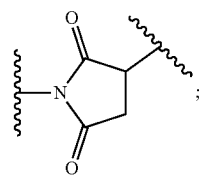 [SMILES: *C1CC(=O)N(*)C1=O]

$L^1$ is a polyethylene glycol;
$L^2$ is selected from:

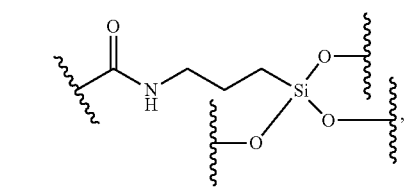

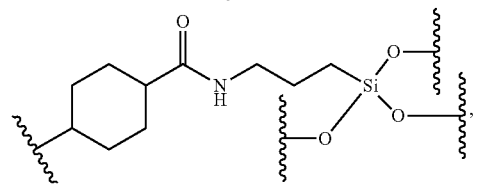

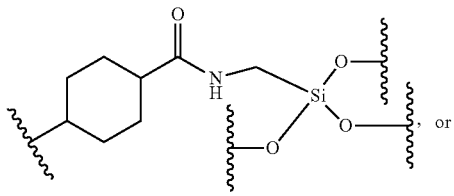

-continued

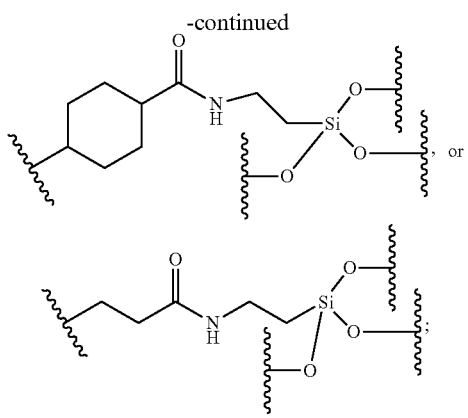

$L^3$ is —S—;
wherein $X^2$-$L^3$ has the formula:

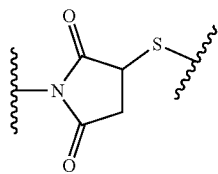 [SMILES: *SC1CC(=O)N(*)C1=O]

wherein said nanoparticle is further covalently attached to a plurality of nanoparticle substituents, wherein said plurality of nanoparticle substituents comprises the following:

-$L^2$-$X^1$—$R^3$;  (i) and

-$L^2$-$X^1$-$L^1$-$X^3$;  (ii); wherein $R^3$ is linear polyethylene glycol with an average molecular weight of about 2000 g/mol; and
$X^3$ is

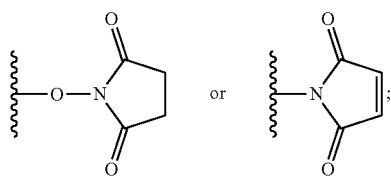 [SMILES: *ON1C(=O)CCC1=O ; *N1C(=O)C=CC1=O]

wherein the ratio of nanoparticle substituents of the formula (i) and nanoparticle substituents of the formula (ii) is about 50:50 and $L^1$ in formula (ii) is linear polyethylene glycol with an average molecular weight of 2000 g/mol; or wherein the ratio of nanoparticle substituents of the formula (i) and nanoparticle substituents of the formula (ii) is about 80:20 and $L^1$ in formula (ii) is linear polyethylene glycol with an average molecular weight of about 2000 g/mol.

2. A pharmaceutical composition comprising a pharmaceutically acceptable excipient and a nanoparticle-cell construct of claim 1.

3. The nanoparticle-cell construct of claim 1, wherein the inorganic nanoparticle comprises a platinum anti-cancer agent.

4. The nanoparticle-cell construct of claim 1, wherein $L^1$ in formula (Ia) is polyethylene glycol with an average molecular weight of 2000 g/mol.

5. The nanoparticle-cell construct of claim 1, wherein the cell is a tumor tropic cell, macrophage, stem cell, or T-cell.

6. The nanoparticle-cell construct of claim 1, wherein the cell is neural stem cell, a mesenchymal stem cell, a mesenchymal stromal cell, a hematopoietic stem cell, or a liver stem cell.

7. The nanoparticle-cell construct of claim 1, wherein the cell is genetically modified.

8. The nanoparticle-cell construct of claim 7, wherein the cell is a genetically modified neural stem cell.

9. The nanoparticle-cell construct of claim 8, wherein the genetically modified neural stem cell is a human HB1.F3 stem cell.

10. The nanoparticle-cell construct of claim 1, wherein the cell surface protein is a transmembrane protein.

11. The nanoparticle-cell construct of claim 1, wherein formula Ia and Ib do not include biotin.

12. The nanoparticle-cell construct of claim 1, wherein $L^1$ does not include poly(lactate)-poly(ethylene glycol) copolymer, poly(beta-amino ester), poly(lactate), poly(ethylene glycol)-dimethacrylate, or methyl ether poly(ethylene glycol)-poly(beta-amino ester) copolymer.

* * * * *